(12) United States Patent
Santamaria

(10) Patent No.: US 10,172,955 B2
(45) Date of Patent: Jan. 8, 2019

(54) COMPOSITIONS AND METHODS FOR THE PREVENTION AND TREATMENT OF CANCER

(71) Applicant: UTI Limited Partnership, Calgary (CA)

(72) Inventor: Pedro Santamaria, Calgary (CA)

(73) Assignee: UTI Limited Partnership (CA)

( * ) Notice: Subject to any disclaimer, the term of this patent is extended or adjusted under 35 U.S.C. 154(b) by 0 days.

(21) Appl. No.: 15/353,602

(22) Filed: Nov. 16, 2016

(65) Prior Publication Data

US 2017/0274096 A1 Sep. 28, 2017

Related U.S. Application Data

(63) Continuation of application No. 13/294,109, filed on Nov. 10, 2011, now Pat. No. 9,511,151.

(60) Provisional application No. 61/413,330, filed on Nov. 12, 2010.

(51) Int. Cl.
| | | |
|---|---|---|
| A61K 38/00 | (2006.01) | |
| C07K 14/00 | (2006.01) | |
| A61K 47/48 | (2006.01) | |
| A61K 47/62 | (2017.01) | |
| A61K 47/69 | (2017.01) | |

(52) U.S. Cl.
CPC .. *A61K 47/48861* (2013.01); *A61K 47/48238* (2013.01); *A61K 47/48884* (2013.01); *A61K 47/62* (2017.08); *A61K 47/6923* (2017.08); *A61K 47/6929* (2017.08)

(58) Field of Classification Search
None
See application file for complete search history.

(56) References Cited

U.S. PATENT DOCUMENTS

| | | | |
|---|---|---|---|
| 4,367,110 A | 1/1983 | Yoshikawa | |
| 4,414,148 A | 11/1983 | Jansen et al. | |
| 4,452,901 A | 6/1984 | Gordon et al. | |
| 4,478,946 A | 10/1984 | Van Der Merwe et al. | |
| 4,554,101 A | 11/1985 | Hopp | |
| 4,569,789 A | 2/1986 | Blattler et al. | |
| 4,589,071 A | 5/1986 | Yamamuro et al. | |
| 4,589,330 A | 5/1986 | Teron | |
| 4,659,839 A | 4/1987 | Nicolotti et al. | |
| 4,671,958 A | 6/1987 | Rodwell et al. | |
| 4,680,338 A | 7/1987 | Sundoro | |
| 4,699,784 A | 10/1987 | Shih et al. | |
| 4,818,542 A | 4/1989 | Deluca et al. | |
| 4,859,839 A | 8/1989 | Tetelman et al. | |
| 5,258,499 A | 11/1993 | Konigsberg et al. | |
| 5,543,391 A | 8/1996 | Yatvin et al. | |
| 5,676,926 A | 10/1997 | Platzek et al. | |
| 5,676,928 A | 10/1997 | Klaveness et al. | |
| 5,731,168 A | 3/1998 | Carter et al. | |
| 5,807,706 A | 9/1998 | Carter et al. | |
| 5,821,333 A | 10/1998 | Carter et al. | |
| 5,840,839 A | 11/1998 | Wang et al. | |
| 6,103,379 A | 8/2000 | Margel et al. | |
| 6,387,498 B1 | 5/2002 | Coulter et al. | |
| 6,651,655 B1 | 11/2003 | Licalsi et al. | |
| 6,688,494 B2 | 2/2004 | Pozarnsky et al. | |
| 6,712,997 B2 | 3/2004 | Won et al. | |
| 6,797,514 B2 | 9/2004 | Berenson et al. | |
| 6,846,474 B2 | 1/2005 | Nayfeh et al. | |
| 6,929,675 B1 | 8/2005 | Bunge et al. | |
| 7,060,121 B2 | 6/2006 | Lin et al. | |
| 7,090,973 B1 | 8/2006 | Breton | |
| 7,183,065 B2 | 2/2007 | Braun et al. | |
| 7,285,289 B2 | 10/2007 | Nagy et al. | |
| 7,326,399 B2 | 2/2008 | Zhou et al. | |
| 7,332,586 B2 | 2/2008 | Franzen et al. | |
| 7,361,733 B2 | 4/2008 | Hershberg et al. | |
| 7,572,631 B2 | 8/2009 | Berenson et al. | |

(Continued)

FOREIGN PATENT DOCUMENTS

| | | |
|---|---|---|
| CA | 2517097 A1 | 9/2004 |
| CA | 2717719 A | 8/2009 |

(Continued)

OTHER PUBLICATIONS

Australian Patent Application No. 2016225913 Examination Report No. 1 dated Sep. 22, 2017.
Bahcetepe et al, "The role of HLA antigens in the aetiology of psoriasis," Med Glas (Zenica) 10(2):339-342, 2013.
Baker et al., Critical appraisal of animal models of multiple sclerosis. Multiple Sclerosis Journal, 17(6):647-657, 2011.
Betts et al., "CD8(+) T cells in asthma: Friend or foe?" Pharmacology & Therapeutics 121 :123-131, 2009.

(Continued)

*Primary Examiner* — Michail A Belyavskyi
(74) *Attorney, Agent, or Firm* — Wilson Sonsini Goodrich & Rosati

(57) ABSTRACT

Conventional cancer immunotherapy falls short at efficiently expanding T cells that specifically target cancerous cells in numbers sufficient to significantly reduce the tumor size or cancerous cell number in vivo. To overcome this limitation, provided herein are nanoparticles coated with MHC class I and/or class II molecules presenting tumor-specific antigens and co-stimulatory molecules and their use to expand antigen-specific anti-tumorigenic T cells to levels not achieved in current immunotherapeutic techniques. These antigen-specific anti-tumorigenic T cells include cytotoxic T cells, effector T cells, memory T cells, and helper T cells that are necessary to initiate and maintain a substantial immune response against metastatic or non-metastatic cancerous, pre-cancerous, or neoplastic cells in vivo. The present invention describes a systemic approach to targeting cancerous or pre-cancerous cells that are circulating cells, as in lymphomas, migratory metastatic cells, and solid tumors.

25 Claims, 12 Drawing Sheets
Specification includes a Sequence Listing.

(56) References Cited

U.S. PATENT DOCUMENTS

| | | |
|---|---|---|
| 7,642,228 B2 | 1/2010 | Carter et al. |
| 7,695,936 B2 | 4/2010 | Carter et al. |
| 8,216,805 B2 | 7/2012 | Carter et al. |
| 8,679,785 B2 | 3/2014 | Carter et al. |
| 8,835,144 B2 | 9/2014 | Jiang et al. |
| 9,149,440 B2 | 10/2015 | Turos et al. |
| 9,511,151 B2 | 12/2016 | Santamaria et al. |
| 2003/0068363 A1 | 4/2003 | Clark et al. |
| 2003/0124149 A1 | 7/2003 | Shalaby et al. |
| 2004/0115216 A1 | 6/2004 | Schneck et al. |
| 2004/0137642 A1 | 7/2004 | Erfle et al. |
| 2004/0265392 A1 | 12/2004 | Tovar et al. |
| 2005/0003431 A1 | 1/2005 | Wucherpfennig et al. |
| 2005/0118102 A1 | 6/2005 | Xiang et al. |
| 2005/0129617 A1 | 6/2005 | Tan et al. |
| 2005/0202032 A1 | 9/2005 | Kaufman et al. |
| 2005/0208120 A1 | 9/2005 | Albani |
| 2006/0219239 A1 | 10/2006 | Plaschkes |
| 2007/0054337 A1 | 3/2007 | Ferning et al. |
| 2007/0059775 A1 | 3/2007 | Hultman et al. |
| 2007/0129307 A1 | 6/2007 | Tan et al. |
| 2007/0154953 A1 | 7/2007 | Brunner et al. |
| 2009/0155292 A1 | 6/2009 | Santamaria et al. |
| 2009/0258355 A1 | 10/2009 | Maye et al. |
| 2010/0061984 A1 | 3/2010 | Greene et al. |
| 2010/0095544 A1 | 4/2010 | Haseloh |
| 2010/0104503 A1 | 4/2010 | Mellman et al. |
| 2010/0303866 A1 | 12/2010 | Saint-Remy |
| 2011/0029121 A1 | 2/2011 | Amit |
| 2011/0059121 A1 | 3/2011 | Santamaria et al. |
| 2011/0250146 A1 | 10/2011 | Zhang et al. |
| 2011/0318380 A1 | 12/2011 | Brix et al. |
| 2012/0077686 A1 | 3/2012 | Weiner et al. |
| 2012/0093934 A1 | 4/2012 | Santamaria |
| 2012/0121649 A1 | 5/2012 | Santamaria et al. |
| 2013/0128138 A1 | 5/2013 | Kuo et al. |
| 2013/0171179 A1 | 7/2013 | Burrows |
| 2013/0302421 A1 | 11/2013 | Santamaria et al. |
| 2013/0330414 A1 | 12/2013 | Santamaria |
| 2014/0105980 A1 | 4/2014 | Santamaria |
| 2014/0294982 A1 | 10/2014 | Freund et al. |
| 2014/0341938 A1 | 11/2014 | Rademacher et al. |
| 2014/0370099 A1 | 12/2014 | Green et al. |
| 2015/0125536 A1 | 5/2015 | Santamaria |
| 2015/0209446 A1 | 7/2015 | Santamaria |
| 2015/0250871 A1 | 9/2015 | Santamaria |
| 2015/0344586 A1 | 12/2015 | Georges et al. |
| 2015/0374815 A1 | 12/2015 | Kishimoto et al. |
| 2016/0271237 A1 | 9/2016 | Santamaria |
| 2017/0095544 A1 | 4/2017 | Santamaria |
| 2017/0312348 A1 | 11/2017 | Santamaria |
| 2017/0333540 A1 | 11/2017 | Santamaria et al. |

FOREIGN PATENT DOCUMENTS

| | | |
|---|---|---|
| CA | 2868551 A1 | 10/2013 |
| CN | 101678090 A | 3/2010 |
| EP | 0 188 256 | 7/1986 |
| EP | 1088256 A2 | 4/2001 |
| EP | 2 614 834 | 7/2013 |
| EP | 2621523 A1 | 8/2013 |
| EP | 3269384 A1 | 1/2018 |
| EP | 3291832 A2 | 3/2018 |
| JP | H07508503 A | 9/1995 |
| JP | 2001516571 A | 10/2001 |
| JP | 2002504342 A | 2/2002 |
| JP | 2002544170 A | 12/2002 |
| JP | 2003231698 A | 8/2003 |
| JP | 2005538083 A | 12/2005 |
| JP | 2006522319 A | 9/2006 |
| JP | 2007508503 A | 4/2007 |
| JP | 2008514686 A | 5/2008 |
| JP | 2010522695 A | 7/2010 |
| JP | 2013538208 A | 10/2013 |
| WO | WO-9007339 A1 | 7/1990 |
| WO | WO-92/18150 A1 | 10/1992 |
| WO | WO-9301716 A1 | 2/1993 |
| WO | WO-93/16725 A1 | 9/1993 |
| WO | WO-9316725 A1 | 9/1993 |
| WO | WO-9409823 A1 | 5/1994 |
| WO | WO-9806749 A2 | 2/1998 |
| WO | WO-9914236 A1 | 3/1999 |
| WO | WO-0043662 A1 | 7/2000 |
| WO | WO-00/67788 A2 | 11/2000 |
| WO | WO-01/24764 A2 | 4/2001 |
| WO | WO-2004/006951 A1 | 1/2004 |
| WO | WO-2004/078909 A2 | 9/2004 |
| WO | WO-2004076909 A1 | 9/2004 |
| WO | WO-2005/033267 A2 | 4/2005 |
| WO | WO-2005036035 A2 | 4/2005 |
| WO | WO-2006/037979 A2 | 4/2006 |
| WO | WO-2006054806 A1 | 5/2006 |
| WO | WO-2006/080951 A2 | 8/2006 |
| WO | WO-2007024026 A1 | 3/2007 |
| WO | WO-2008051245 A2 | 5/2008 |
| WO | WO-2008/109852 A2 | 9/2008 |
| WO | WO-2008/118861 A2 | 10/2008 |
| WO | WO-2009/003492 | 1/2009 |
| WO | WO-2009031258 A1 | 3/2009 |
| WO | WO-2009/040811 A2 | 4/2009 |
| WO | WO-2009/078799 | 6/2009 |
| WO | WO-2009/094273 A2 | 7/2009 |
| WO | WO-2009/111588 A1 | 9/2009 |
| WO | WO-2009/126835 A2 | 10/2009 |
| WO | WO-2010/025324 A2 | 3/2010 |
| WO | WO-2010/027827 A2 | 3/2010 |
| WO | WO-2010/037397 A1 | 4/2010 |
| WO | WO-2010037395 A2 | 4/2010 |
| WO | WO-2010042876 A1 | 4/2010 |
| WO | WO-2010/080032 A2 | 7/2010 |
| WO | WO-2010085509 A1 | 7/2010 |
| WO | WO-2011/073685 A1 | 6/2011 |
| WO | WO-2011/104497 A1 | 9/2011 |
| WO | WO-2012/031258 A1 | 3/2012 |
| WO | WO-2012041968 A1 | 4/2012 |
| WO | WO-2012062904 A2 | 5/2012 |
| WO | WO-2013/043662 | 3/2013 |
| WO | WO-2013072051 A1 | 5/2013 |
| WO | WO-2013144811 A2 | 10/2013 |
| WO | WO-2014080286 A2 | 5/2014 |
| WO | WO-2015063616 A2 | 5/2015 |
| WO | WO-2016198932 A2 | 12/2016 |
| WO | WO-2018087597 A1 | 5/2018 |

OTHER PUBLICATIONS

Bossuyt et al., Serologic markers in inflammatory bowel disease. Clinical Chemistry, 52(2):171-181, 2006.
Chang et al., "Design, engineering, and production of human recombinant T-cell receptor ligands derived from human leukocyte antigen DR2," Journal of Biological Chemistry 276(26):24170-6, 2001.
China Patent Application No. 201380022126.2 fourth Office Action dated Jul. 24, 2017.
Clemente-Caseres, J. "pMHC-class II Nanovaccine to Treat Autoimmune Diseases," Doctor of Philosophy Thesis, Calgary University, Alberta, Canada, 391 pages, 2014. retrieved from: http://theses.ucalgary.ca/handle/11 023/1589.
Clemente-Caseres et al , Peptide-MHC-based nanovaccines for the treatment of autoimmunity: a "one size fits all" approach? J. Mol. Med., 89: 733-742, 2011.
Cnop et al., "Mechanisms of Pancreatic beta-Cell Death in Type 1 and Type 2 Diabetes," Diabetes 54(2):S97-S107.
Constantinescu et al., "Experimental autoimmune encephalomyelitis (EAE) as a model for multiple sclerosis (MS)," British Journal of Pharmacology 164:1079-1106, 2011.
Corrigall et al., "Autoantigens and immune pathways in rheumatoid arthritis," Crit Rev Immunol. 22(4):281-293, 2002.
Croxford et al., "Mouse models for multiple sclerosis: Historical facts and future implications," Biochimica et Biophysica Acta 1812:177-183, 2011.

(56) References Cited

OTHER PUBLICATIONS

Denic et al., "The relevance of animal models in multiple sclerosis research," Pathophysiology 18:21-29, 2011.
Dieterich et al., Identification of tissue transglutaminase as the autoantigen of celiac disease. Nature Medicine, 3(7):797-801, 1997.
European Patent Application No. 13856460.4 Extended European Search Report dated Feb. 26, 2016.
Fifis et al., "Short Peptide Sequences Containing MHC Class I and/or Class II Epitopes Linked to Nano-Beads Induce Strong Immunity and Inhibition of Growth of Antigen-Specific Tumour Challenge in Mice," Vaccine 23(2):258-266, 2004.
Frankel et al., "Characterization of diphtheria fusion proteins targeted to the human interleukin-3 receptor," Protein Engineering 13(8):575-581, 2000.
Gold et al., "Understanding pathogenesis and therapy of multiple sclerosis via animal models: 70 years of merits and culprits in experimental autoimmune encephalomyelitis research," Brain 129:1953-1971, 2006.
Gregori et al., "Re-establishing immune tolerance in type 1 diabetes via regulatory T cells," Novartis Found Symp. 292:abstract, 2008.
Gunn et al., A multimodal targeting nanoparticle for selectively labeling T cells. Small. 4(6):712-715, 2008.
Guo et al., "Protein tolerance to random amino acid change," PNAS 101 (25):9205-9210, 2004.
Gupta et al., Synthesis and surface engineering of iron oxide nanoparticles for biomedical applications. Biomat. 26:3995-4021, 2005.
Harris et al., "Prediction of murine MHC class I epitopes in a major house dust mite allergen and induction of T1-type CD8 T cell responses," Int Immunol. 9(2):273-280, 1997.
Ho et al., "The clinical relevance of autoantibodies in scleroderma," Arthritis Res Ther. 5(2):80-93, 2003.
Holgate and Polosa, Treatment strategies for allergy and asthma. Nature, 8: 218-230, 2008.
Japanese Patent Application No. 2015-536240 Office Action dated Aug. 16, 2017.
Japanese Patent Application No. 2017-014194 Office Action dated Sep. 13, 2017.
Jarius et al., "Mechanisms of Disease: aquaporin-4 antibodies in neuromyelitis optica," Nat Clin Pract Neurol. 4(4):202-214, 2008.
Kita et al., "Quantitative and functional analysis of PDC-E2-specific autoreactive cytotoxic T lymphocytes in primary biliary cirrhosis," J Clin Invest. 109(9):1231-1240, 2002.
Kyger et al., "Effective Arrestin-Specific Immunotherapy of Experimental Autoimmune Uveitis with RTL: A Prospect for Treatment of Human Uveitis," Transl Vis Sci Technol. 2(2): 1-15, 2013.
Longhi et al., "Autoantigen-Specific Regulatory T Cells, a Potential Tool for Immune-Tolerance Reconstitution in Type-2 Autoimmune Hepatitis," Hepatology 53(2):536-547, 2011.
Mallone et al., "T Cell Recognition of Autoantigens in Human Type 1 Diabetes: Clinical Perspectives," Clinical and Developmental Immunology (513210): 1-16, 2011.
Marsh et al., "Nomenclature for factors of the HLA system, update Oct. 2010," Human Immunology 72(4):364-369, 2011.
Mei, et al., Chemical Industry Press. Biotechnology pharmaceutic preparation: foundation and application: 199, 2004.
Mexican Patent Application No. Mx/a/2013/003559 third Office Action dated Jul. 3, 2017.
Mexican Patent Application No. MX/a/2014/011623 office action dated Jul. 28, 2017.
Miguel-Sancho et al., Development of stable, water-dispersible, and biofunctionalizable superparamagnetic iron oxide nanoparticles. Chemistry of Materials, 23:2795-2802, 2011.
Moore et al., Tracking the recruitment of diabetogenic CD8+ T-cells to the pancreas in real time. Diabeters, 53:1459-1466, 2004.
Nelson, J., 6 Types of asthma and how they're treated. J. mnn.com, Nov. 17, 2015, 4 pages.
Pachner. "Experimental models of multiple sclerosis," Current Opinion in Neurology 24:291-299, 2011.
Packard et al, "COPD is associated with production of autoantibodies to a broad spectrum of self-antigens, correlative with disease phenotype," Immunol Res. 55(1-3):48-57, 2013.
Pakula et al., "Genetic Analysis of Protein Stability and Function," Annu. Rev. Genet. 23:289-310, 1989.
PCT/EP2011/066994 International Search Report and Written Opinion dated Nov. 21, 2011.
PCT/EP2011/069931 International Search Report and Written Opinion dated Jul. 10, 2012.
PCT/IB2013/003033 International Search Report and Written Opinion dated Jul. 14, 2014.
PCT/IB2013/052352 International Search Report and Written Opinion dated Oct. 2, 2013.
PCT/IB2014/003014 International Search Report and Written Opinion dated May 12, 2015.
PCT/IB2016/000691 International Search Report and Written Opinion dated Mar. 7, 2017.
PCT/US2008/056279 International Search Report and Written Opinion dated Oct. 22, 2008.
Riemekasten et al., "Key autoantigens in SLE," Rheumatology (Oxford) 44(8):975-982, 2005.
Routsias et al., "Autoimmune response and target autoantigens in Sjogren's syndrome," Eur J Clin Invest. 40(11):1026-1036, 2010.
Shao et al., "Nanoparticle-Based Immunotherapy for Cancer," ACS Nano 9(1): 16-30, 2015.
Shukla et al., "Emerging nanotechnologies for cancer immunotherapy," Exp Biol Med (Maywood) 241 (10):1116-1126, 2016.
Sollid et al., "Nomenclature and listing of celiac disease relevant gluten T-cell epitopes restricted by HLA-DQ molecules," Immunogenetics 64(6):455-460, 2012.
Szczerkowska-Dobosz, A. "Human Leukocyte Antigens as Psoriasis Inheritance and Susceptibility Markers," Arch Immunol Ther Exp (Warsz) 53(5):428-433, 2005.
Takahashi et al., Isolation and characterization of a colonic autoantigen specifically recognized by colon tissue bound immunoglobulin G from idiopathic ulcerative colitis. J.Clinical Invest., 76:311-318, 1985.
Tanimura et al., "Beta2-Giycoprotein 1/HLA class II complexes are novel autoantigens in antiphospholipid syndrome," Blood 125(18):2835-2844, 2015.
UniProtKB: D4VD94. from www.uniprot.org/uniprot!D4VD94. 2010.
U.S. Appl. No. 15/348,959 First Action Interview Pilot Program, Pre-Interview Communication dated Apr. 13, 2017.
U.S. Appl. No. 12/044,435 Office Action dated Jun. 8, 2011.
U.S. Appl. No. 12/044,435 Office Action dated May 2, 2012.
U.S. Appl. No. 12/044,435 Office Action dated Nov. 24, 2010.
U.S. Appl. No. 12/848,055 Office Action dated Apr. 4, 2012.
U.S. Appl. No. 12/848,055 Office Action dated Aug. 23, 2012.
U.S. Appl. No. 12/848,055 Office Action dated Dec. 19, 2012.
U.S. Appl. No. 12/848,055 Office Action dated Dec. 24, 2014.
U.S. Appl. No. 12/848,055 Office Action dated Jun. 6, 2014.
U.S. Appl. No. 12/848,055 Office Action dated May 13, 2016.
U.S. Appl. No. 13/249,105 Office Action dated Apr. 3, 2015.
U.S. Appl. No. 13/249,105 Office Action dated Nov. 30, 2015.
U.S. Appl. No. 13/249,105 Office Action dated Sep. 8, 2017.
U.S. Appl. No. 13/712,832 Office Action dated Feb. 27, 2015.
U.S. Appl. No. 13/830,521 Office Action dated Jul. 25, 2014.
U.S. Appl. No. 13/830,521 Office Action dated Jun. 28, 2016.
U.S. Appl. No. 13/830,521 Office Action dated Mar. 5, 2015.
U.S. Appl. No. 13/842,302 Office Action dated Apr. 30, 2014.
U.S. Appl. No. 13/842,302 Office Action dated Feb. 18, 2015.
U.S. Appl. No. 13/842,302 Office Action dated Jul. 6, 2016.
U.S. Appl. No. 13/842,302 Office Action dated May 3, 2017.
U.S. Appl. No. 14/531,707 Office Action dated Oct. 3, 2017.
U.S. Appl. No. 14/684,153 Office Action dated Jun. 30, 2016.
U.S. Appl. No. 14/723,268 Office Action dated Mar. 30, 2016.
U.S. Appl. No. 14/723,268 Office Action dated Oct. 16, 2015.
U.S. Appl. No. 15/348,959 Office Action dated Aug. 30, 2017.
U.S. Appl. No. 15/433,898 Office Action dated Sep. 28, 2017.
Van Boekel et al., "Autoantibody systems in rheumatoid arthritis: specificity, sensitivity and diagnostic value," Arthritis Res. 4(2):87-93, 2002.

(56) References Cited

OTHER PUBLICATIONS

Van Driel et al., "Role of regulatory T cells in gastrointestinal inflammatory disease," Journal of Gastroenterology and Hepatology 23:171-177, 2008.
Vandenbarkk et al., "Recombinant TCR ligand induces tolerance to myelin oligodendrocyte glycoprotein 35-55 peptide and reverses clinical and histological signs of chronic experimental autoimmune encephalomyelitis in HLA-DR2 transgenic mice," Journal of Immunology 171(1):127-33, 2003.
Wang et al., One-pot reaction to synthesize superparamagnetic iron oxide nanoparticles by adding phenol as reducing agent and stabilizer. Journal of Nanoparticle Res., 14:755, 7 pages, 2012.
Wen et al., "3. Surface effect of the nanoparticles," Introduction to Nature Science:373-374, 2007.
Wilson et al., "pH-Responsive Nanoparticle Vaccines for Dual-Delivery of Antigens and Immunostimulatory Oligonucleotides," ASC Nano 7(5):3912-3925, 2013.
WO2004078909—Bibliographic data page from EPO webiste showing it was also published as US2007154953, downloaded Nov. 15, 2010, 1 page.
Wu et al., "Magnetic Iron Oxide Nanoparticles: Synthesis and Surface Functionalization Strategies," Nanoscale Res Lett. 3:397-415, 2008.
Wucherpfennig et al., "Structural basis for major histocompatibility complex (MHC)-linked susceptibility to autoimmunity: charged residues of a single MHC binding pocket confer selective presentation of self-peptides in pemphigus vulgaris," PNAS 92(25):11935-11939, 1995.
Xie et al., Controlled PEGylation of monodisperse Fe3O4 nanoparticles for reduced non-specific uptake by macrophage cells. Advanced Materials, 19:3163-3166, 2007.
Xie et al., One-pot synthesis of monodisperse iron oxide nanoparticles for potential biomedical applications. Pure Applied Chemicals, 78(5):1003-1014, 2006.
Xu et al., Oleylamine as both reducing agent and stabilizer in a facile synthesis of magnetite nano particles. Chemical Materials, 21:1778-1780, 2009.
Xu, H. "13.3.3 Relationship between gene transduction and nanoparticle size," Nano Medicine:35S, 2004.
Yadav et al., "Recombinant T-Cell Receptor Ligand (RTL) for Treatment of Multiple Sclerosis: A Double-Blind, Placebo-Controlled, Phase 1, Dose-Escalation Study," Autoimmune Diseases 2012(954 739):1-11, 2012.
Yeste et al., "Nanoparticle-mediated co-delivery of myelin antigen and a tolerogenic small molecule suppresses experimental autoimmune encephalomyelitis," PNAS 109(28): 11270-11275, 2012.
U.S. Appl. No. 15/610,550, filed May 31, 2017, UTI Limited Partnership; The General Hospital Corporation.
Aichele, P. et al. (1994) "Peptide-induced T-cell tolerance to prevent autoimmune diabetes in a transgenic mouse model," Proc. Natl. Acad. Sci. USA 91:444-448.
Amrani, A. et al. (2000) "Progression of autoimmune diabetes driven by avidity maturation of a T-cell population," Nature 406:739-742.
Amrani, A. et al. (2001) "Expansion of the Antigenic Repertoire of a Single T Cell Receptor upon T Cell Activation," J. Immunol. 167:655-666.
Anderson, B. et al. (1999) "Prevalent CD8(+) T cell response against one peptide/MHC complex in autoimmune diabetes," Proc. Natl. Acad. Sci. USA 96:9311-9316.
Anderton, S.M. et al. (1998) "Hierarchy in the ability of T cell epitopes to induce peripheral tolerance to antigens from myelin," Eur. J. Immunol. 28:1251-1261.
Appay, V. et al. (2000) "HIV-specific CD8(+) T Cells Produce Antiviral Cytokines but Are Impaired in Cytoltic Function," J. Exp. Med. 192(1):63-72.
Author Unknown (2002) Diabetes Prevention Trial—Type 1 Diabetes Study Group, "Effects of Insulin in Relatives of Patients with Type 1 Diabetes Mellitus," N. Engl. J. Med. 346:1685-1691.
Author Unknown (2010) KidsHealth from Nemours, "Can Diabetes Be Prevented?," Website article from kidshealth.org/PageManager.jsp?dn=KidsHealth&lic=1&ps=107&caUd=139&article; downloaded Nov. 9, 2010, 2 pages.
Azuma, M. et al. (2000) "T Cell Costimulation and Diseases," Stomatological Journal 67(3):233-239.
Bachmann, M.F. et al. (1999) "Developmental Regulation of Lck Targeting to the CD8 Coreceptor Controls Signaling in Naive and Memory T Cells," J. Exp. Med. 189:1521-1530.
Barber, D.L. et al. (2006) "Restoring function in exhausted CD8 T cells during chronic viral infection," Nature 439:682-687.
Becker, T.C. et al. (2002) "Interleukin 15 Is Required for Proliferative Renewal of Virus-specific Memory CD8 T Cells," J. Exp. Med. 195(12):1541-1548.
Behan, P.O. et al. (2010) "The sad plight of multiple sclerosis research (low on fact, high on fiction): critical data to support it being a neurocristopathy," Inflammopharmacol 18:265-290.
Bibliographic data page from EPO website at espacenet.com/publicationDetails/biblio?CC=WO&NR=2004078909A2&KC=. . . , downloaded Nov. 15, 2010, showing that W02004078909 was also published as US2007154953: 1 page total.
Bielekova, B. et al. (2000) "Encephalitogenic potential of the myelin basic protein peptide (amino acids 83-99) in multiple sclerosis: Results of a phase II clinical trial with an altered peptide ligand," Nat. Med. 6(10):1167-1175.
Blancou, P. et al. (2007) "Immunization of HLA Class I Transgenic Mice Identifies Autoantigenic Epitopes Eliciting Dominant Responses in Type 1 Diabetes Patients," J. Immunol. 178:7458-7466.
Bottazzo, G.F. et al. (1985) "In situ characterization of autoimmune phenomena and expression of HLA molecules in the pancreas in diabetic insulitis," N. Engl. J. Med. 313(6):353-360.
Bottini, M. et al. (2007) "Luminescent Silica Nanobeads: Characterization and Evaluation as Efficient Cytoplasmatic Transporters for T-Lymphocytes," J. Am. Chem. Soc.129(25):7814-7823.
Bour-Jordan, H. et al. (2007) "B cell depletion: a novel therapy for autoimmune diabetes?" J. Clin. Invest. 117:3642-3645.
Braud, V.M. et al. (1999) "Functions of nonclassical MHC and non-MHC-encoded class I molecules," Current Opinion in Immunology 11:100-108.
Cao, K. et al. (2001) "Analysis of the Frequencies of HLA-A, B, and C Alleles and Haplotypes in the Five Major Ethnic Groups of the United States Reveals High Levels of Diversity in These Loci and Contrasting Distribution Patterns in These Populations," Hum. Immunol. 62:1009-1030.
Chatenoud, L. (2002) "Do NKT cells control autoimmunity?" J. Clin. Invest. 110(6):747-748.
Cirillo, C. et al. (2011) "S100B protein in the gut: The evidence for enteroglial-sustained intestinal inflammation," World J Gastroenterol. 17(10):1261-1266.
Clemente-Casares, X. et al. (2011) "Peptide-MHC-based nanovaccines for the treatment of autoimmunity: a 'one size fits all' approach?," J. Mol. Med. 89:733-742.
Cuiv, P.O. et al. (2011) "Draft Genome Sequence of Bacteroides vulgatus PC510, a Strain Isolated from Human Feces," Journal of Bacteriology 193(15):4025-4026.
Database Accession No. ADK001000110 (2011) "Bacteroides vulgatus PC510 contig00041, whole genome shotgun sequence."
Database Accession No. D4VD94 (2010) "Subname: Full= Conserved domain protein," from www.uniprot.org/uniprot/D4VD94.
Dilorenzo, T.P. et al. (1998) "Major histocompatibility complex class I-restricted T cells are required for all but the end stages of diabetes development in nonobese diabetic mice and use a prevalent T cell receptor alpha chain gene rearrangement," Proc. Natl. Acad. Sci. USA 95:12538-12543.
Diwan, M. et al. (2003) "Biodegradable nanoparticle mediated antigen delivery to human cord blood derived dendritic cells for induction of primary T cell responses," J. Drug Target 11(8-10):495-507.
Dominguez, A.L. et al. (2010) "Targeting the tumor microenvironment with anti-neu/anti-CD40 conjugated nanoparticles for the induction of antitumor immune responses," Vaccine 28(5):1383-1390.

(56) References Cited

OTHER PUBLICATIONS

Dressel, A. et al. (1997) "Autoantigen recognition by human CD8 T cell clones: enhanced agonist response induced by altered peptide ligands," J. Immunol. 159: 4943-4951.

Eggena, M. et al. (2000) "Identification of Histone H1 as a Cognate Antigen of the Ulcerative Colitis-associated Marker Antibody pANCA," Journal of Autoimmunity 14:83-97.

Fennessy, M. et al. (1994) "A gene in the HLA class I region contributes to susceptibility to IDDM in the Finnish population," Diabetologia 37:937-944.

Final Office Action in U.S. Appl. No. 13/294,109, dated Jan. 12, 2015.

Final Office Action in U.S. Appl. No. 13/294,109, dated Nov. 13, 2013.

Flad, T. et al. (2003) "Development of an MHC-class I peptide selection assay combining nanoparticle technology and matrix-assisted laser desorption/ionisation mass spectrometry," J. Immunol. Meth. 283:205-213.

Gill, R.G. et al. (1989) "Characterization of Primary T Cell Subsets Mediating Rejection of Pancreatic Islet Grafts," Journal of Immunology 143(7):2176-2178.

Gimmi, C.D. et al. (1993) "Human T-cell clonal anergy is induced by antigen presentation in the absence of B7 costimulation," Proc. Natl. Acad. Sci. USA 90:6586-6590.

Gong, W. et al. (2010) "Immobilized MHC class I chain-related protein A synergizes with IL-15 and soluble 4-1BB ligand to expand NK cells with high cytotoxicity ex vivo," Cellular & Molecular Immunology 7(6):477-484.

Guarda, G. et al. (2007) "L-selectin-negative CCR7(−) effector and memory CD8(+) T cells enter reactive lymph nodes and kill dendritic cells," Nat. Immunol. 8(7):743-752.

Hamilton-Williams, E.E. et al. (2001) "Transgenic rescue implicates beta2-microglobulin as a diabetes susceptibility gene in nonobese diabetic (NOD) mice," Proc. Natl. Acad. Sci. USA 98(20):11533-11538.

Han, B. et al. (2005) "Developmental control of CD8(+) T cell-avidity maturation in autoimmune diabetes," J. Clin. Invest. 115(7):1879-1887.

Han, B. et al. (2005) "Prevention of diabetes by manipulation of anti-IGRP autoimmunity: high efficiency of a low-affinity peptide," Nat. Med. 11:645-652.

Han, G. et al. (2009) "Interleukin-17-producing ys T Cells protect NOD mice from type 1 diabetes through a mechanism involving transforming growth factor-b," Immunology 129:197-206.

Hassainya, Y. et al. (2005) "Identification of Naturally Processed HLA-A2—Restricted Proinsulin Epitopes by Reverse Immunology," Diabetes 54:2053-2059.

Herold, K.C. et al. (2002) "Anti-CD3 monoclonal antibody in new onset type I diabetes mellitus," N. Eng. J. Med. 346:1692-1698.

Honeyman, M.C. et al. (1995) "Analysis of Families at Risk for Insulin-Dependent Diabetes Mellitus Reveals that HLA Antigens Influence Progression to Clinical Disease," Molecular Medicine 1(5):576-582.

International Search Report from International Application No. PCT/EP2011/069931 dated Jul. 10, 2012, 9 pages.

Itoh, N. et al. (1993) "Mononuclear Cell Infiltration and Its Relation to the Expression of Major Histocompatibility Complex Antigens and Adhesion Molecules in Pancreas Biopsy Specimens from Newly Diagnosed Insulin-dependent Diabetes Mellitus Patients," J. Clin. Invest. 92:2313-2322.

Jarchum, I. et al. (2007) "In Vivo Cytotoxicity of Insulin-Specific CD8(+) T-Cells in HLA-A*0201 Transgenic NOD Mice," Diabetes 56:2551-2560.

Jarchum, I. et al. (2008) "Identification of novel IGRP epitopes targeted in type 1 diabetes patients," Clin. Immunol. 127:359-365.

Judge, A.D. et al. (2002) "Interleukin 15 Controls both Proliferation and Survival of a Subset of Memory-Phenotype CD8(+) T Cells," J. Exp. Med. 196(7):935-946.

Jun, H-S. et al. (2003) "A new look at viruses in type 1 diabetes," Diabetes Metab. Res. Rev. 19:8-31.

Jurewicz, A. et al. (1998) "MHC Class I-Restricted Lysis of Human Oligodendrocytes by Myelin Basic Protein Peptide-Specific CD8 T Lymphocytes," J. Immunol. 160:3056-3059.

Kamikura, Y. et al. (2004) "Adhesion, Costimulatory Molecule, Trafficking, Homing: Cancer Immunotherapy and Costimulatory Molecule," Annual Review, Immunity.

Kappos, L. et al. (2000) "Induction of a non-encephalitogenic type 2 T helper-cell autoimmune response in multiple sclerosis after administration of an altered peptide ligand in a placebo-controlled, randomized phase II trial," Nat. Med. 6(10):1176-1182.

Karin, N. et al. (1994) "Reversal of Experimental Autoimmune Encephalomyelitis by a Soluble Peptide Variant of a Myelin Basic Protein Epitope: T Cell Receptor Antagonism and Reduction of Interferon gamma and Tumor Necrosis Factor alpha Production," J. Exp. Med. 180:2227-2237.

Karounos, D.G. et al. (1997) "Metabolically Inactive Insulin Analog Prevents Type I Diabetes in Prediabetic NOD Mice," J. Clin. Invest. 100:1344-1348.

Kent, S.C. et al. (2005) "Expanded T cells from pancreatic lymph nodes of type 1 diabetic subjects recognize an insulin epitope," Nature 435:224-228.

Keymeulen, B. et al. (2005) "Insulin Needs after CD3-Antibody Therapy in New-Onset Type 1 Diabetes," N. Engl. J. Med. 352:2598-2608.

Kim, S-K. et al. (1999) "Induction and Visualization of Mucosal Memory CD8 T Cells Following Systemic Virus Infection," J. Immunol. 163:4125-4132.

Komai-Koma, M. et al. (2004) "TLR2 is expressed on activated T cells as a costimulatory receptor," PNAS 101(9):3029-3034.

Krishnamoorthy, G. et al. (2009) "Myelin-specific T cells also recognize neuronal autoantigen in a transgenic mouse model of multiple sclerosis," Nature Medicine 15(6):626-633.

Kukreja, A. et al. (2002) "NKT Cells and Type-1 Diabetes and the "hygiene Hypothesis" to Explain the Rising Incidence Rate," Diabetes Technology & Therapeutics 4(3):323-333.

Kulmala, P. (2003) "Prediabetes in Children," Pediatr Drugs, 5(4):211-221.

Kwong, B. et al. (2010) "Synthesis and characterization of antibody-nanoparticle conjugates for locally sequestered tumor immunotherapy," Abstracts of Papers American Chemical Society 240(POLY 61):POLY.

Laurence, A. et al. (2007) "TH-17 differentiation: of mice and men," Nature Immunology 8(9):903-905.

Lechner, F. et al. (2000) "Analysis of Successful Immune Responses in Persons Infected with Hepatitis C Virus," J. Exp. Med. 191(9):1499-1512.

Lee, Y. et al. (2010) "Biodegradable Nanoparticles Containing TLR3 or TLR9 Agonists Together with Antigen Enhance MHC-restricted Presentation of the Antigen," Arch. Pharm. Res. 33(11):1859-1866.

Liblau, R.S. et al. (2002) "Autoreactive CD8 T cells in Organ-Specific Autoimmunity: Emerging Targets for Therapeutic Intervention," Immunity 17:1-6.

Lieberman, S.M. et al. (2003) "A comprehensive guide to antibody and T-cell responses in type 1 diabetes," Tissue Antigens 62:359-377.

Lieberman, S.M. et al. (2003) "Identification of the beta cell antigen targeted by a prevalent population of pathogenic CD8(+) T cells in autoimmune diabetes," PNAS 100(14):8384-8388.

Lieberman, S.M. et al. (2004) "Individual Nonobese Diabetic Mice Exhibit Unique Patterns of CD8(+) T Cell Reactivity to Three Islet Antigens, Including the Newly Identified Widely Expressed Dystrophia Myotonica Kinase," J. Immunol. 173:6727-6734.

Lowery, A.R. et al. (2006) "Immunonanoshells for targeted photothermal ablation of tumor cells," Int J Nanomedicine 1(2):149-154.

Ma, Z. et al. (2014) "TCR triggering by pMHC ligands tethered on surfaces via poly(ethylene glycol) depends on polymer length," PLoS One 9(11):e112292, pp. 1-10.

Mallone, R. et al. (2007) "CD8(+) T-Cell Responses Identify beta-Cell Autoimmunity in Human Type 1 Diabetes," Diabetes 56:613-621.

(56) References Cited

OTHER PUBLICATIONS

Maree, A.F.M. et al. (2006) "Modeling competition among autoreactive CD8(+) T cells in autoimmune diabetes: implications for antigen-specific therapy," International Immunology 18(7):1067-1077.
Mars, L.T. et al. (2007) "CD8 T Cell Responses to Myelin Oligodendrocyte Glycoprotein-Derived Peptides in Humanized HLA-A*0201-Transgenic Mice," J. Immunol. 179:5090-5098.
McKown, K.M. et al. (1999) "Lack of efficacy of oral bovine type II collagen added to existing therapy in rheumatoid arthritis," Arthritis & Rheumatism 42(6):1204-1208.
Mescher, M.F. et al. (2006) "Signals required for programming effector and memory development by CD8(+) T cells," Immunol. Rev. 211:81-92.
Mestas, J. et al. (2004) "Of Mice and Not Men: Differences between Mouse and Human Immunology," The Journal of Immunology 172:2731-2738.
Metzler, B. et al. (1993) "Inhibition of experimental autoimmune encephalomyelitis by inhalation but not oral administration of the encephalitogenic peptide: influence of MHC binding affinity," Int. Immunol. 5(9):1159-1165.
Miller, S.D. et al. (1979) "The induction of cell-mediated immunity and tolerance with protein antigens coupled to syngeneic lymphoid cells," J. Exp. Med. 149:758-773.
Moore, A. et al. (2004) "Tracking the Recruitment of Diabetogenic CD8(+) T-Cells to the Pancreas in Real Time," Diabetes 53(6):1459-1466.
Nakayama, M. et al. (2005) "Prime role for an insulin epitope in the development of type 1 diabetes in NOD mice," Nature 435(7039):220-223.
Non-Final Office Action in U.S. Appl. No. 13/294,109, dated Jun. 4, 2013.
Notice of Allowance in U.S. Appl. No. 13/294,109, dated Apr. 4, 2016.
Notice of Allowance in U.S. Appl. No. 13/294,109, dated Sep. 29, 2016.
Oh, S. et al. (2004) "IL-15 / IL-15R alpha-mediated avidity maturation of memory CD8(+) T cells," PNAS 101(42):15154-15159.
Oleszak, E.L. et al. (2004) "Theiler's Virus Infection: a Model for Multiple Sclerosis," Clinical Microbiology Reviews 17(1):174-207.
Ouyang, Q. et al. (2006) "Recognition of HLA Class I-Restricted beta-Cell Epitopes in Type 1 Diabetes," Diabetes 55:3068-3074.
Palmer, J.P. et al. (1983) "Insulin Antibodies in Insulin-Dependent Diabetics Before Insulin Treatment," Science 222:1337-1339.
Pascolo, S. et al. (1997) "HLA-A2.1-restricted Education and Cytolytic activity of CD8(+) T Lymphocytes from beta2 Microglobulin (beta2m) HLA-A2.1 Monochain Transgenic H-2D(b) beta2m Double Knockout Mice," J. Exp. Med. 185(12):2043-2051.
Patel, J.D. et al. (2007) "Cationic Nanoparticles for Delivery of CpG Oligodexoynucleotide and Ovalbumin: In Vitro and In Vivo Assessment," Journal of Biomedical Nanotechnology 3(1):97-106.
Petros, R. et al. (2007) "Antibody conjugation to PRINT nanoparticles as a cellular targeting strategy," Abstracts of Papers American Chemical Society 233(COLL 14):COLL14.
Pinkse, G.G.M. et al. (2005) "Autoreactive CD8 T cells associated with beta cell destruction in type 1 diabetes," PNAS 102(51):18425-18430.
Purton, J.F. et al. (2007) "Antiviral CD4(+) memory T cells are IL-15 dependent," Journal of Experimental Medicine 204(4):951-961.
Ransohoff, R.M. et al. (2012) "Animal models of multiple sclerosis: the good, the bad and the bottom line," Nature Neuroscience 15(8):1074-1077.
Restriction Requirement in U.S. Appl. No. 13/294,109, dated Mar. 19, 2013.
Santamaria, P. (2001) "Effector lymphocytes in autoimmunity," Curr. Opin. Immunol. 13:663-669.
Santamaria, P. et al. (1992) "Characterization of T lymphocytes infiltrating human pancreas allograft affected by isletitis and recurrent diabetes," Diabetes 41:53-61.
Santamaria, P. et al. (1994) "Skewed T-cell receptor usage and junctional heterogeneity among isletitis alpha beta and gamma omega T cells in human IDDM (insulin-dependent diabetes mellitus)," Diabetes 43:599-606.
Santamaria, P. et al. (1995) "Beta-Cell-Cytotoxic CD8(+) T Cells from Nonobese Diabetic Mice Use Highly Homologous T Cell Receptor alpha-Chain CDR3 Sequences," J. Immunol. 154:2494-2503.
Saragovi, H.U. et al. (1999) "Small molecule and protein-based neurotrophic ligands: agonists and antagonists as therapeutic agents," Exp. Opin. Ther. Patents 9(6):737-751.
Schirle, M. et al. (2001) "Combining computer algorithms with experimental approaches permits the rapid and accurate identification of T cell epitopes from defined antigens," J. Immunol. Methods 257:1-16.
Schneider, K. et al. (2009) "The end of the era of generosity? Global health amid economic crisis," Philos Ethic, Humanit Med. 4:1.
Schnutgen, F. et al. (2003) "A directional strategy for monitoring Cre-mediated recombination and the cellular level in the mouse," Nat. Biotech. 21:562-566.
Schreiber, H.A. et al. (2010) "Using carbon magnetic nanoparticles to target, track, and manipulate dendritic cells," Journal of Immunological Methods 356(1-2):47-59.
Serreze, D.V. et al. (2001) "Autoreactive Diabetogenic T-Cells in NOD Mice Can Efficiently Expand From a Greatly Reduced Precursor Pool," Diabetes 50:1992-2000.
Shanks, N. et al. (2009) "Are animal models predictive for humans?" Philosophy, Ethics, and Humanities in Medicine 4(2):1-20.
Sibley, R.K et al. (1985) "Recurrent Diabetes Mellitus in the Pancreas Iso- and Allograf: A Light and Electron Microscopic and Immunohistochemical Analysis of Four Cases," Lab. Invest. 53(2):132-144.
Somoza, N. et al. (1994) "Pancreas in Recent Onset Insulin-Dependent Diabetes Mellitus. Changes in HLA, Adhesion Molecules and Autoantigens, Restricted T Cell Receptor V beta Usage, and Cytokine Profile," J. Immunol. 153:1360-1377.
Spada, F.M., et al. (2000) "Self-Recognition of CD1 by $\gamma/s$ T Cells: Implications for Innate Immunity," J. Exp. Med. 191(6):937-948.
Sprent, J. et al. (2001) "T Cell Death and Memory," Science 293:245-248.
Sprent, J. et al. (2002) "T Cell Memory," Annu. Rev. Immunol. 20:551-579.
Standifer, N.E. et al. (2006) "Identification of Novel HLA-A*0201-Restricted Epitopes in Recent-Onset Type 1 Diabetic Subjects and Antibody-Positive Relatives," Diabetes 55:3061-3067.
'T Hart, B.A. et al. (2004) "Modelling of multiple sclerosis: lessons learned in a non-human primate," Lancet Neurology 3:588-597.
Tait, B.D. et al. (1995) "HLA Antigens and Age at Diagnosis of Insulin-Dependent Diabetes Mellitus," Hum. Immunol. 42:116-124.
Takaki, T. et al. (2006) "HLA-A*0201-Restricted T Cells from Humanized NOD Mice Recognize Autoantigens of Potential Clinical Relevance to Type 1 Diabetes," J. Immunol. 176:3257-3265.
Tan, J.T. et al. (2002) "Interleukin (IL)-15 and IL-7 Jointly Regulate Homeostatic Proliferation of Memory Phenotype CD8(+) Cells but Are Not Required for Memory Phenotype CD4(+) Cells," J. Exp. Med. 195(12):1523-1532.
Toes, R.E.M. et al. (1996) "Peptide vaccination can lead to enhanced tumor growth through specific T-cell tolerance induction," Proc. Natl. Acad. Sci. USA 93:7855-7860.
Toma, A. et al. (2005) "Recognition of a subregion of human proinsulin by class I-restricted T cells in type 1 diabetic patients," Proc. Natl. Acad. Sci. USA 102(30):10581-10586.
Trenttham, D.E. et al. (1993) "Effects of Oral Administration of Type II Collagen on Rheumatoid Arthritis," Science 261:1727-1730.
Trudeau, J.D. et al. (2003) "Prediction of spontaneous autoimmune diabetes in NOD mice by quantification of autoreactive T cells in peripheral blood," J. Clin. Invest. 111:217-223.
Tsai, S. et al. (2010) "Reversal of Autoimmunity by Boosting Memory-like Autoregulatory T Cells," Immunity 32(4):568-580.
Tsuchida, T. et al. (1994) "Autoreactive CD8(+) T-cell responses to human myelin protein-derived peptides," Proc. Natl. Acad. Sci. USA, 91:10859-10863.

(56) References Cited

OTHER PUBLICATIONS

Tufveson, G. et al. (1993) "New Immunosuppressants: Testing and Development in Animal Models and the Clinic: with Special Reference to DSG," Immunological Reviews 136:101-107.
Unger, W.W.J. et al. (2007) "Human Clonal CD8 Autoreactivity to an IGRP Islet Epitope Shared between Mice and Men," Ann. N. Y. Acad. Sci. 1103:192-195.
Van Belle, T.L. et al. (2011) "Type 1 Diabetes: Etiology, Immunology, and Therapeutic Strategies," Physiol. Rev. 91:79-118.
Verdaguer, J. et al. (1996) "Acceleration of Spontaneous Diabetes in TCR-beta-Transgenic Nonobese Diabetic Mice by beta-Cell Cytotoxic CD8(+) T Cells Expressing Identical Endogenous TCR-alpha Changes," The Journal of Immunology 157:4726-4735.
Verdaguer, J. et al. (1997) "Spontaneous Autoimmune Diabetes in Monoclonal T Cell Nonobese Diabetic Mice," J. Exp. Med. 186(10):1663-1676.
Verdu, E.F. et al. (2000) "Oral administration of antigens from intestinal flora anaerobic bacteria reduces the severity of experimental acute colitis in BALB/c mice," Clin Exp Immunol. 120:46-50.
Vincent, M.S. et al. (2003) "Understanding the function of CD1-restricted T cells," Nat. Immunol. 4(6):517-523.
Wainwright, S.D. et al. (2000) "HLA-F Is a Predominantly Empty, Intracellular, TAP-Associated MHC Class Ib Protein with a Restricted Expression Pattern," J. Immunol. 164(1):319-328.
Walter, U. et al. (2005) "CD8(+) T cells in autoimmunity," Curr. Opin. Immunol. 17:624-631.
Wang, X. et al. (2007) "Induction of Potent CD8( ) T-Cell Responses by Novel Biodegradable Nanoparticles Carrying Human Immunodeficiency Virus Type 1 gp120," Journal of Virology 81(18):10009-10016.
Warnock, G.L. et al. (1991) "Normoglycaemia after transplantation of freshly isolated and cryopreserved pancreatic islets in Type 1 (insulin-dependent) diabetes mellitus," Diabetologia 34:55-58.
Weiner, H.L. et al. (1993) "Double-Blind Pilot Trial of Oral Tolerization with Myelin Antigens in Multiple Sclerosis," Science 259:1321-1324.
Weiss, G.A. et al. (1996) "Covalent HLA-B27/peptide complex induced by specific recognition of an aziridine mimic of arginine," Proc. Natl. Acad. Sci. USA 93:10945-10948.
Wekerle, H. et al. (2006) "Animal models of multiple sclerosis," Drug Discovery Today: Disease Models 3(4):359-367.
Williams, M.A. et al. (2006) "Developing and maintaining protective CD8(+) memory T cells," Immunol. Rev. 211:146-153.
Winer, S. et al. (2003) "Autoimmune islet destruction in spontaneous type 1 diabetes is not beta-cell exclusive," Nat. Med. 9(2):198-205.
Wong, F.S. et al. (1999) "Identification of an MHC class I-restricted autoantigen in type 1 diabetes by screening an organ-specific cDNA library," Nat. Med. 5(9):1026-1031.
Wraith, D.C. et al. (1989) "Antigen Recognition in Autoimmune Encephalomyelitis and the Potential for Peptide-Mediated Immunotherapy," Cell 59:247-255.
Yamanouchi, J. et al. (2007) "Interleukin-2 gene variation impairs regulatory T cell function and causes autoimmunity," Nat. Genet. 39(3):329-337.
Zajac, A.J. et al. (1998) "Viral Immune Evasion Due to Persistence of Activated T Cells Without Effector Function," J. Exp. Med. 188(12):2205-2213.
Zhang, S. et al. (2010) "HMGB1, an innate alarmin, in the pathogenesis of type 1 diabetes," Int. J. Clin. Exp. Pathol. 3(1):24-38.
Mazzarella. Effector and Suppressor T Cells in Celiac Disease. World J Gastroenterol 21(24):7349-7356 (2015).
PCT/IB2017/001508 International Search Report and Written Opinion dated Mar. 26, 2018.
Peng et al. Synthesis and characterization of monodisperse hollow Fe3O4 nanoparticles. Angew Chem 119:4233-4236 (2007).
Sato. Diabetes and cytokines. Roles of cytokines in diabetes mellitus, separate volume, Journal of Clinical and Experimental Medicine, cytokine-state of arts, 2004 (5 pgs).

Serra et al., Nanoparticle-based approaches to immune tolerance for the treatment of autoimmune diseases. European Journal of Immun., 0:1-6, 2018.
U.S. Appl. No. 13/249,105 Office Action dated Apr. 11, 2018.
U.S. Appl. No. 13/842,302 Office Action dated Apr. 30, 2018.
Altman, J.D. et al. Phenotypic Analysis of Antigen-Specific T Lymphocytes. Science 274:94-96, 1996.
Australia Patent Application No. 2016203231 Examination Report No. 2 dated Nov. 30, 2017.
Babbe, H. et al. Clonal expansions of CD8(+) T cells dominate the T cell infiltrate in active multiple sclerosis lesions as shown by micromanipulation and single cell polymerase chain reaction. J. Exp. Med. 192, 393-404, 2000.
Bacchetta, R. et al. High levels of interleukin 10 production in vivo are associated with tolerance in SCID patients transplanted with HLA mismatched hematopoietic stem cells. J. Exp. Med. 179:493-502, 1994.
Bailey-Bucktrout, S. L. et al. Self-antigen-driven activation induces instability of regulatory T cells during an inflammatory autoimmune response. Immunity 39, 949-962, 2013.
Bakker et al. MHC Multimer Technology: Current Status and Future Prospects. Current Opinion in Immunology, 17(4):428-433, 2005.
Buenafe et al., Regulatory T-cells play a role in T-cell receptor CDR2 peptide regulation of experimental autoimmune encephalomyelitis. Immunology, 135(2):168-179, 2012.
Burke et al., The influence of adjuvant on the therapeutic efficacy of a recombinant genital herpes vaccine. J. Inf. Dis., 170:1110-1119, 1994.
Burton, B.R. et al. Sequential transcriptional changes dictate safe and effective antigen-specific immunotherapy. Nature Commun. 5:4741-4747, 2014.
Canadian Patent Application No. 2,817,710 Office Action dated Oct. 19, 2017.
Caruso et al., Investigation of electrostatic interactions in polyelectrolyte multilayer films: Binding of anionic fluorescent probes to layers assembled onto colloids. Macromolecules, 32(7):2317-2328, 1999.
Caruso et al., Protein multilayer formation on colloids through a stepwise self-assembly technique. J.Amer. Chem. Soc., 121(25):6039-6046, 1999.
Chen, et al., IL-2 controls the stability of Foxp3 expression in TGF-beta-induced Foxp3+ T cells in vivo. J. Immunol. 186:6329-6337, 2011.
Cirillo et al, "S1OOB protein in the gut: The evidence for enteroglial-sustained intestinal inflammation," World J Gastroenterol. 17(10):1261-1266, 2011.
Colombia Patent Application No. NC2017/0011437 Office Action dated Nov. 19, 2017.
Davies, Engineered particle surfaces. Advanced Materials, 10(15):1264-1270, 1998.
Desreumaux, P. et al. Safety and Efficacy of Antigen-Specific Regulatory T-Cell Therapy for Patients With Refractory Crohn's Disease. Gastroenterology 143:1207-1217, 2012 (Abstract only).
Edelman, Gerald M. et al. The covalent structure of an entire yGimmunoglobulin molecule. PNAS, 63(1):78-85, 1969.
Eggena et al., "Identification of Histone H1 as a Cognate Antigen of the Ulcerative Colitisassociated Marker Antibody pANCA," Journal of Autoimmunity 14:83-97, 2000.
Reijonen, H. et al. Detection of GAD65-specific T-cells by major histocompatibility complex class II tetramers in type 1 diabetic patients and at-risk subjects. Diabetes 51:1375-1382, 2002.
Ellman et al., Biosynthetic method for introducing unnatural amino acids site-specifically into proteins. Meth. Enzym. 202:301-336, 1991.
European Patent Application No. 13856460.4 Communication dated Nov. 15, 2017.
European Patent Application No. 17173410.61 extended European Search Report dated Dec. 15, 2017.
Firestein, G. S. Evolving concepts of rheumatoid arthritis. Nature 423:356-361, 2003.
Gagliani, et al. Coexpression of CD49b and LAG-3 identifies human and mouse T regulatory type 1 cells. Nat. Med. 19:739-746, 2013 (Abstract only).

(56) References Cited

OTHER PUBLICATIONS

Garboczi, et al. HLA-A2-peptide complexes: Refolding and crystallization of molecules expressed in *Escherichia coli* and complexed with single antigenic peptides. Proc Natl. Acad Sci USA 89:3429-3433, 1992.
GenBank accession No. NM_001008228.2.
GenBank accession No. NP_001008229.1.
Getts, et al. Microparticles bearing encephalitogenic peptides induce T-cell tolerance and ameliorate experimental autoimmune encephalomyelitis. Nature Biotechnol. 30:1217-1224, 2012.
Gill et al., Characterization of primary T cell subsets mediating rejection of pancreatic islet grafts. Journal of Immunology, 1989; 143(7):2176-2178.
Giuliani et al,. Additive effect of the combination of glatiramer acetate and minocycline in a model of MS. J. Neuroimmunol. 158:213-221, 2005.
Gupta et al., "Synthesis and surface engineering of iron oxide nanoparticles for biomedical applications," Biomaterials 26:3995-4021, 2005.
Hale, et al. Distinct memory CD4+ T cells with commitment to T follicular helper- and T helper 1-cell lineages are generated after acute viral infection. Immunity 38:805-817, 2013.
Hall et al., Mapping labeled sites in *Escherichia coli* ribosomal RNA: Distribution of methyl groups and identification of a a photoaffinity-labeled RNA region putatively at the Peptidyltransferase center. Biochemistry 24:5702-5711, 1985.
Hanprasopwattana, Titania coatings on monodisperse silica spheres (Characterization using 2-propanol dehydration and TEM). Langmuir, 12:3173-3179, 1996.
Holgate et al., "Treatment strategies for allergy and asthma," Nature 8:218-230, 2008.
Holst, J. et al. Generation of T-cell receptor retrogenic mice. Nat. Protoc. 1:406-417, 2006.
Israel Patent Application No. 249165 Office Action dated Dec. 17, 2017.
Japanese Patent Application No. 2016-159414 Office Action dated Oct. 30, 2017.
Jokerst et al., Nanoparticle PEGylation for imaging and therapy. Nanomedicine, 6(4):715-728, 2011.
Kamanaka, M. et al. Expression of interleukin-10 in intestinal lymphocytes detected by an interleukin-10 reporter knockin tiger mouse. Immunity 25:941-952 , 2006.
Komatsu, N. et al. Heterogeneity of natural Foxp3+ T cells: a committed regulatory T-cell lineage and an uncommitted minor population retaining plasticity. Proc. Natl. Acad. Sci. U.S.A. 106:1903-1908, 2009.
Komatsu, N. et al. Pathogenic conversion of Foxp3+ T cells into TH17 cells in autoimmune arthritis. Nat. Med. 20:62-68, 2014.
Krishnamoorthy et al., "Myelin-specific T cells also recognize neuronal autoantigen in a transgenic mouse model of multiple sclerosis," Nature Medicine 15(6):626-633, 2009.
Kulmala, P. "Prediabetes in Children," Pediatr Drugs, 5(4):211-221, 2003.
Leavenworth et al., Amelioration of arthritis through mobilization of peptide-specific CD8+ regulatory T cells. J. Clin. Invest. 123:1382-1389, 2013.
Marwaha, A. K. et al. Cutting edge: Increased IL-17-secreting T cells in children with new-onset type 1 diabetes. J. Immunol. 185:3814-3818, 2010.
McClymont, S. A. et al. Plasticity of human regulatory T cells in healthy subjects and patients with type 1 diabetes. J. Immunol. 186:3918-3926, 2011.
McLarnon, A. Regulatory T-cell therapy is a safe and well-tolerated potential approach for treating refractory Crohn's disease. Nature Rev. Gastroenterol. Hepatol. 9:559, 2012.
Merchant et al., An efficient route to human bispecific IgG. Nature Biotechnology, 16:677-681, 1998.
Miyara, M. et al. Functional delineation and differentiation dynamics of human CD4+ T cells expressing the FoxP3 transcription factor. Immunity 30:899-911, 2009.

Moore et al., Tracking the recruitment of diabetogenic CD8+ T-cells to the pancreas in real time. Diabetes, 53(6):1459-1466, 2004.
Mukherjee, R. et al. Identification of CD4+ T cell-specific epitopes of islet-specific glucose-6-phosphatase catalytic subunit-related protein: A novel Beta cell autoantigen in Type 1 diabetes. J. Immunol. 174:5306-5315, 2005.
Musacchio, et al. PEG-PE micelles loaded with Paclitaxel and surface-modified by a PBR-ligand: Synergistic anticancer effect. Mol Pharm 6:468-479, 2009.
Nelson et al. "6 types of asthma and how they're treated," Mother Nature Network, mnn.com. 2015.
New Zealand Patent Application No. 706970 First Examination Report dated Nov. 8, 2017.
Noren et al. A general method for site-specific incorporation of unnatural amino acids into proteins. Science 244(4901):182-188, 1989.
Oleszak et al., "Theiler's Virus Infection: a Model for Multiple Sclerosis," Clinical Microbiology Reviews 17(1):174-207, 2004.
Onoda, T. et al. Human CD4+ central and effector memory T cells produce IL-21: effect on cytokine-driven proliferation of CD4+ T cell subsets. Int. Immunol. 19:1191-1199, 2007.
Partch and Brown, Aerosol and solution modification of particle-polymer surfaces. J. Adhesion, 67:259-276, 1998.
PCT/IB2016/000691 International Preliminary Report on Patentability dated Nov. 7, 2017.
Pekarek et al., Double-walled polymer microspheres for controlled drug release. Nature, 367:258-260, 1994.
Perrault, S.D. et al. Mediating tumor targeting efficiency of nanoparticles through design. Nano Lett, 9(5):1909-1915, 2009.
Ponder and Richards, Tertiary templates for proteins. Use of packing criteria in the enumeration of allowed sequences for different structural classes. J. Mol. Biol. 193:775-791, 1987.
Pot, C. et al. Cutting edge: IL-27 induces the transcription factor c-Maf, cytokine IL-21, and the costimulatory receptor ICOS that coordinately act together to promote differentiation of IL-10-producing TR1 cells. J. Immunol. 183:797-801, 2009.
Ransohoff et al., "Animal models of multiple sclerosis: the good, the bad and the bottom line," Nature Neuroscience 15(8): 1074-1077, 2012.
Roncarolo, et al., Clinical tolerance in allogeneic hematopoietic stem cell transplantation. Immunol. Rev. 241:145-163, 2011.
Roncarolo, et al. Interleukin-10-secreting type 1 regulatory T cells in rodents and humans. Immunol. Rev. 21:28-50, 2006.
Russia Patent Application No. 2015116509 Office Action dated Nov. 29, 2017.
Russia Patent Application No. 2014141984 second Office Action dated Nov. 23, 2017.
Sakaguchi, S. et al. Foxp3+ CD25+ CD4+ natural regulatory T cells in dominant self-tolerance and autoimmune disease. Immunol. Rev. 212:8-27, 2006.
Santamaria, P. The long and winding road to understanding and conquering type 1 diabetes. Immunity 32, 437-445, 2010.
Saraiva, M. et al. Interleukin-10 production by Th1 cells requires interleukin-12-induced STAT4 transcription factor and ERK MAP kinase activation by high antigen dose. Immunity 31, 209-219, 2009.
Sato, K. et al. Marked induction of c-Maf protein during Th17 cell differentiation and its implication in memory Th cell development. J. Biol. Chem. 286:14963-14971, 2011.
Schirle et al., "Combining computer algorithms with experimental approaches permits the rapid and accurate identification of T cell epitopes from defined antigens," J. Immunol. Methods 257:1-16, 2001.
Scott et al., "Synthesis, Characterization, and Applications of Dendrimer-Encapsulated Nanoparticles". The Journal of Physical Chemistry B (109): 692-704, 2005.
Shanke et al., Are animal models predictive for humans? Philosopy, Ethics, and Humanities in Medicine, 9:1-20, 2007.
Spensieri, F. et al. Human circulating influenza-CD4+ ICOS1+IL-21+ T cells expand after vaccination, exert helper function, and predict antibody responses. Proc. Natl. Acad. Sci. U.S.A. 110:14330-14335, 2013.

(56) References Cited

OTHER PUBLICATIONS

Stratmann, T. et al. Susceptible MHC alleles, not background genes, select an autoimmune T cell reactivity. J. Clin. Invest. 112:902-914, 2003.

Stratmann, T. et al. The I-Ag7 MHC class II molecule linked to murine diabetes is a promiscuous peptide binder. J. Immunol. 165:3214-3225, 2000.

Sukhorukov et al., Stepwise polyelectrolyte assembly on particle surfaces: a novel approach to colloid design. Polymers Adv. Tech., 9(10-11):759-767, 1998.

'T Hart et al., "Modelling of multiple sclerosis: lessons learned in a non-human primate," Lancet Neurology 3:588-597, 2004.

Tigges et al., Human herpes simplex virus (HSV)-specific CD8+ CTL clones recognize HSV-2-infected fibroblasts after treatment with IFN-gamma or when virion host shutoff functions are disabled. J. Immunol., 156(10):3901-3910, 1996.

Tsai, et al., CD8+ T-cells in autoimmune diabetes. Adv. Immunol. 100:79-124, 2008

Tufveson, et aL, "New Immunosuppressants: Testing and Development in animal models and the clinic with special reference to DSG", Immunological Reviews, 136:101-•107, 2009.

Vakil, R. et al. Effect of cholesterol on the release of amphotericin B from PEG-phospholipid micelles. Mol Pharm 5:98-104, 2008.

Van Belle, Type 1 Diabetes: Etiology, Immunology, and Therapeutic Strategies. Physiol Rev. 91:79-118, 2011.

Verdu et al., "Oral administration of antigens from intestinal flora anaerobic bacteria reduces the severity of experimental acute colitis in BALB/c mice," Clin Exp Immunol. 120:46-50, 2000.

Wang, J. et al. In situ recognition of autoantigen as an essential gatekeeper in autoimmune CD8+ T cell inflammation. Proc. Natl. Acad. Sci. U.S.A. 107: 9317-9322, 2010.

Wekerle et al., "Animal models of multiple sclerosis," Drug Discovery Today: Disease Models 3(4):359-367, 2006.

Xu and Sun, Mini Review: Monodisperse magnetic nanoparticles for biomedical applications. Polymer International 56:821-826, 2007.

Yang, J. et al. CD4+ T cells from type 1 diabetic and healthy subjects exhibit different thresholds of activation to a naturally processed proinsulin epitope. J. Autoimmun. 31:30-41, 2008.

Yang, J. et al. Islet-specific glucose-6-phosphatase catalytic subunit-related protein-reactive CD4+ T cells in human subjects. J. Immunol. 176:2781-2789, 2006.

Yang, X. P. et al. Opposing regulation of the locus encoding IL-17 through direct, reciprocal actions of STAT3 and STAT5. Nat. Immunol. 12, 247-25, 2011.

Yoshida, K. et al. Evidence for shared recognition of a peptide ligand by a diverse panel of non-obese diabetic mice-derived, islet-specific, diabetogenic T cell clones. Int. Immunol. 14, 1439-1447, 2002.

Yoshizaki, A. et al. Regulatory B cells control T-cell autoimmunity through IL-21-dependent cognate interactions. Nature 491, 264-268, 2012.

Yu, et al. Cutting edge: Single-chain trimers of MHC Class 1 molecules form stable structures that potentially stimulate antigen-specific T cells and B cells. J Immunol 168:3145-3149, 2002.

Zang, Y. C. et al. Increased CD8+ cytotoxic T cell responses to myelin basic protein in multiple sclerosis. J. Immunol. 172, 5120-5127, 2004.

Zhang et al., "HMGB1, an innate alarmin, in the pathogenesis of type 1 diabetes," Int. J. Clin. Exp. Pathol. 3(1):24-38, 2010.

Zhou, et al., Plasticity of CD4+ T cell lineage differentiation. Immunity 30:646-655, 2009.

Zhou, X. et al. Instability of the transcription factor Foxp3 leads to the generation of pathogenic memory T cells in vivo. Nat. Immunol. 10:1000-1007, 2009.

U.S. Appl. No. 15/348,959 Office Action dated Jan. 12, 2018.

30,000x
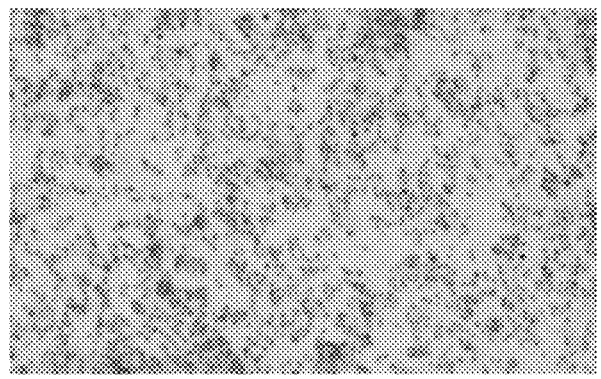
40,000x
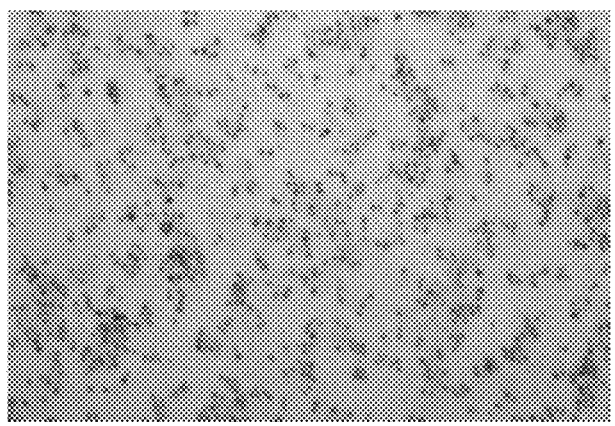
FIG. 7

30,000x
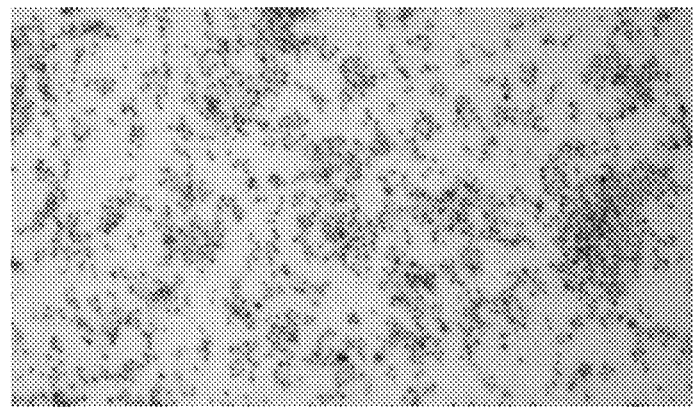
40,000x
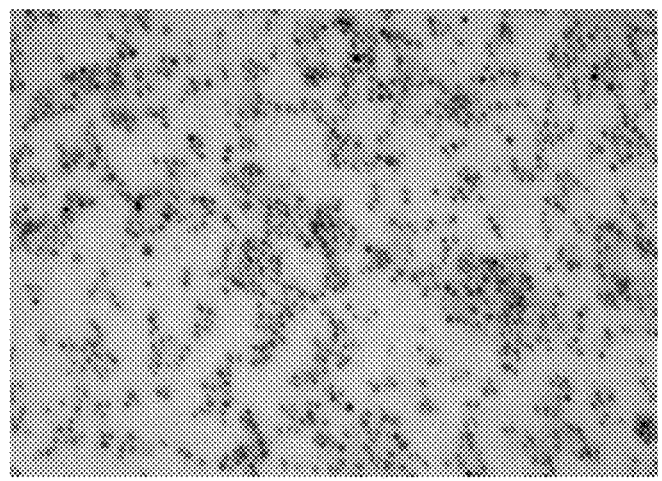
FIG. 8

Lane: 1  2  3  4  5

Lane: 1  2  3  4  5

Lane: 1 2 3 4 5 6 7

```
NcoI
            ┌─────────────────────────────────────────────────────┐
            │ M  A  I  I  Y  L  I  L  L  F  T  A  V  R  G│ D  ·
     841    │ATGGCT ATCATCTACC TCATCCTCCT GTTACCGCT GTGCGGGGCG│
            └─────────────────────────────────────────────────────┘
             TACCGA TAGTAGATGG AGTAGGAGGA CAAGTGGCGA CACGCCCCGC
   ·        V  D  E  Q  L  S  K  S  V  K  D  K  V  L  L  P  C  R  Y  N
     901    ATGTTGATGA ACAACTGTCC AAGTCAGTGA AAGATAAGGT ATTGCTGCCT TGCCGTTACA
            TACAACTACT TGTTGACAGG TTCAGTCACT TTCTATTCCA TAACGACGGA ACGGCAATGT
   ·        S  P  H  E  D  E  S  E  D  R  I  Y  W  Q  K  H  D  K  V  V
     961    ACTCTCCTCA TGAAGATGAG TCTGAAGACC GAATCTACTG GCAAAAACAT GACAAAGTGG
            TGAGAGGAGT ACTTCTACTC AGACTTCTGG CTTAGATGAC CGTTTTTGTA CTGTTTCACC
   ·        L  S  V  I  A  G  K  L  K  V  W  P  E  Y  K  N  R  T  L  Y  ·
    1021    TGCTGTCTGT CATTGCTGGG AAACTAAAAG TGTGGCCCGA GTATAAGAAC CGGACTTTAT
            ACGACAGACA GTAACGACCC TTTGATTTTC ACACCGGGCT CATATTCTTG GCCTGAAATA
   ·        D  N  T  T  Y  S  L  I  I  L  G  L  V  L  S  D  R  G  T  Y  ·
    1081    ATGACAACAC TACCTACTCT CTTATCATCC TGGGCCTGGT CCTTTCAGAC CGGGGCACAT
            TACTGTTGTG ATGGATGAGA GAATAGTAGG ACCCGGACCA GGAAAGTCTG GCCCCGTGTA
   ·        S  C  V  V  Q  K  E  R  G  T  Y  E  V  K  H  L  A  L  V  ·
    1141    ACAGCTGTGT CGTTCAAAAG AAGGAAAGAG GAACGTATGA AGTTAAACAC TTGGCTTTAG
            TGTCGACACA GCAAGTTTTC TTCCTTTCTC CTTGCATACT TCAATTTGTG AACCGAAATC
   ·        K  L  S  I  K  A  D  F  S  T  P  N  I  T  E  S  G  N  P  S  ·
    1201    TAAAGTTGTC CATCAAAGCT GACTTCTCTA CCCCCAACAT AACTGAGTCT GGAAACCCAT
            ATTTCAACAG GTAGTTTCGA CTGAAGAGAT GGGGGTTGTA TTGACTCAGA CCTTTGGGTA
            PstI
            ~~~~~~
   ·        A  D  T  K  R  I  T  C  F  A  S  G  G  F  P  K  P  R  F  S  ·
    1261    CTGCAGACAC TAAAAGGATT ACCTGCTTTG CTTCCGGGGG TTTCCCAAAG CCTCGCTTCT
            GACGTCTGTG ATTTTCCTAA TGGACGAAAC GAAGGCCCCC AAAGGGTTTC GGAGCGAAGA
                                                                BamHI
                                                                ~~~~~~
   ·        W  L  E  N  G  R  E  L  P  G  I  N  T  T  I  S  Q  D  P  E  ·
    1321    CTTGGTTGGA AAATGGAAGA GAATTACCTG GCATCAATAC GACAATTTCC CAGGATCCTG
            GAACCAACCT TTTACCTTCT CTTAATGGAC CGTAGTTATG CTGTTAAAGG GTCCTAGGAC
   ·        S  E  L  Y  T  I  S  S  Q  L  D  F  N  T  T  R  N  H  T  I  ·
    1381    AATCTGAATT GTACACCATT AGTAGCCAAC TAGATTTCAA TACGACTCGC AACCACACCA
            TTAGACTTAA CATGTGGTAA TCATCGGTTG ATCTAAAGTT ATGCTGAGCG TTGGTGTGGT
   ·        K  C  L  I  K  Y  G  D  A  H  V  S  E  D  F  T  W  E  K  P  ·
    1441    TTAAGTGTCT CATTAAATAT GGAGATGCTC ACGTGTCAGA GGACTTCACC TGGGAAAAAC
            AATTCACAGA GTAATTTATA CCTCTACGAG TGCACAGTCT CCTGAAGTGG ACCCTTTTTG
```

FIG. 11A

```
             P   E   D   P   P   D   S   K   D   K   T   H   T   C   P   P   C   P   A   P
     1501    CCCCAGAAGA CCCTCCTGAT AGCAAGGACA AAACTCACAC ATGCCCACCG TGCCCAGCAC
             GGGGTCTTCT GGGAGGACTA TCGTTCCTGT TTTGAGTGTG TACGGGTGGC ACGGGTCGTG
             E   A*  A*  G   G   P   S   V   F   L   F   P   P   K   P   K   D   T   L   M
     1561    CTGAAGCCGC GGGGGGACCG TCAGTCTTCC TCTTCCCCCC AAAACCCAAG GACACCCTCA
             GACTTCGGCG CCCCCCTGGC AGTCAGAAGG AGAAGGGGGG TTTTGGGTTC CTGTGGGAGT
             I   S   R   T   P   E   V   T   C   V   V   V   D   V   S   H   E   D   P   E
     1621    TGATCTCCCG GACCCCTGAG GTCACATGCG TGGTGGTGGA CGTGAGCCAC GAAGACCCTG
             ACTAGAGGGC CTGGGGACTC CAGTGTACGC ACCACCACCT GCACTCGGTG CTTCTGGGAC
             V   K   F   N   W   Y   V   D   G   V   E   V   H   N   A   K   T   K   P   R
     1681    AGGTCAAGTT CAACTGGTAC GTGGACGGCG TGGAGGTGCA TAATGCCAAG ACAAAGCCGC
             TCCAGTTCAA GTTGACCATG CACCTGCCGC ACCTCCACGT ATTACGGTTC TGTTTCGGCG
             E   E   Q   Y   N   S   T   Y   R   V   V   S   V   L   T   V   L   H   Q   D
     1741    GGGAGGAGCA GTACAACAGC ACGTACCGTG TGGTCAGCGT CCTCACCGTC CTGCACCAGG
             CCCTCCTCGT CATGTTGTCG TGCATGGCAC ACCAGTCGCA GGAGTGGCAG GACGTGGTCC
             W   L   N   G   K   E   Y   K   C   K   V   S   N   K   A   L   P   A   P   I
     1801    ACTGGCTGAA TGGCAAGGAG TACAAGTGCA AGGTCTCCAA CAAAGCCCTC CCAGCCCCCA
             TGACCGACTT ACCGTTCCTC ATGTTCACGT TCCAGAGGTT GTTTCGGGAG GGTCGGGGGT
             E   K   T   I   S   K   A   K   G   Q   P   R   E   P   Q   V   Y   T   L   P
     1861    TCGAGAAAAC CATCTCCAAA GCCAAAGGGC AGCCCCGAGA ACCACAGGTG TACACCCTGC
             AGCTCTTTTG GTAGAGGTTT CGGTTTCCCG TCGGGGCTCT TGGTGTCCAC ATGTGGGACG
                SmaI
                ~~~~~~
             P   S   R   D   E   L   T   K   N   Q   V   S   L   T   C   L   V   K   G   F
     1921    CCCCATCCCG GGATGAGCTG ACCAAGAACC AGGTCAGCCT GACCTGCCTG GTCAAAGGCT
             GGGGTAGGGC CCTACTCGAC TGGTTCTTGG TCCAGTCGGA CTGGACGGAC CAGTTTCCGA
             Y   P   S   D   I   A   V   E   W   E   S   N   G   Q   P   E   N   N   Y   K
     1981    TCTATCCCAG CGACATCGCC GTGGAGTGGG AGAGCAATGG GCAGCCGGAG AACAACTACA
             AGATAGGGTC GCTGTAGCGG CACCTCACCC TCTCGTTACC CGTCGGCCTC TTGTTGATGT
             T   T   P   P   V   L   D   S   D   G   S   F   F   L   Y   S   K   L   T   V
     2041    AGACCACGCC TCCCGTGTTG GACTCCGACG GCTCCTTCTT CCTCTACAGC AAGCTCACCG
             TCTGGTGCGG AGGGCACAAC CTGAGGCTGC CGAGGAAGAA GGAGATGTCG TTCGAGTGGC
             D   K   S   R   W   Q   Q   G   N   V   F   S   C   S   V   M   H   E   A   L
     2101    TGGACAAGAG CAGGTGGCAG CAGGGGAACG TCTTCTCATG CTCCGTGATG CATGAGGCTC
             ACCTGTTCTC GTCCACCGTC GTCCCCTTGC AGAAGAGTAC GAGGCACTAC GTACTCCGAG
             H   N   H   Y   T   Q   K   S   L   S   L   S   P   G   K   G   S   G   S   G
     2161    TGCACAACCA CTACACGCAG AAGAGCCTCT CCCTGTCTCC GGGTAAAGGT AGTGGTAGTG
             ACGTGTTGGT GATGTGCGTC TTCTCGGAGA GGGACAGAGG CCCATTTCCA TCACCATCAC
             S   G   S   L   G   G   I   F   E   A   M   K   M   E   L   R   D   *
     2221    GTAGTGGATC TCTGGGTGGT ATCTTCGAGG CTATGAAGAT GGAGCTGCGC GATTGA
             CATCACCTAG AGACCCACCA TAGAAGCTCC GATACTTCTA CCTCGACGCG CTAACT
```

FIG. 11B

COMPOSITIONS AND METHODS FOR THE PREVENTION AND TREATMENT OF CANCER

CROSS-REFERENCE TO RELATED APPLICATIONS

This application is a continuation of U.S. application Ser. No. 13/294,109, filed Nov. 10, 2011, which claims priority under 35 U.S.C. § 119(e) to U.S. Provisional Application No. 61/413,330, filed Nov. 12, 2010, the content of each of which is incorporated herein by reference in its entirety.

FIELD OF THE INVENTION

This invention is directed to compositions and methods related to immunotherapy and medicine. In particular, this invention is related to therapeutics for the prevention and treatment of cancer.

BACKGROUND

Cancer immunology is an emerging field in the area of cancer therapeutics that aims to utilize the body's own immune defenses to target and eliminate cancerous cells. The idea of using the body's own immune system to attack cancer cells has many advantages over traditional therapies that are site specific, such as radiation and surgery, or over chemotherapeutic methods that are associated with detrimental side-effects and high toxicity.

This field was significantly advanced by the identification and characterization of many different tumor-specific antigens. These tumor-specific antigens are specific to the cancerous cells themselves. If an immune response could be launched that targets these tumorspecific antigens, the body would effectively be able to clear cancerous cells on its own. However, strategies to induce tumor-specific immunity in patients have thus far been unsuccessful. Studies suggest that there are various factors that contribute to the failure of current cancer immunotherapeutic strategies. First, these strategies fail to sufficiently expand circulating cytotoxic T cell lymphocytes. Second, cancer patients are often immunosuppressed and fail to produce the co-stimulatory molecules necessary to initiate an immune response. Therefore, a major goal of cancer immunotherapy has been to generate a large number of high-avidity tumor-specific T cells that can efficiently attack cancerous cells in vivo.

The present invention uses a nanoparticle coated with tumor-specific antigen/MHC complexes and co-stimulatory molecules. This unique complex can induce an expansion of circulating CD8+ T cells in an amount that surpasses that of current cancer immunotherapies.

SUMMARY

Conventional cancer immunotherapy falls short at efficiently expanding T cells that specifically target cancerous cells in numbers sufficient to significantly reduce the tumor size. It is contemplated that nanosize particles coated with MHC class I and/or class II molecules presenting tumor-specific antigens and co-stimulatory molecules capable of activating naïve Tcells that led to a massive expansion of antigen-specific anti-tumorigenic T cells capable of differentiating into cytotoxic T cells, effector T cells, memory T cells, and helper T cells that are necessary to initiate and maintain a substantial immune response against cancerous, precancerous, or neoplastic cells in vivo. The present invention describes a systemic approach to targeting cancerous, pre-cancerous or neoplastic cells that are circulating cells, as in lymphomas, migratory metastatic cells, and solid tumors. This is in stark contrast to therapies that are site-specific such as radiation, surgery, and biopsy.

Aspects and embodiments of this technology include a novel method for preventing or treating tumors and cancer comprising administering to a subject an antigen/MHC/co-stimulatory molecule complex operatively coupled to a nanoparticle in an amount sufficient to expand anti-tumorigenic T cells. Traditionally, immunotherapies targeting tumors and cancer have been unsuccessful at expanding T cells in numbers sufficient to effectively treat patients with cancerous cells and/or tumors. Aspects of the present invention relate to novel complexes that, unexpectedly, are capable of expanding anti-tumorigenic T cell populations at levels not traditionally attained with other immunotherapies.

Certain embodiments of the present invention relate to a method of inhibiting the growth of tumors, and preventing or treating cancer comprising administering to a subject an antigen/MHC/co-stimulatory molecule complex operatively coupled to a nanoparticle to a subject in an amount sufficient to expand anti-tumorigenic T cells, wherein the method further comprises administering the antigen/MHC/nanoparticle complexes in an amount sufficient to activate and/or expand pre-existing anti-tumorigenic memory cells. It is contemplated that administration of antigen/MHC/co-stimulatory molecule/nanoparticle complexes to a patient will differentiate naïve T cells into different types of antigen-specific anti-tumorigenic T cell populations. As such, one of these populations will be antigen-specific anti-tumorigenic memory T cells. It is further contemplated that subsequent administration of antigen/MHC/nanoparticle complexes without co-stimulatory molecules can activate said antigen-specific anti-tumorigenic memory cells.

In a further aspect, this disclosure provides a method to activate antigen-specific anti-tumorigenic memory cells in a patient in need of such by administering an effective amount of an antigen/MHC/co-stimulatory molecule complex operatively coupled to a nanoparticle.

In yet a further embodiment, the invention includes methods for diagnosing cancer comprising assessing treatment-induced expansion of anti-tumorigenic CD8+ or CD4+ T cell responses as an indication of active immunity.

Another aspect relates to a method for inhibiting the metastasis of a cancer in a patient which method comprises administering to a subject an antigen/MHC/co-stimulatory molecule complex operatively coupled to a nanoparticle to a subject in an amount sufficient to expand the population of antigen-specific anti-tumorigenic T cells wherein said expanded population is sufficient to treat said cancer wherein said antigen is specific to said tumor wherein said administration provides for systemic circulation of the complex in said patient.

Further embodiments of the invention include methods of expanding antigen-specific anti-tumorigenic T cells comprising administering to a subject or to cells in vitro an antigen/MHC/co-stimulatory molecule/nanoparticle complex in an amount sufficient to stimulate expansion of an antigen-specific anti-tumorigenic T cell. In certain aspects the T cell is a CD8+ or a CD4+ T cell or a NKT cell. In other aspects of the invention, the T cell is a CD8+ or CD4+ memory T cell. In still further aspects of the invention, the T cell is a CD8+ cytotoxic T cell or a CD4+ helper T cell.

Certain embodiments of the present invention relate to methods of selectively expanding and/or developing populations of antigen-specific anti-tumorigenic T cells in a subject which method comprises administering to said subject an antigen/MHC/co-stimulatory molecule/nanoparticle complex wherein said complex is administered in an amount and frequency sufficient to expand said populations. Therefore, the present invention can initiate and maintain an immune response that reduces or eliminates developing cancerous and pre-cancerous cells in vivo. As such, the present invention can expand desirable T cells, such as T cells that recognize tumor antigens, to prevent, treat and/or ameliorate diseases associated with developing tumors.

The present invention is directed to targeting cells in the body in an antigen-specific way. Tumor-specific antigens are well-known in the art and are described in various references, for example, by Dranoff, G. ("Targets of Protective Tumor Immunity." (2009) Cancer Vaccines: Ann. N.Y. Acad. Sci. 1174:74-80), and U.S. Pat. Nos. 7,795,224, 7,812,116, 7,785,801 which are herein incorporated by reference. The technology is not limited to certain antigens, and techniques for identifying tumor-specific antigens are well known in the art and have been previously described, for example, by Schlichtholz et al. ("The immune response to p53 in breast cancer patients is directed against immunodominant epitopes unrelated to the mutational hot spot." Cancer Res 1992; 52:6380-4), De Plaen, E. et al. ("Immunogenic (tum-) variants of mouse tumor P815: cloning of the gene of tum-antigen P91A and identification of the tum-mutation." Proc Natl Acad Sci USA 1988; 85:2274-8), and Sahin, U. et al. ("Human neoplasms elicit multiple specific immune responses in the autologous host." Proc Natl Acad Sci USA 1995; 92:11810-3) which are herein incorporated by reference. Thus, without being bound by theory, this technology initiates an immune response against any cells in the body that are characterized as having a specific antigen. As such, the present invention is not limited to a specific antigen sequence, but can be directed to any antigen sequence that is found to be unique to a diseased cell in the body.

Embodiments of the invention are directed to methods of diagnosing, preventing, or treating tumor development comprising administering an antigen/MHC/co-stimulatory molecule/nanoparticle complex to a subject in an amount sufficient to expand antigen-specific anti-tumorigenic T cells. In general and as used herein, the term "an antigen" includes, but is not limited to all or part of a peptide, nucleic acid, carbohydrate, lipid or other molecule or compound that can modulate the activity of T cells or T cell populations, when in the context of a MHC or MHC-like molecule coupled to a substrate. In some aspects of this invention, the nanoparticle is bioabsorbable so that it prevents long term accumulation of the nanoparticles in vivo without any accompanying toxicity arising therefrom.

Embodiments of the invention for use in the disclosed methods include particles comprising a nanoparticle coupled to an antigen/MHC/co-stimulatory molecule complex. The antigen/MHC/co-stimulatory molecule complex can be coupled directly to such a nanoparticle or via a linker. A nanoparticle can comprise various layers which in turn can comprise multiple components (e.g., a metal core with a covering or a shell of other molecules that can be more easily coupled to the antigen/MHC/co-stimulatory molecule complex such as streptavidin or avidin or other know molecules used to attach moieties to nanoparticles). In certain aspects, a nanoparticle comprises one or more of a material selected from the group consisting of, for example, cadmium selenide, titanium, titanium dioxide, tin, tin oxide, silicon, silicon dioxide, iron, iron III oxide, silver, nickel, gold, copper, aluminum, steel, cobalt-chrome alloy, titanium alloy, brushite, tricalcium phosphate, alumina, silica, zirconia, diamond, polystyrene, silicone, rubber, polycarbonate, polyurethanes, polypropylenes, polymethylmethaacrylate, polyvinyl chloride, polyesters, polyethers, and polyethylene, tricalcium phosphate, chromium, gallium, as well as biocompatible, bioabsorbable polymers such as PGLA, PLLA, PGA, PDLLA, PCL, PDLGA, PLDLA, PLC (all of which are available from Zeus, 3737 Industrial Blvd, Orangeburg, S.C., 29118 USA under the tradename Absorv™), hylaurinic acid, alginate, polyhydroxyalkanoates, and the like. In further aspects, a biocompatible bioabsorbable nanoparticle comprises one or more of a metal or magnetizable or superparamagnetic nanoparticle. The biocompatible, bioabsorbable nanoparticle can further comprise one or more of a biodegradable coating formed from dextran; poly(ethylene glycol); poly(ethylene oxide); mannitol; poly(hydroxalkanoate)s of the PHB-PHV class; and other modified poly (saccharides) such as starch, cellulose and chitosan.

Certain aspects of the invention include methods and compositions comprising antigenic compositions, which in turn comprise one or more of segments, fragments, or epitopes of polypeptides, peptides, nucleic acids, carbohydrates, lipids and other molecules that provoke or induce an antigenic or immune response, generally referred to as antigens.

In certain aspects the antigen/MHC complex and the co-stimulatory molecule can be crosslinked (conjugated) to the nanoparticles described herein using methods known to those skilled in the art. One non-limiting example of such a method of conjugating a nanoparticle to an antigen/MHC complex and co-stimulatory molecule includes (a) reacting an antigen/MHC complex and co-stimulatory molecule with a conjugating agent, thereby forming an antigen/MHC/co-stimulatory molecule complex; and (b) reacting a nanoparticle to the complex of step (a). Another non-limiting example of such a method of conjugating a nanoparticle to an antigen/MHC complex and co-stimulatory molecule includes (a) reacting an antigen/MHC complex and a co-stimulatory molecule with a conjugating agent separately, thereby forming an antigen/MHC complex and a co-stimulatory molecule complex; and (b) reacting a nanoparticle to the complexes of step (a) such that the antigen/MHC complex and the co-stimulatory molecule are separately tethered to the nanoparticle. In one embodiment, the method comprises concentrating the complex of step (a) before performing step (b). In another embodiment, the conjugating agent comprises a heterobifunctional agent. In yet another embodiment, the conjugating agent comprises DOTA-maleimide (4-maleimidobutyramidobenzyl-DOTA), SMPT (4-succinimidyloxycarbonyl-α-methyl-α-(2-pyridylditio) toluene-), sulfo-LC-SMPT (sulfosuccinimidyl-6-(α-methyl-α-(2-pyridylthio)toluamido) hexanoate, Traut's reagent (2-Iminothiolane-HCl), or any combination thereof. See U.S. Patent Publication Nos. 20070059775; U.S. Pat. Nos. 4,671,958, 4,659,839, 4,414,148, 4,699,784; 4,680,338; 4,569,789; 4,589,071; 7,186,814 and 5,543,391 European Patent Application No. 188,256 for a discussion of conjugating complexes to microparticles or nanoparticles, the disclosure of which are incorporated herein by reference.

In certain embodiments the antigen/MHC/co-stimulatory molecule complex is made by first crosslinking the co-stimulatory molecule to a nanoparticle. In this case, the disclosure also provides the intermediate that comprises a nanoparticle and a co-stimulatory molecule coupled to said nanoparticle.

The cancers, pre-cancerous, tumors and/or neoplastic conditions treated by the methods and compositions of this disclosure are not limited to any specific cell or tumor type or specific cancer but include any such (e.g., cancer) in which a tumor-specific antigen is present in the cells, such as the cancerous cells. In certain aspects, a peptide component of an antigen/MHC/co-stimulatory molecule/nanoparticle complex is derived or designed from an antigen or an antigen epitope, or a mimic thereof that is expressed in or present in tumors, cancerous, pre-cancerous or neoplastic cells. Various such proteins or epitopes have been identified for a variety of cancers.

In still further aspects of this invention, the MHC component of the antigen/MHC/co-stimulatory molecule/nanoparticle complex is a classical or non-classical MHC class I or MHC class II polypeptide component. The MHC class I component can comprise all or part of a HLA-A, HLA-B, HLA-C, HLA-E, HLA-F, HLA-G molecule, particularly all or part of a HLA-A molecule, such as a HLA-A*0201 MHC class I molecule. The non-classical MHC class I component can comprise CD1-like molecules. An MHC class II component can comprise all or part of a HLA-DR, HLA-DQ, or HLA-DP. In certain aspects, the antigen/MHC/co-stimulatory molecule complex is covalently or non-covalently coupled or attached to a substrate (antigen/MHC/co-stimulatory molecule/nanoparticle complex).

Co-stimulatory molecules are molecules that produce a secondary signal in vivo that serves to activate naïve T cells into antigen-specific T cells capable of producing an immune response to cells possessing said specific antigen. Various co-stimulatory molecules are well-known in the art, and the present invention is not limited to one specific co-stimulatory molecule. Some examples of co-stimulatory molecules are B7.1, 4-IBBL, CD40, IL-15/IL-15Ra, CD28, CD80, CD86, and ICOS. In some embodiments, only one specific co-stimulatory molecule is coupled to a nanoparticle. In another embodiment, a variety of different co-stimulatory molecules are coupled to the same nanoparticle. In certain embodiments the co-stimulatory molecule is a protein such as an antibody that is capable of agonizing a co-stimulatory receptor on a T cell. In this case, the antibody is capable of inducing a co-stimulatory signal that is necessary to activate naïve T cells and induce an immune response in an antigen-specific manner.

The substrate is typically a nanoparticle. One critical aspect of the instant invention is the nanosize nanoparticle. In one embodiment the nanoparticle is about 1 nm to about 100 nm in diameter. Preferably, the nanoparticle is about 5 nm to about 15 nm in diameter. In another embodiment the diameter of the nanoparticle is about 5 to about 25 nm, or about 1 nm to about 50 nm, or about 2 to about 25, or about 1 nm to about 10 nm, or about 10 nm to about 20 nm or about 1 nm to about 30 nm. In one embodiment, the nanoparticle comprises a metal, such as iron or iron oxide. In another embodiment, the nanoparticle comprises a biocompatible, bioabsorbable polymer. In certain embodiments, the nanoparticle undergoes bioabsorption in vivo such that accumulation of the nanoparticles in vivo is limited. Peptides of the invention can be chemically coupled to a substrate and in particular coupled via a chemical or a peptide linker. CD1 molecules are an example of a non-classical MHC molecule. Non-classical MHC molecules are characterized as non-polymorphic, conserved among species and possessing narrow, deep, hydrophobic ligand binding pockets. These binding pockets are capable of presenting glycolipids and phospholipids to Natural Killer T (NKT) cells. NKT cells represent a unique lymphocyte population that co-express NK cell markers and a semi-invariant T cell receptor (TCR). They are implicated in the regulation of immune responses associated with a broad range of diseases.

In certain aspects, the antigen/MHC/co-stimulatory molecule/nanoparticle complex need not be administered with an adjuvant in order to induce an immune response, e.g., an antibody response. In particular embodiments, the antigen/MHC/co-stimulatory molecule/nanoparticle composition can be used in conjunction with other therapeutic techniques that induce an antibody response directed to the cancerous cells.

DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 7 shows 30,000× and 40,000× magnification of pMHC conjugated Fe$_3$O$_4$ nanoparticles (IGRP/anti-CD28-SFPE-080411) in PBS. Iron Nanoparticles (SFPE-072611) have a core size of 9.4 nm. The pMHC concentration is 380 µg/mL as measured by Dot ELISA. The anti-CD28 concentration is 124 µg/mL as measured by Dot ELISA. The Fe concentration is 700 ug/mL ($3.5 \times 10^{14}$ pMHC-FeNPs/mL).

The pMHC valence is 13 pMHCs/NP as measured by Dot-ELISA. The Anti-CD28 Valence is 1.4 IgG/NP as measured by dot-ELISA.

FIG. 8 shows 30,000× and 40,000× magnification of pMHC conjugated $Fe_3O_4$ nanoparticles (IGRP-SFPE-080411) in PBS. Iron Nanoparticles (SFPE-072611) have a core size of 9.4 nm. The pMHC concentration is 340 µg/mL as measured by Dot ELISA. The Fe concentration is 500 ug/mL ($2.5×10^{14}$ pMHC-FeNPs/mL). The pMHC valence is 16 pMHCs/NP as measured by Dot-ELISA.

Figure 9A:
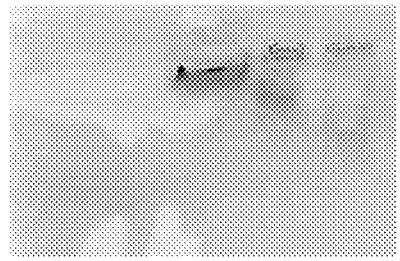
Figure 9B:
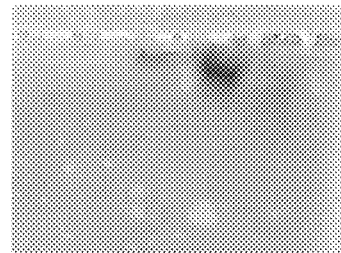
Figure 9C:
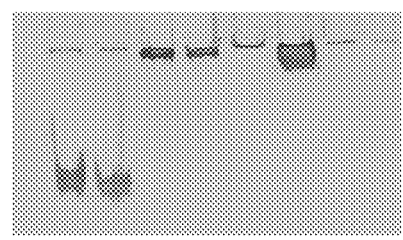

FIGS. 9A-9C show agarose and native gel analysis of pMHC conjugated SFPE Nanoparticles. Shown in FIGS. 9A and 9B are agarose gels before coomassie blue staining (FIG. 9A) and after coomassie blue staining (FIG. 9B) loaded in lanes 1-5 with: 4 µg of pMHC (lane 1), 2 µg of pMHC (lane 2), 10 µl of SFPE-080311 (lane 3), 20 µl pMHC/anti-CD28-SFPE-080411 (lane 4), and 20 µl of pMHC-SFPE-080411 (lane 5). FIG. 9C depicts a native gel loaded with 4 µg of pMHC (lane 1), 2 µg of pMHC (lane 2), 4 µg of anti-CD28 (lane 3), 2 µg of anti-CD28 (lane 4), 18 µl of pMHC-SFPE-080411 (lane 5), 18 µl pMHC/anti-CD28-SFPE-0080411 (lane 6), and 10 µl of SFPE-080311 (lane 7).

Figure 10A:
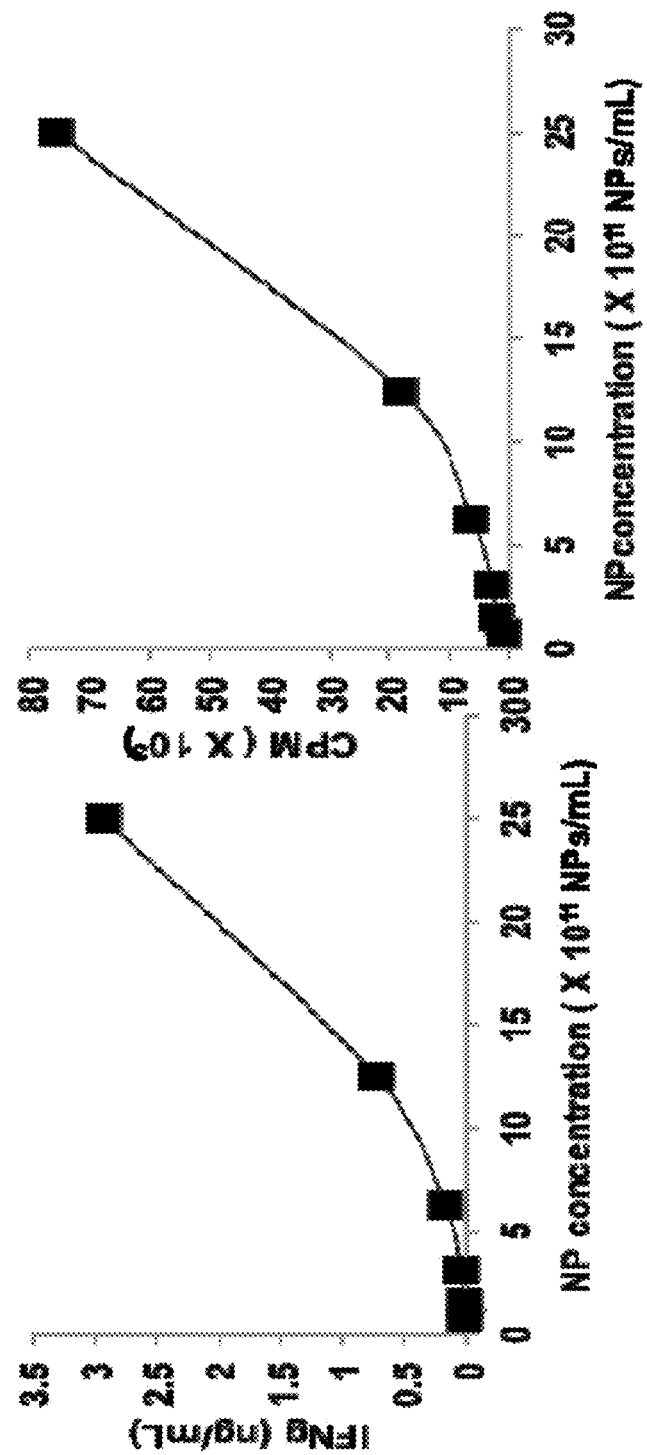
Figure 10B:
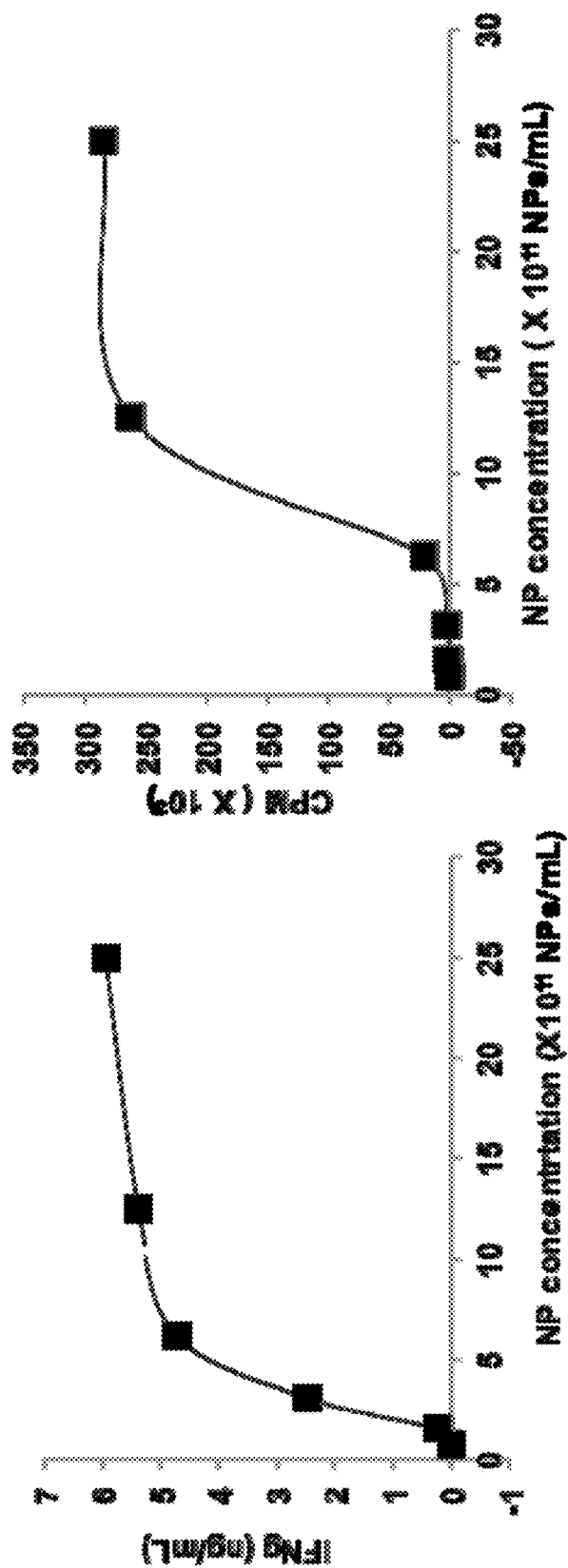

FIGS. 10A-10B show IFN-γ and proliferative responses of 8.3 cells to pMHC conjugated SFPE-NPs. FIG. 10A depicts the IFN-γ (IFNg, left panel) and proliferative response (CPM, right panel) of pMHC-SFPE-080411. FIG. 10B depicts the IFN-γ (IFNg, left panel) and proliferative response (CPM, right panel) of pMHC/anti-CD28-SFPE-080411.

FIGS. 11A-11B show the protein (SEQ ID NO: 105) and DNA (SEQ ID NO: 104) sequences of the mB7.1-hFcAA construct. The sequences of individual components in the fusion protein are highlighted in the following manner: the HA leader protein sequence is in a white box, the mB7.1 protein sequence is underlined, the hFcAA fragment protein sequence is shaded grey, the BirA biotinylation protein sequence is boxed with diagonal lines, and the mutated FcR binding site (LL to AA) within the CH2 region is labeled with asterisks (A* A*).

Figure 12:
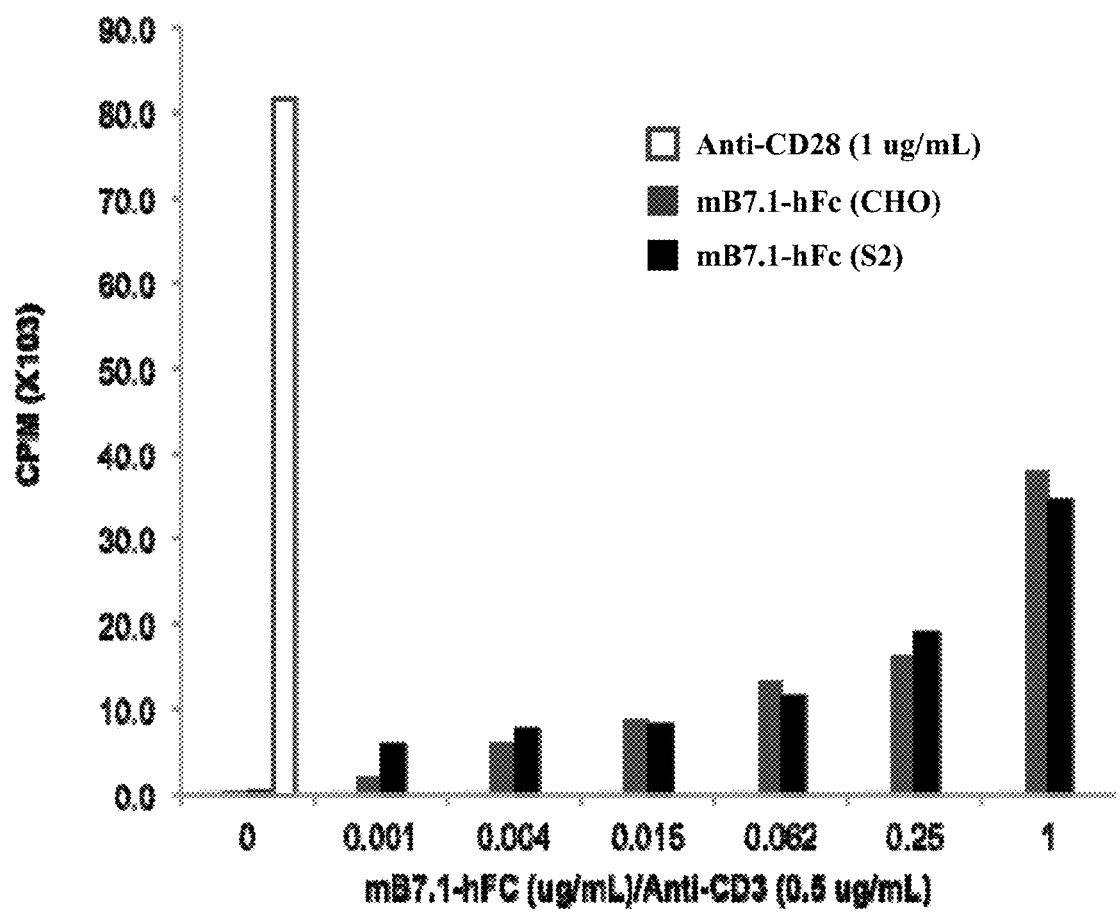

FIG. 12 shows the proliferative responses of CD4+ T cells to mB7.1-hFc fusion protein in the presence of a suboptimal concentration of anti-CD3 (0.5 ug/mL). This figure demonstrates that the mB7.1-hFc fusion protein as designed can effectively deliver a co-stimulatory signal to TCR-stimulated T-cells.

DETAILED DESCRIPTION

It is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

It must be noted that as used herein and in the appended claims, the singular forms "a", "an", and "the" include plural referents unless the context clearly dictates otherwise. Thus, for example, reference to "an excipient" includes a plurality of excipients.

I. Definitions

Unless defined otherwise, all technical and scientific terms used herein have the same meaning as commonly understood by one of ordinary skill in the art to which this invention belongs. As used herein the following terms have the following meanings.

As used herein, the term "comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) of the claimed invention. "Consisting of" shall mean excluding more than trace elements of other ingredients and substantial method steps. Embodiments defined by each of these transition terms are within the scope of this invention.

By "biocompatible", it is meant that the components of the delivery system will not cause tissue injury or injury to the human biological system. To impart biocompatibility, polymers and excipients that have had history of safe use in humans or with GRAS (Generally Accepted As Safe) status, will be used preferentially. By biocompatibility, it is meant that the ingredients and excipients used in the composition will ultimately be "bioabsorbed" or cleared by the body with no adverse effects to the body. For a composition to be biocompatible, and be regarded as non-toxic, it must not cause toxicity to cells. Similarly, the term "bioabsorbable" refers to nanoparticles made from materials which undergo bioabsorption in vivo over a period of time such that long term accumulation of the material in the patient is avoided. In a preferred embodiment, the biocompatible nanoparticle is bioabsorbed over a period of less than 2 years, preferably less than 1 year and even more preferably less than 6 months. The rate of bioabsorption is related to the size of the particle, the material used, and other factors well recognized by the skilled artisan. A mixture of bioabsorbable, biocompatible materials can be used to form the nanoparticles used in this invention. In one embodiment, iron (III) oxide and a biocompatible, bioabsorbable polymer can be combined. For example, iron (III) oxide and PGLA can be combined to form a nanoparticle An antigen/MHC/co-stimulatory molecule/nanoparticle complex refers to presentation of a peptide, carbohydrate, lipid, or other antigenic segment, fragment, or epitope of an antigenic molecule or protein on a surface, such as a nanoparticle. "Antigen" as used herein refers to all, part, fragment, or segment of a molecule that can induce an immune response in a subject or an expansion of antigen-specific anti-tumorigenic T cells.

The term "co-stimulatory molecule" as used herein refers to a molecule that can produce a co-stimulation signal that activates a naïve T cell. Full activation of naïve T cells require at least two signals. The first signal is provided by the antigen displayed by antigen presenting cells bound to the MHC complex. The second signal is the co-stimulatory signal. This signal is an agonistic signal directed to co-stimulatory receptors on T cells. T cell co-stimulation is a critical component for T cell proliferation, differentiation and survival. The present inventions encompasses molecules capable of producing a co-stimulatory signal. As such, the present invention is not limited to a specific co-stimulatory molecule. In some instances the co-stimulatory molecule is an antibody capable of agonizing the co-stimulatory receptor on the T cell.

The term "about" when used before a numerical designation, e.g., temperature, time, amount, and concentration, including range, indicates approximations which may vary by (+) or (−) 10%, 5%, or 1%.

By "killing" or "kills" it is meant to cause cell death by apoptosis or necrosis. Apoptosis or necrosis can be mediated by any cell death pathway.

"Immune cells" include, for example, adult splenocytes, T lymphocytes, B lymphocytes, and cells of bone marrow origin, such as defective antigen presenting cells of a mammal, that have activity towards the organism from which the immune cell is derived.

A "mimic" is an analog of a given ligand or peptide, wherein the analog is substantially similar to the ligand. "Substantially similar" means that the analog has a binding profile similar to the ligand except the mimic has one or more functional groups or modifications that collectively accounts for less than about 50%, less than about 40%, less than about 30%, less than about 20%, less than about 10%, or less than about 5% of the molecular weight of the ligand.

An "effective amount" is an amount sufficient to achieve the intended purpose, e.g., modulation of T cell activity or T cell populations. As described herein in detail, the effective amount, or dosage, and frequency of administration depends on the purpose and the antigen and can be determined according to the present disclosure.

An "antigen-specific anti-tumorigenic T cell" or "anti-tumorigenic T cell" is a T cell that is involved in the immune response directed to the treatment of disease due to cancerous cells, pre-cancerous cells, neoplastic cells, or developing tumors. It is contemplated that administering tumor-specific antigens covalently bound to MHC/co-stimulatory molecule/nanoparticle complexes to patients suffering from or at risk of suffering from a developing tumor will differentiate naïve T cells into T cells capable of undergoing an immune response that targets cancerous cells possessing said tumor-specific antigen. Such cancerous cells need not be in the form of a solid tumor, but can also be circulating in the blood, as in cancerous lymphatic cells, or migrating through the body, as in the case of metastatic cells. Specific anti-tumorigenic T cells expanded by this method include but are not limited to anti-tumorigenic memory $CD4^+$ and $CD8^+$ T cells, anti-tumorigenic cytotoxic $CD8^+$ T cells, and anti-tumorigenic $CD4^+$ T helper cells.

The terms "inhibiting," "reducing," or "prevention," or any variation of these terms, when used in the claims and/or the specification includes any measurable decrease or complete inhibition to achieve a desired result. The term preventing as it relates to cancer intends a prevention of the progression from a pre-cancerous state to a cancerous state.

The term "cancerous cell" refers to a cell that exhibits one or more characteristics or hallmarks of cancer. Such hallmarks of cancer include self-sufficiency in growth signals, insensitivity to growth-inhibitory (antigrowth) signals, evasion of programmed cell death (apoptosis), limitless replicative potential, sustained angiogenesis, and tissue invasion and metastasis. Each of these physiologic changes—novel capabilities acquired during tumor development—represents the successful breaching of an anticancer defense mechanism hardwired into cells and tissues.

The terms neoplastic refers to an abnormal mass of tissue as a result of neoplasia. Neoplasia is the abnormal proliferation not cells. The growth of neoplastic cells exceeds and is not coordinated with that of the normal tissues around it. The growth persists in the same excessive manner even after cessation of the stimuli. Neoplasms may be benign, pre-cancerous or cancerous. In one embodiment, compositions and methods described herein are directed to pre-cancerous or cancerous cells. "Pre-cancerous" as used herein is an early form of cancer that is defined by the absence of invasion of tumor cells into the surrounding tissue. Pre-cancerous also refers to dysplasia, which is the earliest form of pre-cancerous lesion recognizable in a biopsy by a pathologist.

The use of the word "a" or "an" when used in conjunction with the term "comprising" in the claims and/or the specification may mean "one," but it is also consistent with the meaning of "one or more," "at least one," and "one or more than one."

The term "anti-tumorigenic" refers to cells that have a protective effect against tumor development, neoplastic of cells, and cancer. For example, "anti-tumorigenic $CD8^+$ T cells" or "anti-tumorigenic $CD4^+$ T cells" refers to cells that have a protective effect against tumor development, neoplasm, and cancer. "Anti-tumorigenic $CD8^+$ T cells" also refers to cells that have a protective effect against other diseases such as those listed under subsection V. titled: THERAPEUTIC TARGETS.

By "nanoparticle" herein is meant small discrete particles that are administrable to a subject. In certain embodiments, the nanoparticles are substantially spherical in shape. The term "substantially spherical," as used herein, means that the shape of the particles does not deviate from a sphere by more than about 10%. Various known antigen or peptide complexes of the invention may be applied to the particles. The nanosize nanopartical is critical to this invention, and the particles of this invention range in size from about 1 nm to about 100 nm in diameter and, preferably, from about 5 nm to about 15 nm in diameter. In some embodiments of this invention the nanoparticle is from about 1 nm to about 25 nm in diameter, from about 1 nm to about 50 nm in diameter, or from about 5 nm to about 10 nm in diameter. Smaller nanosize particles can be obtained, for example, fractionation whereby the larger particles are allowed to settle in an aqueous solution. The upper portion of the solution is then recovered. This upper portion is enriched in smaller size particles. The process can be repeated until a desired average size is generated.

The terms "metastatic cells" refer to cancerous cells that have acquired the ability to migrate from the primary or original tumor lesion to surrounding tissues and/or have acquired the ability to penetrate and the walls of lymphatic cells or blood vessels and circulate through the bloodstream. The term "metastasis" as used herein refers to the migration or spread of cancerous cells from one location in the body to surrounding tissues, the lymphatic system, or to blood vessels. When tumor cells metastasize, the new tumor is referred to as a metastatic tumor.

The use of the term "or" in the claims is used to mean "and/or" unless explicitly indicated to refer to alternatives only or the alternatives are mutually exclusive, although the disclosure supports a definition that refers to only alternatives and "and/or."

As used herein the terms "immunogenic agent" or "immunogen" or "antigen" are used interchangeably to describe a molecule capable of inducing an immunological response against itself on administration to a recipient, either alone, in conjunction with an adjuvant, or presented on a display vehicle.

As used herein, an "amino molecule" refers to any amino acid, amino acid derivative, or amino acid mimic known in the art. In certain embodiments, the residues of the proteinaceous molecule are sequential, without any non-amino molecule interrupting the sequence of amino molecule residues. In other embodiments, the sequence may comprise one or more non-amino molecule moieties. In particular embodiments, the sequence of residues of the proteinaceous molecule may be interrupted by one or more non-amino molecule moieties.

As used herein the phrase "immune response" or its equivalent "immunological response" refers to the development of a cell-mediated response (mediated by antigen-specific T cells or their secretion products) directed against a tumor-specific antigen or a related epitope of a tumor-specific antigen. A cellular immune response is elicited by the presentation of polypeptide epitopes in association with Class I or Class II MHC molecules, to activate antigen-specific CD4$^+$ T helper cells and/or CD8+ cytotoxic T cells. The response may also involve activation of other components.

For purposes of this specification and the accompanying claims the terms "epitope" and "antigenic determinant" are used interchangeably to refer to a site on an antigen to which B and/or T cells respond or recognize. B-cell epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., Epitope Mapping Protocols (1996). T-cells recognize continuous epitopes of about nine amino acids for CD8 cells or about 13-15 amino acids for CD4 cells. T cells that recognize the epitope can be identified by in vitro assays that measure antigen-dependent proliferation, as determined by $^3$H-thymidine incorporation by primed T cells in response to an epitope (Burke et al., 1994), by antigen-dependent killing (cytotoxic T lymphocyte assay, Tigges et al., 1996) or by cytokine secretion. The presence of a cell-mediated immunological response can be determined by proliferation assays (CD4$^+$ T cells) or CTL (cytotoxic T lymphocyte) assays.

Optionally, an antigen or preferably an epitope of an antigen, can be chemically conjugated to, or expressed as, a fusion protein with other proteins, such as MHC and MHC related proteins.

As used herein and in the claims, the terms "antibody" or "immunoglobulin" are used interchangeably and refer to any of several classes of structurally related proteins that function as part of the immune response of an animal or recipient, which proteins include IgG, IgD, IgE, IgA, IgM and related proteins.

Accordingly, the term "proteinaceous composition" encompasses amino molecule sequences comprising at least one of the 20 common amino acids in naturally synthesized proteins, or at least one modified or unusual amino acid.

As used herein, the terms "patient" and "subject" are used synonymously and refer to a mammal. In some embodiments the patient is a human. In other embodiments the patient is a mammal commonly used in a laboratory such as a mouse, rat, simian, canine, feline, bovine, equine, or ovine.

As used herein, the term "treatment" or "treating" means any treatment of a disease or condition or associated disorder, in a patient, including:
  inhibiting the disease or condition, that is, arresting or suppressing the development of clinical symptoms, such as cachexia in cancer; and/or
  relieving the disease or condition that is, causing the regression of clinical symptoms, e.g., increasing overall survival or reducing tumor burden.

In some aspects, the term treating refers to an improvement in clinical outcomes. The term "clinical outcome" refers to any clinical observation or measurement relating to a patient's reaction to a therapy. Non-limiting examples of clinical outcomes include tumor response (TR), overall survival (OS), progression free survival (PFS), disease free survival, time to tumor recurrence (TTR), time to tumor progression (TTP), relative risk (RR), toxicity or side effect. "Overall Survival" (OS) intends a prolongation in life expectancy as compared to naïve or untreated individuals or patients. "Progression free survival" (PFS) or "Time to Tumor Progression" (TTP) indicates the length of time during and after treatment that the cancer does not grow. Progression-free survival includes the amount of time patients have experienced a complete response or a partial response, as well as the amount of time patients have experienced stable disease. "Tumor Recurrence" as used herein and as defined by the National Cancer Institute is cancer that has recurred (come back), usually after a period of time during which the cancer could not be detected. The cancer may come back to the same place as the original (primary) tumor or to another place in the body. It is also called recurrent cancer. "Time to Tumor Recurrence" (TTR) is defined as the time from the date of diagnosis of the cancer to the date of first recurrence, death, or until last contact if the patient was free of any tumor recurrence at the time of last contact. If a patient had not recurred, then TTR was censored at the time of death or at the last follow-up. "Relative Risk" (RR), in statistics and mathematical epidemiology, refers to the risk of an event (or of developing a disease) relative to exposure. Relative risk is a ratio of the probability of the event occurring in the exposed group versus a non-exposed group.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

It is contemplated that nanoparticles coated with antigen/MHC/co-stimulatory molecule complexes (antigen/MHC/co-stimulatory molecules/nanoparticle complex) will expand populations of antigen-specific anti-tumorigenic T cells that target cancerous cells. It is further believed that one such population will be antigen-specific anti-tumorigenic memory T cells. It is also contemplated that subsequent administration of antigen/MHC/nanoparticle complexes without co-stimulatory molecules will expand and/or activate said pre-existing pool of antigen-specific anti-tumorigenic memory T cells. It is contemplated that this technology will expand anti-tumorigenic T cells in vivo. In some embodiments from about 17% to about 47% of all circulating CD8$^+$ T cells are antigen-specific T cells resulting from administration of nanoparticles coated with antigen-MHC complexes. It is contemplated that administering nanoparticles coated with tumor-specific antigen/MHC/co-stimulatory molecule complexes to a patient will result in a an expansion of circulating antigen-specific CD8+ T cells that are from about 5% to about 90% of total circulating T cells, or from about 10% to about 80%, or from about 10% to about 50%, or from about 50% to about 90%, or from about 20% to about 50%, or from about 30% to about 60%, or from about 35% to about 65%, or from about 40% to about 70%, or from about 45% to about 75%, or from about 50% to about 80%, or from about 25% to about 55%.

II. Pharmaceutical Compositions and Administration

The present invention includes methods for preventing, ameliorating, or treating patients suffering from disease associated with cancerous cells, neoplastic cells, metastatic cells, or developing tumors. As such, the invention contemplates "vaccines" or immune system modifiers for use in various embodiments. Compositions proposed to be suitable for use as a vaccine can be prepared from tumor-specific antigenic molecules. The invention includes compositions and methods to induce or modify an immune response against a tumor-specific antigen, e.g., a polypeptide, a peptide, a carbohydrate, a lipid or other molecule or molecular fragment.

One aspect of the present invention is a method for preventing cancerous cell growth in a patient susceptible to said cancerous cell growth. For certain types of cancers, the tumor-specific antigens are well-characterized. In these instances, a patient at risk of developing said cancer could be immunized with antigen/MHC/co-stimulatory molecule/ nanoparticle complexes that are antigen-specific for said cancer.

Administration of the compositions according to the present invention will typically be via any common route. This includes, but is not limited to parenteral, orthotopic, intradermal, subcutaneous, intramuscular, intraperitoneal, intranasal, or intravenous injection. In certain embodiments, a vaccine composition may be inhaled (e.g., U.S. Pat. No. 6,651,655, which is specifically incorporated by reference in its entirety). Additional formulations which are suitable for other modes of administration include oral formulations. Oral formulations include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders and contain about 10% to about 95% of active ingredient, preferably about 25% to about 70%.

Typically, compositions of the invention are administered in a manner compatible with the dosage formulation and frequency, and in such amount as will be therapeutically effective and immune modifying. The quantity to be administered depends on the subject to be treated. Precise amounts of active ingredient required to be administered depend on the judgment of the practitioner. However, suitable dosage ranges are of the order of ten to several hundred nanograms or micrograms antigen/MHC/co-stimulatory molecule/ nanoparticle complex per administration. Suitable regimes for initial administration and boosters are also variable, but are typified by an initial administration followed by subsequent administrations.

The manner of application may be varied widely. Any of the conventional methods for administration of a vaccine are applicable. These are believed to include oral application on a solid physiologically acceptable base or in a physiologically acceptable dispersion, parenterally, by injection and the like. The dosage of the antigen/MHC/co-stimulatory nanoparticle complex will depend on the route of administration, the frequency of administration and will vary according to the size and health of the subject.

In many instances, it will be desirable to have multiple administrations of a peptide/MHC/co-stimulatory molecule/ nanoparticle complex, about, at most about or at least about 3, 4, 5, 6, 7, 8, 9, 10 or more. The administrations will normally range from 2 day to twelve week intervals, more usually from one to two week intervals. Periodic boosters at intervals of 0.5-5 years, usually two years, will be desirable to maintain the condition of the immune system. The course of the administrations may be followed by assays for immune responses and T cell activity to monitor therapy and treatment. As such, the present methods can be combined with known methods for the monitoring of immune therapy to provide a course of treatment to the patient until reaching a desired clinical endpoint.

A. Combination Therapy

The compositions and related methods of the present invention, particularly administration of a antigen/MHC/co-stimulatory molecule/nanoparticle complex, may also be used in combination with the administration of traditional therapies.

In one aspect, it is contemplated that a antigen/MHC/co-stimulatory molecule/nanoparticle complex is used in conjunction with a cytokine treatment. Alternatively, antigen/ MHC/co-stimulatory molecule/nanoparticle complex administration may precede or follow the other treatment by intervals ranging from minutes to weeks. In embodiments where the other agents and/or antigen/MHC/co-stimulatory molecule/nanoparticle complexes are administered separately, one would generally ensure that a significant period of time did not expire between the time of each delivery, such that the agent and antigen/MHC/co-stimulatory molecule/nanoparticle complex would still be able to exert an advantageously combined effect on the subject. In such instances, it is contemplated that one may administer both modalities within about 12-24 h of each other and, more preferably, within about 6-12 h of each other. In some situations, it may be desirable to extend the time period for administration significantly, however, where several days (2, 3, 4, 5, 6 or 7) to several weeks (1, 2, 3, 4, 5, 6, 7 or 8) lapse between the respective administrations.

Various combinations may be employed, for example antigen/MHC/co-stimulatory molecule/nanoparticle complex administration is "A" and the additional agent is "B":

A/B/A B/A/B B/B/A A/A/B A/B/B B/A/A A/B/B/B B/A/B/B
B/B/B/A B/B/A/B A/A/B/B A/B/A/B A/B/B/A/ B/B/A/A
B/A/B/A B/A/A/B A/A/A/B B/A/A/A A/B/A/A A/A/B/A

Administration of the peptide-MHC-co-stimulatory complex compositions of the present invention to a patient/ subject will follow general protocols for the administration of such compounds, taking into account the toxicity, if any. It is expected that the treatment cycles would be repeated as necessary. It also is contemplated that various standard therapies, such as hydration, may be applied in combination with the described therapy.

B. Pharmaceutical Compositions

In some embodiments, pharmaceutical compositions are administered to a subject. Different aspects of the present invention involve administering an effective amount of a antigen/MHC/co-stimulatory molecule/nanoparticle complex composition to a subject. Additionally, such compositions can be administered in combination with modifiers of the immune system. Such compositions will generally be dissolved or dispersed in a pharmaceutically acceptable carrier or aqueous medium.

The phrases "pharmaceutically acceptable" or "pharmacologically acceptable" refer to molecular entities and compositions that do not produce an adverse, allergic, or other untoward reaction when administered to an animal, or human. As used herein, "pharmaceutically acceptable carrier" includes any and all solvents, dispersion media, coatings, antibacterial and antifungal agents, isotonic and absorption delaying agents, and the like. The use of such media and agents for pharmaceutical active substances is well known in the art. Except insofar as any conventional media or agent is incompatible with the active ingredients, its use in immunogenic and therapeutic compositions is contemplated.

The active compounds of the present invention can be formulated for parenteral administration, e.g., formulated for injection via the intravenous, intramuscular, sub-cutaneous, or even intraperitoneal routes. The preparation of an aqueous composition that contains a antigen/MHC/co-stimulatory molecule/nanoparticle complex that modifies the subject's immune response will be known to those of skill in the art in light of the present disclosure. Typically, such compositions can be prepared as injectables, either as liquid solutions or suspensions; solid forms suitable for use to prepare solutions or suspensions upon the addition of a liquid prior to injection can also be prepared; and, the preparations can also be emulsified.

The pharmaceutical forms suitable for injectable use include sterile aqueous solutions or dispersions; formulations including sesame oil, peanut oil, or aqueous propylene glycol; and sterile powders for the extemporaneous preparation of sterile injectable solutions or dispersions. In all cases the form must be sterile and must be fluid to the extent that it may be easily injected. It also should be stable under the conditions of manufacture and storage and must be preserved against the contaminating action of microorganisms, such as bacteria and fungi.

The compositions may be formulated into a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier also can be a solvent or dispersion medium containing, for example, water, ethanol, polyol (for example, glycerol, propylene glycol, and liquid poly(ethylene glycol), and the like), suitable mixtures thereof, and vegetable oils. The proper fluidity can be maintained, for example, by the use of a coating, such as lecithin, by the maintenance of the required particle size in the case of dispersion, and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by sterilization. Sterilization of the solution will be done in such a way as to not diminish the anti-pathogenic properties of the peptide/MHC/co-stimulatory molecule/nanoparticle. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques, which yield a powder of the active ingredient, plus any additional desired ingredient from a previously sterilized solution thereof. One such method of sterilization of the solution is sterile filtration, however, this invention is meant to include any method of sterilization that does not significantly decrease the anti-pathogenic properties of the peptide/MHC/co-stimulatory molecule/nanoparticle complexes. Methods of sterilization that involve intense heat and pressure, such as autoclaving, may compromise the tertiary structure of the complex, thus significantly decreasing the anti-pathogenic properties of the peptide/MHC/co-stimulatory molecule/nanoparticle complexes.

An effective amount of therapeutic or prophylactic composition is determined based on the intended goal. The term "unit dose" or "dosage" refers to physically discrete units suitable for use in a subject, each unit containing a predetermined quantity of the composition calculated to produce the desired responses discussed above in association with its administration, i.e., the appropriate route and regimen. The quantity to be administered, both according to number of treatments and unit dose, depends on the result and/or protection desired. Precise amounts of the composition also depend on the judgment of the practitioner and are peculiar to each individual. Factors affecting dose include physical and clinical state of the subject, route of administration, intended goal of treatment (alleviation of symptoms versus cure), and potency, stability, and toxicity of the particular composition. Upon formulation, solutions will be administered in a manner compatible with the dosage formulation and in such amount as is therapeutically or prophylactically effective. The formulations are easily administered in a variety of dosage forms, such as the type of injectable solutions described above.

C. In Vitro or Ex Vivo Administration

As used herein, the term in vitro administration refers to manipulations performed on cells removed from or outside of a subject, including, but not limited to cells in culture. The term ex vivo administration refers to cells which have been manipulated in vitro, and are subsequently administered to a subject. The term in vivo administration includes all manipulations performed within a subject, including administrations.

In certain aspects of the present invention, the compositions may be administered either in vitro, ex vivo, or in vivo. In certain in vitro embodiments, autologous T cells are incubated with compositions of this invention. The cells can then be used for in vitro analysis, or alternatively for ex vivo administration.

III. Antigen/MHC Complexes and Co-Stimulatory Molecules

Antigens, including segments, fragments and other molecules derived from an antigenic species, including but not limited to peptides, carbohydrates, lipids or other molecules presented by classical and non-classical MEW molecules of the invention are typically complexed or operatively coupled to a MHC molecule or derivative thereof. Antigen recognition by T lymphocytes is major histocompatibility complex (MHC)-restricted. A given T lymphocyte will recognize an antigen only when it is bound to a particular MHC molecule. In general, T lymphocytes are stimulated only in the presence of self MHC molecules, and antigen is recognized as fragments of the antigen bound to self MHC molecules. MHC restriction defines T lymphocyte specificity in terms of the antigen recognized and in terms of the MHC molecule that binds its antigenic fragment(s). In particular aspects certain antigens will be paired with certain MHC molecules or polypeptides derived there from.

The term "operatively coupled" or "coated" as used herein, refers to a situation where individual polypeptide (e.g., MHC) and antigenic (e.g., peptide) components are combined to form the active complex prior to binding at the target site, for example, an immune cell. This includes the situation where the individual polypeptide complex components are synthesized or recombinantly expressed and subsequently isolated and combined to form a complex, in vitro, prior to administration to a subject; the situation where a chimeric or fusion polypeptide (i.e., each discrete protein component of the complex is contained in a single polypeptide chain) is synthesized or recombinantly expressed as an intact complex. Typically, polypeptide complexes are added to the nanoparticles to yield nanoparticles with adsorbed or coupled polypeptide complexes having a ratio of number of molecules:number of nanoparticles from about, at least about or at most about 0.1, 0.5, 1, 10, 100, 500, 1000 or more to:1, more typically 0.1:1 to 50:1. The polypeptide content of the nanoparticles can be determined using standard techniques.

A. Co-Stimulatory Molecule Components

Co-stimulatory molecules are molecules that produce a secondary signal in vivo that serves to activate naïve T cells into antigen-specific T cells capable of producing an immune response to cells possessing said specific antigen. The present invention is not limited to any specific co-stimulatory molecule. The various co-stimulatory molecules are well-known in the art. Some non-limiting examples of co-stimulatory molecules are B7.1, 4-IBBL, CD40, IL-15/IL-15Ra, CD28, CD80, CD86, and ICOS. Only one specific co-stimulatory molecule may be coupled to one nanoparticle or a variety of co-stimulatory molecules may be coupled to the same nanoparticle. In certain embodiments the co-stimulatory molecule is a protein such as an antibody that is capable of agonizing a co-stimulatory receptor on a T cell. In this case, the antibody is capable of inducing a co-stimulatory signal that is necessary to activate naïve T cells and induce an immune response in an antigen-specific manner.

The co-stimulatory molecule can be coupled to the nanoparticle in the same manner as the antigen/MHC complex. In one embodiment of the present invention, the co-stimulatory molecule and the antigen/MHC complex are separately attached to the nanoparticle. In another embodiment of the invention, the co-stimulatory molecule and the antigen/MHC complex are first complexed together and are then subsequently complexed to the nanoparticle. Typically, polypeptide complexes are added to the nanoparticles to yield nanoparticles with adsorbed or coupled polypeptide complexes having a ratio of number of molecules:number of nanoparticles from about, at least about or at most about 0.1, 0.5, 1, 10, 100, 500, 1000 or more to:1, more typically 0.1:1 to 50:1. The polypeptide content of the nanoparticles can be determined using standard techniques. The ration of the co-stimulatory molecule to the antigen/MHC complex can be from about 0.1, 0.5, 1, 2, 5, 10, 50 or more to 1, preferably a ratio of 1:1 of co-stimulatory molecule:antigen/MHC complex is obtained.

B. MHC Molecules

Intracellular and extracellular antigens present quite different challenges to the immune system, both in terms of recognition and of appropriate response. Presentation of antigens to T cells is mediated by two distinct classes of molecules MHC class I (MHC-I) and MHC class II (MHC-II), which utilize distinct antigen processing pathways. Peptides derived from intracellular antigens are presented to $CD8^+$ T cells by MHC class I molecules, which are expressed on virtually all cells, while extracellular antigen-derived peptides are presented to $CD4^+$ T cells by MHC-II molecules. However, there are certain exceptions to this dichotomy. Several studies have shown that peptides generated from endocytosed particulate or soluble proteins are presented on MHC-I molecules in macrophages as well as in dendritic cells. In certain embodiments of the invention, a particular peptide derived from a tumor-specific antigen is identified and presented in the peptide/MHC/co-stimulatory molecule/nanoparticle complex in the context of an appropriate MHC class I or II polypeptide. In certain aspects, the genetic makeup of a subject may be assessed to determine which MHC polypeptide is to be used for a particular patient and a particular set of peptides.

Non-classical MEW molecules are also contemplated for use in MEW complexes of the invention. Non-classical MEW molecules are non-polymorphic, conserved among species, and possess narrow, deep, hydrophobic ligand binding pockets. These binding pockets are capable of presenting glycolipids and phospholipids to Natural Killer T (NKT) cells. NKT cells represent a unique lymphocyte population that co-express NK cell markers and a semi-invariant T cell receptor (TCR). They are implicated in the regulation of immune responses associated with a broad range of diseases.

C. Antigenic Components

Certain aspects of the invention include methods and compositions concerning antigenic compositions including segments, fragments, or epitopes of polypeptides, peptides, nucleic acids, carbohydrates, lipids and other molecules that provoke or induce an antigenic response, generally referred to as antigens. In particular, antigens, or antigenic segments or fragments of such antigens, which lead to the destruction of a cell via an immune response, can be identified and used in making a MHC/nanoparticle complex described herein. Such antigens can be presented on and are specific to tumor cells. Embodiments of the invention include compositions and methods for the modulation of an immune response against a particular cell or set of cells that carry out a particular physiologic function. Examples of tumor antigens include antigens disclosed in the following table.

| | |
|---|---|
| SEQ ID No. 1 | Lys Ile Ser Val Ser Leu Pro Leu Ser Leu Ser Gln Ser Val Cys |
| SEQ ID No. 2 | Gln Leu Ser Lys Asp Thr Ser Val Leu Thr Phe Thr Phe Cys |
| SEQ ID No. 3 | Cys Ser Asp Ala His Pro Gly Asp Ser Ser Gly Asp Ser Ser Gly Leu Asn |
| SEQ ID No. 4 | Arg Gly Glu Val Arg Gln Phe Thr Leu Arg His Trp Leu Lys Val |
| SEQ ID No. 5 | Gly Asp Tyr Leu Asn Asp Glu Ala Leu Trp Asn Lys Cys |

| | |
|---|---|
| SEQ ID No. 6 | Gly Lys Val Ile Asp Asp Asn Asp His Leu Ser Gln Glu Ile Cys |
| SEQ ID No. 7 | Leu Met Ala Asn Ser Thr Trp Gly Tyr Pro Phe His Asp Gly |
| SEQ ID No. 8 | Leu Asn Val Val Pro Trp Asn Leu Thr Leu Phe Ser Ile Leu |
| SEQ ID No. 9 | Thr His Ser Phe Thr Ala Phe Lys Arg His Val Cys |
| SEQ ID No. 10 | Asn Leu Ser Leu Pro Pro Ser Leu Ser Leu Ser Ile Cys |
| SEQ ID No. 11 | Glu Arg Pro Ser Ser Val Leu Thr Ile Tyr Asp Ile Gly Ile Gln Cys |
| SEQ ID No. 12 | Cys Tyr Gln Gln Tyr Thr Asn Leu Gln Glu Arg Pro Ser Ser Val |
| SEQ ID No. 13 | Thr Val Glu Pro Glu Thr Gly Asp Pro Val Thr Leu Arg Leu Cys |
| SEQ ID No. 14 | Cys Ser Arg Lys Lys Arg Ala Asp Lys Lys Glu Asn Gly Thr Lys Leu Leu |
| SEQ ID No. 15 | Phe Leu Leu Val Leu Gly Phe Ile Ile |
| SEQ ID No. 16 | Val Leu Pro Ser Val Ala Met Phe Leu |
| SEQ ID No. 17 | Leu Val Leu Gly Phe Ile Ile Ala Leu |
| SEQ ID No. 18 | Lys Val Val Thr Ser Ser Phe Val Val |
| SEQ ID No. 19 | Leu Val Pro Gly Thr Lys Phe Tyr Ile |
| SEQ ID No. 20 | Leu Leu Pro Ile Arg Thr Leu Pro Leu |
| SEQ ID No. 21 | Tyr Leu Val Lys Lys Gly Thr Ala Thr |
| SEQ ID No. 22 | Ser Leu Phe Ala Glu Thr Ile Trp Val |
| SEQ ID No. 23 | Met Leu Ile Ala Met Tyr Phe Tyr Thr |
| SEQ ID No. 24 | Leu Met Trp Thr Leu Pro Val Met Leu |
| SEQ ID No. 25 | Met Leu Ile Val Tyr Ile Phe Glu Cys |
| SEQ ID No. 26 | Tyr Ile Phe Glu Cys Ala Ser Cys Ile |
| SEQ ID No. 27 | Leu Val Leu Met Leu Ile Val Tyr Ile |
| SEQ ID No. 28 | Ala Leu Cys Arg Arg Arg Ser Met Val |
| SEQ ID No. 29 | Leu Leu Ser Gly Leu Ser Leu Phe Ala |
| SEQ ID No. 30 | Phe Leu Leu Val Val Gly Leu Ile Val |
| SEQ ID No. 31 | Leu Val Val Gly Leu Ile Val Ala Leu |
| SEQ ID No. 32 | Lys Val Val Lys Ser Asp Phe Val Val |
| SEQ ID No. 33 | Thr Leu Pro Val Gln Thr Leu Pro Leu |
| SEQ ID No. 34 | Asp Leu His Val Ile Ser Asn Asp Val |
| SEQ ID No. 35 | Val Leu Val His Pro Gln Trp Val Leu |
| SEQ ID No. 36 | Phe Leu Arg Pro Gly Asp Asp Ser Ser |
| SEQ ID No. 37 | Ala Leu Gly Thr Thr Cys Tyr Ala Ser |
| SEQ ID No. 38 | Lys Leu Gln Cys Val Asp Leu His Val |
| SEQ ID No. 39 | Glu Leu Ala His Tyr Asp Val Leu Leu |
| SEQ ID No. 40 | Asn Leu Asn Gly Ala Gly Asp Pro Leu |
| SEQ ID No. 41 | Thr Leu Arg Val Asp Cys Thr Pro Leu |
| SEQ ID No. 42 | Met Met Asn Asp Gln Leu Met Phe Leu |
| SEQ ID No. 43 | Ala Leu Phe Asp Ile Glu Ser Lys Val |
| SEQ ID No. 44 | Leu Leu His Glu Thr Asp Ser Ala Val |
| SEQ ID No. 45 | Val Leu Ala Lys Glu Leu Lys Phe Val |
| SEQ ID No. 46 | Ile Leu Leu Trp Gln Pro Ile Pro Val |
| SEQ ID No. 47 | Asp Leu Phe Gly Ile Trp Ser Lys Val |
| SEQ ID No. 48 | Pro Leu Glu Arg Phe Ala Glu Leu Val |
| SEQ ID No. 49 | Lys Gln Gly Asn Phe Asn Ala Trp Val |
| SEQ ID No. 50 | Asn Leu Leu Arg Arg Met Trp Val Thr |
| SEQ ID No. 51 | Asn Leu Phe Glu Thr Pro Ile Leu Ala |
| SEQ ID No. 52 | Asn Leu Phe Glu Thr Pro Val Glu Ala |
| SEQ ID No. 53 | Gly Leu Gln His Trp Val Pro Glu Leu |
| SEQ ID No. 54 | Val Gln Phe Val Ala Ser Tyr Lys Val |
| SEQ ID No. 55 | Arg Leu Leu Ala Ala Leu Cys Gly Ala |
| SEQ ID No. 56 | Leu Leu Leu Leu Thr Val Leu Thr Val |
| SEQ ID No. 57 | Leu Leu Leu Thr Val Leu Thr Val Val |
| SEQ ID No. 58 | Phe Leu Ser Phe His Ile Ser Asn Leu |
| SEQ ID No. 59 | Leu Leu Val Leu Val Cys Val Leu Val |
| SEQ ID No. 60 | Ala Leu Val Leu Val Cys Val Leu |
| SEQ ID No. 61 | Ser Leu Ser Tyr Thr Asn Pro Ala Val |
| SEQ ID No. 62 | Asn Leu Thr Ile Ser Asp Val Ser Val |
| SEQ ID No. 63 | Ala Leu Ala Ser Thr Ala Pro Pro Val |
| SEQ ID No. 64 | Ala Ile Leu Cys Trp Thr Phe Trp Val |
| SEQ ID No. 65 | Phe Ile Leu Met Phe Ile Val Tyr Ala |
| SEQ ID No. 66 | Leu Thr Ala Glu Cys Ile Phe Phe Val |
| SEQ ID No. 67 | Met Leu Gln Asp Asn Cys Cys Gly Val |
| SEQ ID No. 68 | Ile Leu Cys Trp Thr Phe Trp Val Leu |
| SEQ ID No. 69 | Lys Ile Leu Leu Ala Tyr Phe Ile Leu |
| SEQ ID No. 70 | Phe Val Gly Ile Cys Leu Phe Cys Leu |
| SEQ ID No. 71 | Val Leu Leu Ser Val Ala Met Phe Leu |
| SEQ ID No. 72 | Leu Leu Ser Val Ala Met Phe Leu Leu |
| SEQ ID No. 73 | Ile Leu Gly Ser Leu Pro Phe Phe Leu |
| SEQ ID No. 74 | Ile Leu Asn Ala Tyr Leu Val Arg Val |
| SEQ ID No. 75 | Phe Leu Leu Val Gly Phe Ala Gly Ala |
| SEQ ID No. 76 | Asn Leu Gln Pro Gln Leu Ala Ser Val |
| SEQ ID No. 77 | Cys Met Phe Asp Ser Lys Glu Ala Leu |
| SEQ ID No. 78 | Tyr Leu Tyr Val Leu Val Asp Ser Ala |
| SEQ ID No. 79 | Tyr Met Asp Gly Thr Met Ser Gln Val |
| SEQ ID No. 80 | Lys Met Ala Arg Phe Ser Tyr Ser Val |

```
SEQ ID No. 81    Gly Leu Val Met Asp Glu His Leu Val

SEQ ID No. 82    Phe Leu Pro Gly Cys Asp Gly Leu Val

SEQ ID No. 83    Cys Met Leu Gly Ser Phe Cys Ala Cys

SEQ ID No. 84    Tyr Leu Ala Phe Arg Asp Asp Ser Ile

SEQ ID No. 85    Trp Leu Pro Lys Lys Cys Ser Leu Cys

SEQ ID No. 86    Cys Leu Asn Gly Gly Thr Cys Met Leu

SEQ ID No. 87    Met Leu Val Gly Ile Cys Leu Ser Ile

SEQ ID No. 88    Phe Glu Leu Gly Leu Val Ala Gly Leu

SEQ ID No. 89    Lys Met Val Arg Phe Ser Tyr Ser Val

SEQ ID No. 90    Cys Leu Asn Glu Gly Thr Cys Met Leu

SEQ ID No. 91    Met Leu Ala Gly Ile Cys Leu Ser Ile

SEQ ID No. 92    Arg Leu Leu Phe Phe Leu Leu Phe Leu

SEQ ID No. 93    Thr Leu Ala Tyr Leu Ile Phe Cys Leu

SEQ ID No. 94    Leu Leu Phe Leu Thr Pro Met Glu Val

SEQ ID No. 95    Lys Leu Met Ser Pro Lys Leu Tyr Val

SEQ ID No. 96    Leu Leu Phe Phe Leu Leu Phe Leu Val

SEQ ID No. 97    Ser Leu Phe Leu Gly Ile Leu Ser Val

SEQ ID No. 98    Ala Ile Ser Gly Met Ile Leu Ser Ile

SEQ ID No. 99    Phe Ile Arg Ala His Thr Pro Tyr Ile

SEQ ID No. 100   Ser Leu Asn Phe Ile Arg Ala His Thr

SEQ ID No. 101   Leu Lys Met Glu Ser Leu Asn Phe Ile

SEQ ID No. 102   Ser His Phe Leu Lys Met Glu Ser Leu

SEQ ID No. 103   Tyr Leu Phe Leu Gly Ile Leu Ser Val
```

1. Peptide Components and Proteinaceous Compositions

Polypeptides and peptides of the invention may be modified by various amino acid deletions, insertions, and/or substitutions. In particular embodiments, modified polypeptides and/or peptides are capable of modulating an immune response in a subject. As used herein, a "protein" or "polypeptide" or "peptide" refers to a molecule comprising at least five amino acid residues. In some embodiments, a wild-type version of a protein or peptide are employed, however, in many embodiments of the invention, a modified protein or polypeptide is employed to generate a peptide/MHC/co-stimulatory molecule/nanoparticle complex. A peptide/MHC/co-stimulatory molecule/nanoparticle complex can be used to generate an immune response and/or to modify the T cell population of the immune system (i.e., re-educate the immune system). The terms described above may be used interchangeably herein. A "modified protein" or "modified polypeptide" or "modified peptide" refers to a protein or polypeptide whose chemical structure, particularly its amino acid sequence, is altered with respect to the wild-type protein or polypeptide. In some embodiments, a modified protein or polypeptide or peptide has at least one modified activity or function (recognizing that proteins or polypeptides or peptides may have multiple activities or functions). It is specifically contemplated that a modified protein or polypeptide or peptide may be altered with respect to one activity or function yet retains a wild-type activity or function in other respects, such as immunogenicity or ability to interact with other cells of the immune system when in the context of an MHC/co-stimulatory molecule/nanoparticle complex.

Peptides of the invention include peptides that are found to be specific to cancerous or pre-cancerous cells in the body. These peptides may be associated with specific nanoparticle/MHC/co-stimulatory molecules or multiple peptides may be associated with a common nanoparticle and one or more MHC molecule. Administration of combinations of these peptides includes administering a population of nanoparticles having multiple peptides attached and/or administering multiple nanoparticle populations each having a specific peptide attached or a combination of such nanoparticles that includes nanoparticles with 1, 2, 3, 4, 5, 6, or more peptides attached to 1, 2, 3, 4, 5, 6, or more nanoparticles In certain embodiments, the size of a protein or polypeptide (wild-type or modified), including any complex of a protein or peptide of interest and in particular a MHC/peptide fusion, may comprise, but is not limited to 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, 1000, 1100, 1200, 1300, 1400, 1500, 1750, 2000, 2250, 2500 amino molecules or greater, including any range or value derivable therein, or derivative thereof. In certain aspects, 5, 6, 7, 8, 9, 10 or more contiguous amino acids, including derivatives thereof, and fragments of an antigen, such as those amino acid sequences disclosed and referenced herein, can be used as antigens. It is contemplated that polypeptides may be mutated by truncation, rendering them shorter than their corresponding wild-type form, but also they might be altered by fusing or conjugating a heterologous protein sequence with a particular function (e.g., for presentation as a protein complex, for enhanced immunogenicity, etc.).

Proteinaceous compositions may be made by any technique known to those of skill in the art, including (i) the expression of proteins, polypeptides, or peptides through standard molecular biological techniques, (ii) the isolation of proteinaceous compounds from natural sources, or (iii) the chemical synthesis of proteinaceous materials. The nucleotide as well as the protein, polypeptide, and peptide sequences for various genes have been previously disclosed, and may be found in the recognized computerized databases. One such database is the National Center for Biotechnology Information's GenBank and GenPept databases (on the World Wide Web at ncbi.nlm.nih.gov/). The all or part of the coding regions for these genes may be amplified and/or expressed using the techniques disclosed herein or as would be known to those of ordinary skill in the art.

Amino acid sequence variants of antigenic epitopes and other polypeptides of these compositions can be substitutional, insertional, or deletion variants. A modification in a polypeptide of the invention may affect 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500 or more non-contiguous or contiguous amino acids of a peptide or polypeptide, as compared to wild-type. A peptide or polypeptide that results in an immune response is contemplated for use in methods of the invention.

Deletion variants typically lack one or more residues of the native or wild-type amino acid sequence. Individual residues can be deleted or a number of contiguous amino acids can be deleted. A stop codon may be introduced (by substitution or insertion) into an encoding nucleic acid sequence to generate a truncated protein. Insertional mutants typically involve the addition of material at a non-terminal point in the polypeptide. This may include the insertion of one or more residues. Terminal additions, called fusion proteins, may also be generated.

Substitutional variants typically contain the exchange of one amino acid for another at one or more sites within the protein, and may be designed to modulate one or more properties of the polypeptide, with or without the loss of other functions or properties. Substitutions may be conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine. Alternatively, substitutions may be non-conservative such that a function or activity of a polypeptide or peptide is affected, such as avidity or affinity for a cellular receptor(s). Non-conservative changes typically involve substituting a residue with one that is chemically dissimilar, such as a polar or charged amino acid for a nonpolar or uncharged amino acid, and vice versa.

Proteins of the invention may be recombinant, or synthesized in vitro. Alternatively, a recombinant protein may be isolated from bacteria or other host cell.

The term "functionally equivalent codon" is used herein to refer to codons that encode the same amino acid, such as the six codons for arginine or serine, and also refers to codons that encode biologically equivalent amino acids (see Table 2, below).

TABLE 2

Codon Table

| Amino Acids | | | Codons |
|---|---|---|---|
| Alanine | Ala | A | GCA GCC GCG GCU |
| Cysteine | Cysts | C | UGC UGU |
| Aspartic acid | Asp | D | GAC GAU |
| Glutamic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | AGC AGU UCA UCC UCG UCU |
| Threonine | Thr | T | ACA ACC ACG ACI |
| Valine | Val | V | GUA GUC GUG GUU |
| Tryptophan | Trp | W | UGG |
| Tyrosine | Tyr | Y | UAC UAU |

It also will be understood that amino acid and nucleic acid sequences may include additional residues, such as additional N- or C-terminal amino acids, or 5' or 3' nucleic acid sequences, respectively, and yet still be essentially as set forth in one of the sequences disclosed herein, so long as the sequence meets the criteria set forth above, including the maintenance of biological protein activity (e.g., immunogenicity). The addition of terminal sequences particularly applies to nucleic acid sequences that may, for example, include various non-coding sequences flanking either of the 5' or 3' portions of the coding region.

It is contemplated that in compositions of the invention, there is between about 0.001 mg and about 10 mg of total protein per ml. Thus, the concentration of protein in a composition can be about, at least about or at most about 0.001, 0.010, 0.050, 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 50, 100 μg/ml or mg/ml or more (or any range derivable therein). Of this, about, at least about, or at most about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100% may be peptide/MHC/co-stimulatory molecule/nanoparticle complex.

The present invention contemplates the administration of a peptide/MHC/-stimulatory molecule/nanoparticle complex to effect a treatment or preventative therapy against the development of a disease or condition associated with cancer, neoplastic cells, or tumor development.

In addition, U.S. Pat. No. 4,554,101 (Hopp), which is incorporated herein by reference, teaches the identification and preparation of epitopes from primary amino acid sequences on the basis of hydrophilicity. Through the methods disclosed in Hopp, one of skill in the art would be able to identify potential epitopes from within an amino acid sequence and confirm their immunogenicity. Numerous scientific publications have also been devoted to the prediction of secondary structure and to the identification of epitopes, from analyses of amino acid sequences (Chou & Fasman, 1974a,b; 1978a,b; 1979). Any of these may be used, if desired, to supplement the teachings of Hopp in U.S. Pat. No. 4,554,101.

2. Other Antigenic Components

Molecules other than peptides can be used as antigens or antigenic fragments in complex with MHC molecules, such molecules include, but are not limited to carbohydrates, lipids, small molecules, and the like. Carbohydrates are major components of the outer surface of a variety of cells. Certain carbohydrates are characteristic of different stages of differentiation and very often these carbohydrates are recognized by specific antibodies. Expression of distinct carbohydrates can be restricted to specific cell types. Autoantibody responses to endometrial and serum antigens have been shown to be a common feature of endometriosis. There has been described a serum autoantibody response in endometriosis to a number of previously identified antigens, including 2-Heremans Schmidt glycoprotein and carbonic anhydrase, that is specific for a carbohydrate epitope (Yeaman et al., 2002).

D. Substrates/Nanoparticles

In certain aspect, antigen/MHC complexes are operatively coupled to a substrate. A substrate can be in the form of a nanoparticle comprising a biocompatible, bioabsorbable material. A substrate can also be in the form of a nanoparticle such as those described previously in U.S. Patent Application Publication No. 2009/0155292 which is herein incorporated by reference in its entirety. Nanoparticles can have a structure of variable dimension and known variously as a nanosphere, a nanoparticle or a biocompatible biodegradable nanosphere or a biocompatible biodegradable nanoparticle. Such particulate formulations containing an antigen/MHC complex can be formed by covalent or non-covalent coupling of the complex to the nanoparticle.

The nanoparticles typically consist of a substantially spherical core and optionally one or more layers. The core may vary in size and composition. In addition to the core, the nanoparticle may have one or more layers to provide functionalities appropriate for the applications of interest. The thicknesses of layers, if present, may vary depending on the needs of the specific applications. For example, layers may impart useful optical properties.

Layers may also impart chemical or biological functionalities, referred to herein as chemically active or biologically active layers, and for these functionalities the layer or layers may typically range in thickness from about 0.001 micrometers (1 nanometer) to about 10 micrometers or more (depending on the desired nanoparticle diameter), these layers typically being applied on the outer surface of the nanoparticle.

The compositions of the core and layers may vary. Suitable materials for the particles or the core include, but are not limited to polymers, ceramics, glasses, minerals, and the like. Examples include, but are not limited to, standard and specialty glasses, silica, polystyrene, polyester, polycarbonate, acrylic polymers, polyacrylamide, polyacrylonitrile, polyamide, fluoropolymers, silicone, celluloses, silicon, metals (e.g., iron, gold, silver), minerals (e.g., ruby), nanoparticles (e.g., gold nanoparticles, colloidal particles, metal oxides, metal sulfides, metal selenides, and magnetic materials such as iron oxide), and composites thereof. The core could be of homogeneous composition, or a composite of two or more classes of material depending on the properties desired. In certain aspects, metal nanoparticles will be used. These metal particles or nanoparticles can be formed from Au, Pt, Pd, Cu, Ag, Co, Fe, Ni, Mn, Sm, Nd, Pr, Gd, Ti, Zr, Si, and In, precursors, their binary alloys, their ternary alloys and their intermetallic compounds. See U.S. Pat. No. 6,712, 997, which is incorporated herein by reference in its entirety. In certain embodiments, the compositions of the core and layers may vary provided that the nanoparticles are biocompatible and bioabsorbable. The core could be of homogeneous composition, or a composite of two or more classes of material depending on the properties desired. In certain aspects, metal nanosperes will be used. These metal nanoparticles can be formed from Fe, Ca, Ga and the like.

As previously stated, the nanoparticle may, in addition to the core, include one or more layers. The nanoparticle may include a layer consisting of a biodegradable sugar or other polymer. Examples of biodegradable layers include but are not limited to dextran; poly(ethylene glycol); poly(ethylene oxide); mannitol; poly(esters) based on polylactide (PLA), polyglycolide (PGA), polycaprolactone (PCL); poly(hydroxalkanoate)s of the PHB-PHV class; and other modified poly(saccharides) such as starch, cellulose and chitosan. Additionally, the nanoparticle may include a layer with suitable surfaces for attaching chemical functionalities for chemical binding or coupling sites.

Layers can be produced on the nanoparticles in a variety of ways known to those skilled in the art. Examples include sol-gel chemistry techniques such as described in Iler (1979); Brinker and Scherer (1990). Additional approaches to producing layers on nanoparticles include surface chemistry and encapsulation techniques such as described in Partch and Brown (1998); Pekarek et al. (1994); Hanprasopwattana (1996); Davies (1998); and references therein. Vapor deposition techniques may also be used; see for example Golman and Shinohara (2000); and U.S. Pat. No. 6,387,498. Still other approaches include layer-by-layer self-assembly techniques such as described in Sukhorukov et al. (1998); Caruso et al. (1998); Caruso et al. (1999); U.S. Pat. No. 6,103,379 and references cited therein.

Nanoparticles may be formed by contacting an aqueous phase containing the antigen/MHC/co-stimulatory molecule complex and a polymer and a nonaqueous phase followed by evaporation of the nonaqueous phase to cause the coalescence of particles from the aqueous phase as taught in U.S. Pat. No. 4,589,330 or 4,818,542. Preferred polymers for such preparations are natural or synthetic copolymers or polymers selected from the group consisting of gleatin agar, starch, arabinogalactan, albumin, collagen, polyglycolic acid, polylactic acid, glycolide-L(-) lactide poly(episilon-caprolactone, poly(epsilon-caprolactone-CO-lactic acid), poly(epsilon-caprolactone-CO-glycolic acid), poly(β-hydroxy butyric acid), poly(ethylene oxide), polyethylene, poly(alkyl-2-cyanoacrylate), poly(hydroxyethyl methacrylate), polyamides, poly(amino acids), poly(2-hydroxyethyl DL-aspartamide), poly(ester urea), poly(L-phenylalanine/ethylene glycol/1,6-diisocyanatohexane) and poly(methyl methacrylate). Particularly preferred polymers are polyesters, such as polyglycolic acid, polylactic acid, glycolide-L(-) lactide poly(episilon-caprolactone, poly(epsilon-caprolactone-CO-lactic acid), and poly(epsilon-caprolactone-CO-glycolic acid. Solvents useful for dissolving the polymer include: water, hexafluoroisopropanol, methylenechloride, tetrahydrofuran, hexane, benzene, or hexafluoroacetone sesquihydrate.

E. Coupling Antigen-MHC and Co-Stimulatory Molecule Complexes with the Nanoparticle In order to couple the substrate or nanoparticle to the antigen-MHC and co-stimulatory molecule complexes the following techniques can be applied.

The binding can be generated by chemically modifying the substrate or nanoparticle which typically involves the generation of "functional groups" on the surface, said functional groups being capable of binding to an antigen-MHC complex, co-stimulatory molecule, and/or linking the optionally chemically modified surface of the substrate or nanoparticle with covalently or non-covalently bonded so-called "linking molecules," followed by reacting the antigen-MHC complex and co-stimulatory molecule with the nanoparticles obtained.

The term "linking molecule" means a substance capable of linking with the substrate or nanoparticle and also capable of linking to an antigen-MHC-co-stimulatory molecule complex.

The term "functional groups" as used herein is not restricted to reactive chemical groups forming covalent bonds, but also includes chemical groups leading to an ionic interaction or hydrogen bonds with the antigen-MHC-co-stimulatory molecule complex. Moreover, it should be noted that a strict distinction between "functional groups" generated at the surface and linking molecules bearing "functional groups" is not possible, since sometimes the modification of the surface requires the reaction of smaller linking molecules such as ethylene glycol with the nanoparticle surface.

The functional groups or the linking molecules bearing them may be selected from amino groups, carbonic acid groups, thiols, thioethers, disulfides, guanidino, hydroxyl groups, amine groups, vicinal dioles, aldehydes, alpha-haloacetyl groups, mercury organyles, ester groups, acid halide, acid thioester, acid anhydride, isocyanates, isothiocyanates, sulfonic acid halides, imidoesters, diazoacetates, diazonium salts, 1,2-diketones, phosphonic acids, phosphoric acid esters, sulfonic acids, azolides, imidazoles, indoles, N-maleimides, alpha-beta-unsaturated carbonyl compounds, arylhalogenides or their derivatives.

Non-limiting examples for other linking molecules with higher molecular weights are nucleic acid molecules, polymers, copolymers, polymerizable coupling agents, silica, proteins, and chain-like molecules having a surface with the opposed polarity with respect to the substrate or nanoparticle. Nucleic acids can provide a link to affinity molecules containing themselves nucleic acid molecules, though with a complementary sequence with respect to the linking molecule.

As examples for polymerizable coupling agents, diacetylene, styrene butadiene, vinylacetate, acrylate, acrylamide, vinyl compounds, styrene, silicone oxide, boron oxide, phosphorous oxide, borates, pyrrole, polypyrrole and phosphates can be cited.

The surface of the substrate or nanoparticle can be chemically modified, for instance by the binding of phosphonic acid derivatives having functional reactive groups. One example of these phosphonic acid or phosphonic acid ester derivates is imino-bis(methylenphosphono) carbonic acid which can be synthesized according to the "Mannich-Moedritzer" reaction. This binding reaction can be performed with substrate or nanoparticle as directly obtained from the preparation process or after a pre-treatment (for instance with trimethylsilyl bromide). In the first case the phosphonic acid (ester) derivative may for instance displace components of the reaction medium which are still bound to the surface. This displacement can be enhanced at higher temperatures. Trimethylsilyl bromide, on the other hand, is believed to dealkylate alkyl group-containing phosphorous-based complexing agents, thereby creating new binding sites for the phosphonic acid (ester) derivative. The phosphonic acid (ester) derivative, or linking molecules bound thereto, may display the same functional groups as given above. A further example of the surface treatment of the substrate or nanoparticle involves heating in a diole such as ethylene glycol. It should be noted that this treatment may be redundant if the synthesis already proceeded in a diole. Under these circumstances the synthesis product directly obtained is likely to show the necessary functional groups. This treatment is however applicable to substrate or nanoparticle that were produced in N- or P-containing complexing agents. If such substrate or particle are subjected to an after-treatment with ethylene glycol, ingredients of the reaction medium (e.g. complexing agent) still binding to the surface can be replaced by the diole and/or can be dealkylated.

It is also possible to replace N-containing complexing agents still bound to the particle surface by primary amine derivatives having a second functional group. The surface of the substrate or nanoparticle can also be coated with silica. Silica allows a relatively simple chemical conjugation of organic molecules since silica easily reacts with organic linkers, such as triethoxysilane or chlorosilane. The nanoparticle surface may also be coated by homo- or copolymers. Examples for polymerizable coupling agents are. N-(3-aminopropyl)-3-mercaptobenzamidine, 3-(trimethoxysilyl)propylhydrazide and 3-trimethoxysilyl)propylmaleimide. Other non-limiting examples of polymerizable coupling agents are mentioned herein. These coupling agents can be used singly or in combination depending on the type of copolymer to be generated as a coating.

Another surface modification technique that can be used with substrates or nanoparticles containing oxidic transition metal compounds is conversion of the oxidic transition metal compounds by chlorine gas or organic chlorination agents to the corresponding oxychlorides. These oxychlorides are capable of reacting with nucleophiles, such as hydroxy or amino groups as often found in biomolecules. This technique allows generating a direct conjugation with proteins, for instance-via the amino group of lysine side chains. The conjugation with proteins after surface modification with oxychlorides can also be effected by using a bi-functional linker, such as maleimidopropionic acid hydrazide.

For non-covalent linking techniques, chain-type molecules having a polarity or charge opposite to that of the substrate or nanoparticle surface are particularly suitable. Examples for linking molecules which can be non-covalently linked to core/shell nanoparticle involve anionic, cationic or zwitter-ionic surfactants, acid or basic proteins, polyamines, polyamides, polysulfone or polycarboxylic acid. The hydrophobic interaction between substrate or nanoparticle and amphiphilic reagent having a functional reactive group can generate the necessary link. In particular, chain-type molecules with amphiphilic character, such as phospholipids or derivatised polysaccharides, which can be crosslinked with each other, are useful. The absorption of these molecules on the surface can be achieved by coincubation. The binding between affinity molecule and substrate or nanoparticle can also be based on non-covalent, self-organising bonds. One example thereof involves simple detection probes with biotin as linking molecule and avidin- or strepdavidin-coupled molecules.

Protocols for coupling reactions of functional groups to biological molecules can be found in the literature, for instance in "Bioconjugate Techniques" (Greg T. Hermanson, Academic Press 1996). The biological molecule (e.g., MHC molecule or derivative thereof) can be coupled to the linking molecule, covalently or non-covalently, in line with standard procedures of organic chemistry such as oxidation, halogenation, alkylation, acylation, addition, substitution or amidation. These methods for coupling the covalently or non-covalently bound linking molecule can be applied prior to the coupling of the linking molecule to the substrate or nanoparticle or thereafter. Further, it is possible, by means of incubation, to effect a direct binding of molecules to correspondingly pre-treated substrate or nanoparticles (for instance by trimethylsilyl bromide), which display a modified surface due to this pre-treatment (for instance a higher charge or polar surface).

F. Protein Production

The present invention describes polypeptides, peptides, and proteins for use in various embodiments of the present invention. For example, specific peptides and their complexes are assayed for their abilities to elicit or modulate an immune response. In specific embodiments, all or part of the peptides or proteins of the invention can also be synthesized in solution or on a solid support in accordance with conventional techniques. Various automatic synthesizers are commercially available and can be used in accordance with known protocols. See, for example, Stewart and Young (1984); Tam et al. (1983); Merrifield (1986); and Barany and Merrifield (1979), each incorporated herein by reference. Alternatively, recombinant DNA technology may be employed wherein a nucleotide sequence which encodes a peptide of the invention is inserted into an expression vector, transformed or transfected into an appropriate host cell and cultivated under conditions suitable for expression.

One embodiment of the invention includes the use of gene transfer to cells, including microorganisms, for the production of proteins. The gene for the protein of interest may be transferred into appropriate host cells followed by culture of cells under the appropriate conditions. A nucleic acid encoding virtually any polypeptide may be employed. The generation of recombinant expression vectors, and the elements included therein, are known to one skilled in the art and are briefly discussed herein. Examples of mammalian host cell lines include, but are not limited to Vero and HeLa cells, other B- and T-cell lines, such as CEM, 721.221, H9, Jurkat, Raji, as well as cell lines of Chinese hamster ovary, W138, BHK, COS-7, 293, HepG2, 3T3, RIN and MDCK cells. In addition, a host cell strain may be chosen that modulates the expression of the inserted sequences, or that modifies and processes the gene product in the manner desired. Such modifications (e.g., glycosylation) and processing (e.g., cleavage) of protein products may be important for the function of the protein. Different host cells have characteristic and specific mechanisms for the post-translational processing and modification of proteins. Appropriate cell lines or host systems can be chosen to ensure the correct modification and processing of the foreign protein expressed. In some instances, proteins of the present invention may be expressed and purified from *Drosophila* cells.

A number of selection systems may be used including, but not limited to HSV thymidine kinase, hypoxanthine-guanine phosphoribosyltransferase, and adenine phosphoribosyltransferase genes, in tk-, hgprt- or aprt-cells, respectively. Also, anti-metabolite resistance can be used as the basis of selection: for dhfr, which confers resistance to trimethoprim and methotrexate; gpt, which confers resistance to mycophenolic acid; neo, which confers resistance to the aminoglycoside G418; and hygro, which confers resistance to hygromycin.

G. Nucleic Acids

The present invention may include recombinant polynucleotides encoding the proteins, polypeptides, peptides of the invention. As used in this application, the term "polynucleotide" refers to a nucleic acid molecule that either is recombinant or has been isolated free of total genomic nucleic acid. Included within the term "polynucleotide" are oligonucleotides (nucleic acids 100 residues or less in length), recombinant vectors, including, for example, plasmids, cosmids, phage, viruses, and the like. Polynucleotides include, in certain aspects, regulatory sequences, isolated substantially away from their naturally occurring genes or protein encoding sequences. Polynucleotides may be RNA, DNA, analogs thereof, or a combination thereof.

In this respect, the term "gene," "polynucleotide," or "nucleic acid" is used to refer to a nucleic acid that encodes a protein, polypeptide, or peptide (including any sequences required for proper transcription, post-translational modification, or localization). As will be understood by those in the art, this term encompasses genomic sequences, expression cassettes, cDNA sequences, and smaller engineered nucleic acid segments that express, or may be adapted to express, proteins, polypeptides, domains, peptides, fusion proteins, and mutants. A nucleic acid encoding all or part of a polypeptide may contain a contiguous nucleic acid sequence encoding all or a portion of such a polypeptide of the following lengths: 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1010, 1020, 1030, 1040, 1050, 1060, 1070, 1080, 1090, 1095, 1100, 1500, 2000, 2500, 3000, 3500, 4000, 4500, 5000, 5500, 6000, 6500, 7000, 7500, 8000, 9000, 10000, or more nucleotides, nucleosides, or base pairs. It also is contemplated that a particular polypeptide from a given species may be encoded by nucleic acids containing natural variations that having slightly different nucleic acid sequences but, nonetheless, encode the same or substantially similar protein, polypeptide, or peptide.

In particular embodiments, the invention concerns isolated nucleic acid segments and recombinant vectors incorporating nucleic acid sequences that encode a tumor-specific antigen and/or a MHC molecule. The term "recombinant" may be used in conjunction with a polypeptide or the name of a specific polypeptide, and this generally refers to a polypeptide produced from a nucleic acid molecule that has been manipulated in vitro or that is a replication product of such a molecule.

The nucleic acid segments used in the present invention, regardless of the length of the coding sequence itself, may be combined with other nucleic acid sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant nucleic acid protocol. In some cases, a nucleic acid sequence may encode a polypeptide sequence with additional heterologous coding sequences, for example to allow for purification of the polypeptide, transport, secretion, post-translational modification, or for therapeutic benefits such as targeting or efficacy. A tag or other heterologous polypeptide may be added to the modified polypeptide-encoding sequence, wherein "heterologous" refers to a polypeptide that is not the same as the modified polypeptide.

IV. Therapeutic Targets

A method of the present invention includes treatment for a disease or condition caused by neoplasm of cells of the body. An immunogenic polypeptide of the invention can be given to induce or modify an immune response in a person having, suspected of having, or at risk of developing cancer, neoplasm of cells, or a tumor. Methods may be employed with respect to individuals who have tested positive for antigen immuno-reactivity or who are deemed to be at risk for developing such a condition or related condition.

The cancerous and/or neoplastic conditions encompassed by this invention are not limited to any specific cell type or specific cancer but include any cancer in which a tumor-specific antigen is present in said cancerous cells. Additionally, the cancerous cell or precancerous cell must be located such that it is amenable to an immune response induced by the compositions and methods of the present invention. Some examples of such cancers include but are not limited to adrenocortical carcinoma; bladder cancer; breast cancer; breast cancer, ductal; breast cancer, invasive intraductal; breast-ovarian cancer; Burkitt's lymphoma; cervical carcinoma; colorectal adenoma; colorectal cancer; colorectal cancer, hereditary nonpolyposis, type 1; colorectal cancer, hereditary nonpolyposis, type 2; colorectal cancer, hereditary nonpolyposis, type 3; colorectal cancer, hereditary nonpolyposis, type 6; colorectal cancer, hereditary nonpolyposis, type 7; dermatofibrosarcoma protuberans; endometrial carcinoma; esophageal cancer; gastric cancer, fibrosarcoma, glioblastoma multiforme; glomus tumors, multiple; hepatoblastoma; hepatocellular cancer; hepatocellular carcinoma; leukemia, acute lymphoblastic; leukemia, acute myeloid; leukemia, acute myeloid, with eosinophilia; leukemia, acute nonlymphocytic; leukemia, chronic myeloid; Li-Fraumeni syndrome; liposarcoma; lung cancer; lung cancer, small cell; lymphoma, non-Hodgkin's; lynch cancer family syndrome II; male germ cell tumor; mast cell leukemia; medullary thyroid; medulloblastoma; melanoma, meningioma; multiple endocrine neoplasia; myeloid malignancy, predisposition to; myxosarcoma, neuroblastoma; osteosarcoma; ovarian cancer; ovarian cancer, serous; ovarian carcinoma; ovarian sex cord tumors; pancreatic cancer; pancreatic endocrine tumors; paraganglioma, familial non-chromaffin; pilomatricoma; pituitary tumor, invasive; prostate adenocarcinoma; prostate cancer; renal cell carcinoma, papillary, familial and sporadic; retinoblastoma; rhabdoid predisposition syndrome, familial; rhabdoid tumors; rhabdomyosarcoma; small-cell cancer of lung; soft tissue sarcoma, squamous cell carcinoma, head and neck; T-cell acute lymphoblastic leukemia; Turcot syndrome with glioblastoma; tylosis with esophageal cancer; uterine cervix carcinoma; colon-rectal cancer; lung cancer; prostate cancer; skin cancer; osteocarcinoma; solid tumors/malignancies; myxoid and round cell carcinoma; locally advanced tumors; human soft tissue carcinoma; cancer metastases; squamous cell carcinoma; esophageal squamous cell carcinoma; oral carcinoma; cutaneous T cell lymphoma; Hodgkin's lymphoma; non-Hodgkin's lymphoma; cancer of the adrenal cortex; ACTH-producing tumors; non-small cell cancers; gastrointestinal cancers; urological cancers; malignancies of the female genital tract; malignancies of the male genital tract; kidney cancer; brain cancer; bone cancers; skin cancers; thyroid cancer; retinoblastoma; peritoneal effusion; malignant pleural effusion; mesothelioma; Wilms's tumors; gall bladder cancer; trophoblastic neoplasm; hemangiopericytoma; Kaposi's sarcoma and liver cancer.

V. Examples

The following examples are given for the purpose of illustrating various embodiments of the invention and are not meant to limit the present invention in any fashion. One skilled in the art will appreciate readily that the present invention is well adapted to carry out the objects and obtain the ends and advantages mentioned, as well as those objects, ends and advantages inherent herein. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1

Figure 1:
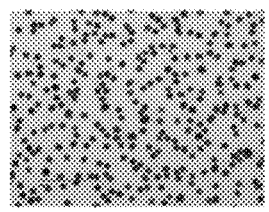
FIG. 1 depicts a representative TEM image. pMHC-coated GNPs (Gold Nanoparticles) (14 nm) are concentrated at high densities ($\sim 5 \times 10^{13}$/ml) and monodispersed. Mag: 50,000×.

Synthesis and characterization of gold-based pMHC-NPs. Gold nanoparticles (GNPs) of specific sizes can be synthesized according to Levy, R. et al. ("Rational and combinatorial design of peptide capping ligands for gold nanoparticles." J Am Chem Soc 126, 10076-84 (2004)). The size, density, charge and monodispersity of the GNP preparations are measured using spectrophotometry, transmission electron microscopy (TEM) and dynamic light scattering. The GNP samples are then concentrated and conjugated with pMHCs (antigen-MHC complex) using different approaches. Methods to quantitate the pMHC valency/GNP and to concentrate the antigen=MHC-GNPs at high densities ($\sim 10^{14}$/ml) without compromising monodispersion were developed (FIG. 1).

Example 2 pMHC-binding capacity of GNPs. pMHCs were coated onto GNPs of various sizes using two approaches: (i) random binding of pMHC to the GNP via electrostatic interactions; and (ii) directional binding through a thiol-PEG-NH$_2$ linker. In this case, an additional thiol-PEG as a GNP stabilizer is used to prevent aggregation. It is contemplated that the first approach would enable very high ligand densities while compromising the directionality of pMHC binding (i.e. only a fraction of pMHCs would be available for recognition by cognate T-cells). The second approach aimed to generate pMHC-GNPs carrying fewer pMHCs but bound directionally, via their C-termini. Both approaches on 14 to 40 nm GNPs were tested. It was confirmed that, for both approaches, the pMHC-binding capacity of GNPs is a function of surface area. Accordingly, more pMHCs were bound when the nanoparticles were of a larger size. Surprisingly, it was found that PEG mediated-binding not only ensures the directionality of binding but also enhances the binding capacity of individual GNPs (contrary to our initial expectation). Table 1 summarizes these results.

TABLE I pMHC-binding capacity of GNPs

| Diameter (nm) | S Surface area: ($\times 10^2$ nm$^2$) | pMHCs/GNP (adsorption) | pMHCs/GNP (linker) |
|---|---|---|---|
| 14 | 7 | N | 212 |
| 20 | 12 |  | 3,750 |
| 30 | 28 | 335 |  |
| 40 | 50 | 2,850 | 5,250 |

Example 3

Figure 2:
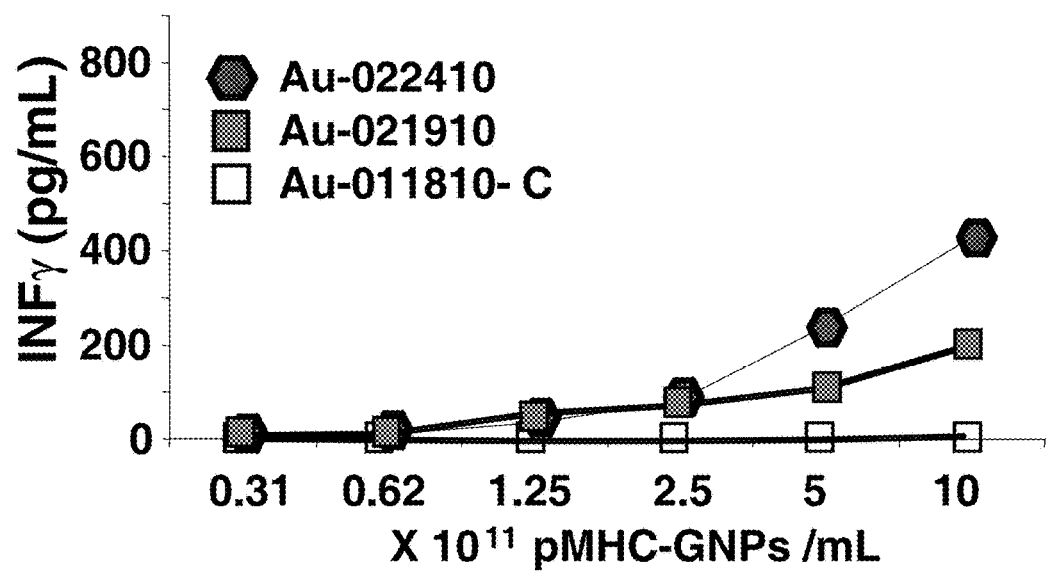
FIG. 2 represents the effects of pMHC (GNP) dose and pMHC valency on the agonistic properties of pMHC-coated GNPs. The figure compares the amounts of IFNγ secreted by cognate 8.3-CD8+ T-cells in response to two different pMHC-GNP samples (both consisting of $\sim 2 \times 10^{13}$ GNPs of 14 nm in diameter/ml). Au-022410 and Au-21910 carried ~250 and ~120 pMHCs/GNP, respectively. Au-011810-C carried ~120 control pMHCs/GNP.

Agonistic activity vs. pMHC content. The effects of pMHC valency, GNP size, GNP density and coating strategy on the agonistic activity of pMHC-GNPs in vitro were tested. The ability of various IGRP$_{206-214}$-K$^d$-GNP preparations to activate cognate (IGRP$_{206-214}$-specific) naive CD8+ T-cells (herein referred to as '8.3-CD8+ T-cells') derived from 8.3-T-cell receptor (TCR) transgenic NOD mice was compared. The first set of experiments compared the effects of IGRP$_{206-214}$-K$^d$ (pMHC) valency over a range of GNP densities. GNPs coated with a control (non-cognate) pMHC (Tum-K$^d$) were used as negative controls. As expected, IGRP$_{206-214}$-K$^d$-(but not TUM-K$^d$) GNPs activated these T-cells (as measured by IFNγ production) in a pMHC dose-dependent manner. FIG. 2 shows an experiment with 14 nm GNPs coated with different numbers of pMHCs via the linker method. In addition, GNPs coated with ~2-fold higher numbers of pMHCs had superior agonistic activity. Thus, the agonistic activity of pMHC-GNPs is a function of total pMHC content.

Example 4

Figure 3:
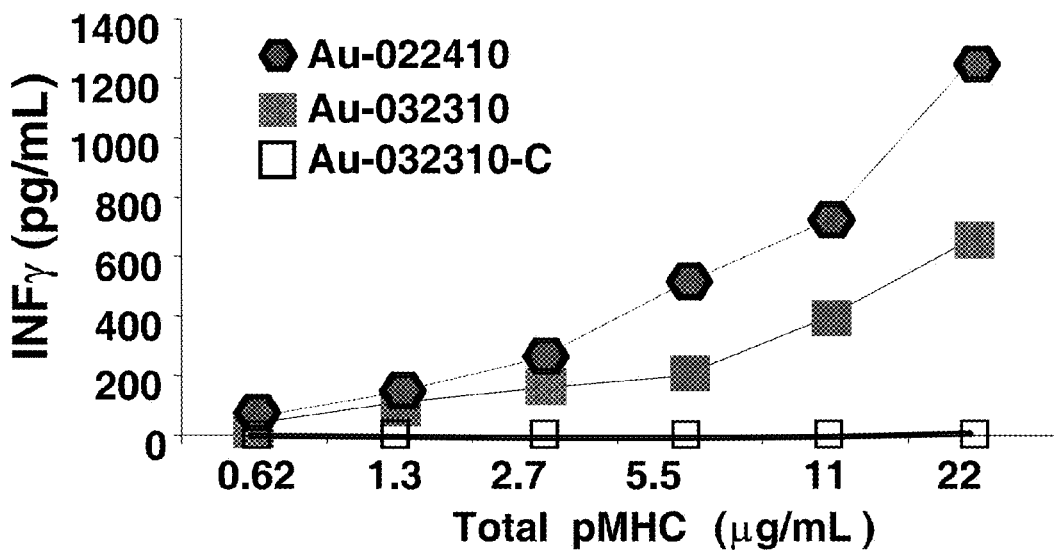
FIG. 3 depicts the effect of size on agonistic activity. Au-022410 were 14 nm GNPs coated with a relatively low pMHC valency but prepared at a high density; Au-032310 were 40 nm GNPs coated with high pMHC valency but at low density. Au-022410 had superior agonistic activity than the Au-032310 sample. Au-032310-C are NPs coated with TUM/$K^d$ (negative control pMHC).

Agonistic activity vs. GNP size and density. Further analyses indicated that total pMHC content is not the only factor affecting the agonistic activity of pMHC-GNPs and that GNP size is also important. This was tested by comparing the activity of two pMHC-GNP samples of different size (14 and 40 nm) and different pMHC valencies but similar pMHC content. In the experiment shown in FIG. 3, 14 nm GNPs carrying ~200 pMHCs/GNP, and 40 nm GNPs carrying ~5,000 pMHCs/GNP were used. The GNP densities of these two samples were adjusted to 3×10$^{13}$ and 10$^{12}$ GNPs/mL respectively, to adjust the total pMHC content to ~450 ug/ml. Notably, 8.3-CD8+ cells responded significantly better to the 14 nm pMHC/GNP compound than to the 40 nm one over a range of total pMHC contents, despite that the latter carried more pMHCs/GNP. This suggested that GNP density (more GNPs/cognate T-cell) is key. For example, 4×40 nm NPs carrying 1000 pMHCs/GNP (4000 pMHCs) would be less desirable than 40×10 nm NPs carrying 100 pMHCs/GNP (4000 pMHCs).

Taken together, these data suggest that optimal pMHC-GNP preparations are those comprised of small GNPs used at high densities. The advantages of increasing pMHC valency above a certain level (i.e. 25 pMHCs/GNP) are less significant.

Example 5

Figure 4:
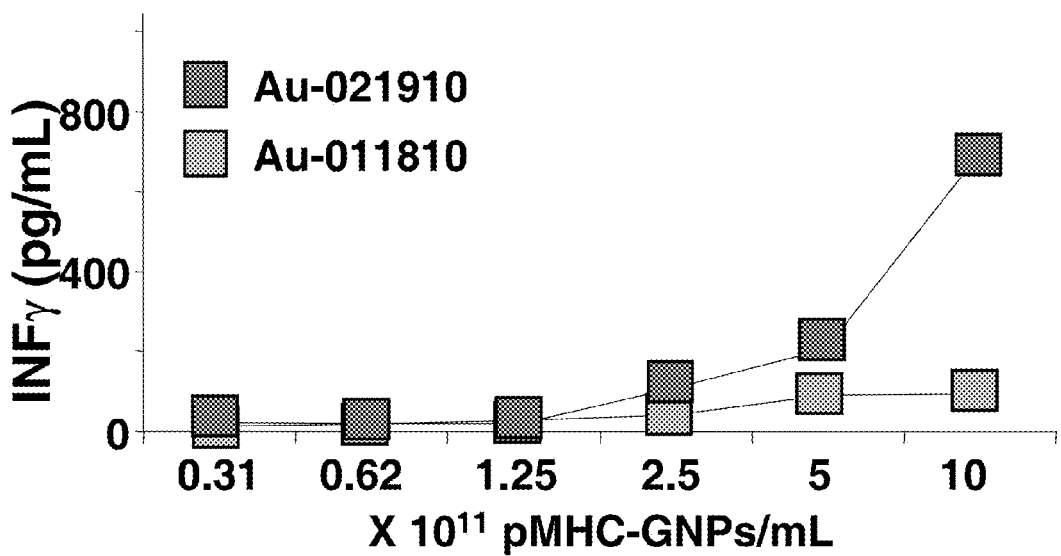
FIG. 4 shows the effect of protective PEGs on the function of pMHC-GNPs. Au-021910 consisted of $\sim 2 \times 10^{13}$ GNPs of 14 nm in diameter/ml protected by 2 kD thiol-PEGs and coated with ~120 pMHCs/GNP. Au-011810 GNPs (also $\sim 2 \times 10^{13}$ 14 nm GNPs/ml) were protected by 5 kD thiol-PEGs and were coated with ~175 pMHCs/GNP. Sample Au-021910 clearly had superior agonistic activity.

Agonistic activity vs. pMHC exposure. As noted above, the pMHC-GNP samples are produced by co-coating GNPs with a 3.4 kD thiol-PEG-NH$_2$ linker (as acceptor of pMHC carboxitermini) with a thiol-PEG linker that functions as a GNP stabilizer. To determine if the length of the stabilizing thiol-PEG influences its GNP anti-aggregation properties, the ability of the thiol-PEG-NH$_2$ to bind pMHCs and/or the agonistic properties of pMHC-GNPs, pMHC-GNPs prepared using stabilizing linkers of different sizes (2 kD and 5 kD, shorter and longer than the pMHC-acceptor, respectively) were compared. Both linkers had similar anti-aggregation properties, and the 5 kD linker did not inhibit binding of pMHC to the shorter 3.4 kD thiol-PEG-NH$_2$. Notably, however, pMHC-GNPs protected by the shorter (2 kD) thiol-PEG had superior agonistic activity than those co-coated with the longer (5 kD) thiol-PEG (FIG. 4). This suggests that long protective thiol-PEG linkers shield pMHC molecules bound to the acceptor linker from T-cell exposure.

Example 6

Expansion of autoregulatory CD8+ cells by pMHC-GNPs in vivo: a key role for coating strategy. The ability of several different IGRP$_{206-214}$-K$^d$-GNP samples to expand cognate autoregulatory CD8+ cells in vivo was tested. pMHC-GNPs were injected by i.v. into 10 wk-old NOD mice. Each received 2 weekly injections for 5 wk. Changes in the size of the cognate T-cell population in blood and lymphoid organs were assessed by staining cell suspensions with fluorescently-labeled pMHC tetramers. Two 30 nm pMHC/GNP samples (at ~1.8-2.2×10$^{13}$ GNPs/ml) that had been coated at high pMHC valencies by direct adsorption (300-600 pMHCs/GNP) (10 ul of GNP/injection) were first tested. Both samples exhibited agonistic activity in vitro (not shown). However, neither was able to induce expansion of cognate autoregulatory CD8+ cells in blood or lymphoid organs (not shown), likely because the pMHCs were rapidly dislodged from the GNP scaffold in vivo.

Figure 5:
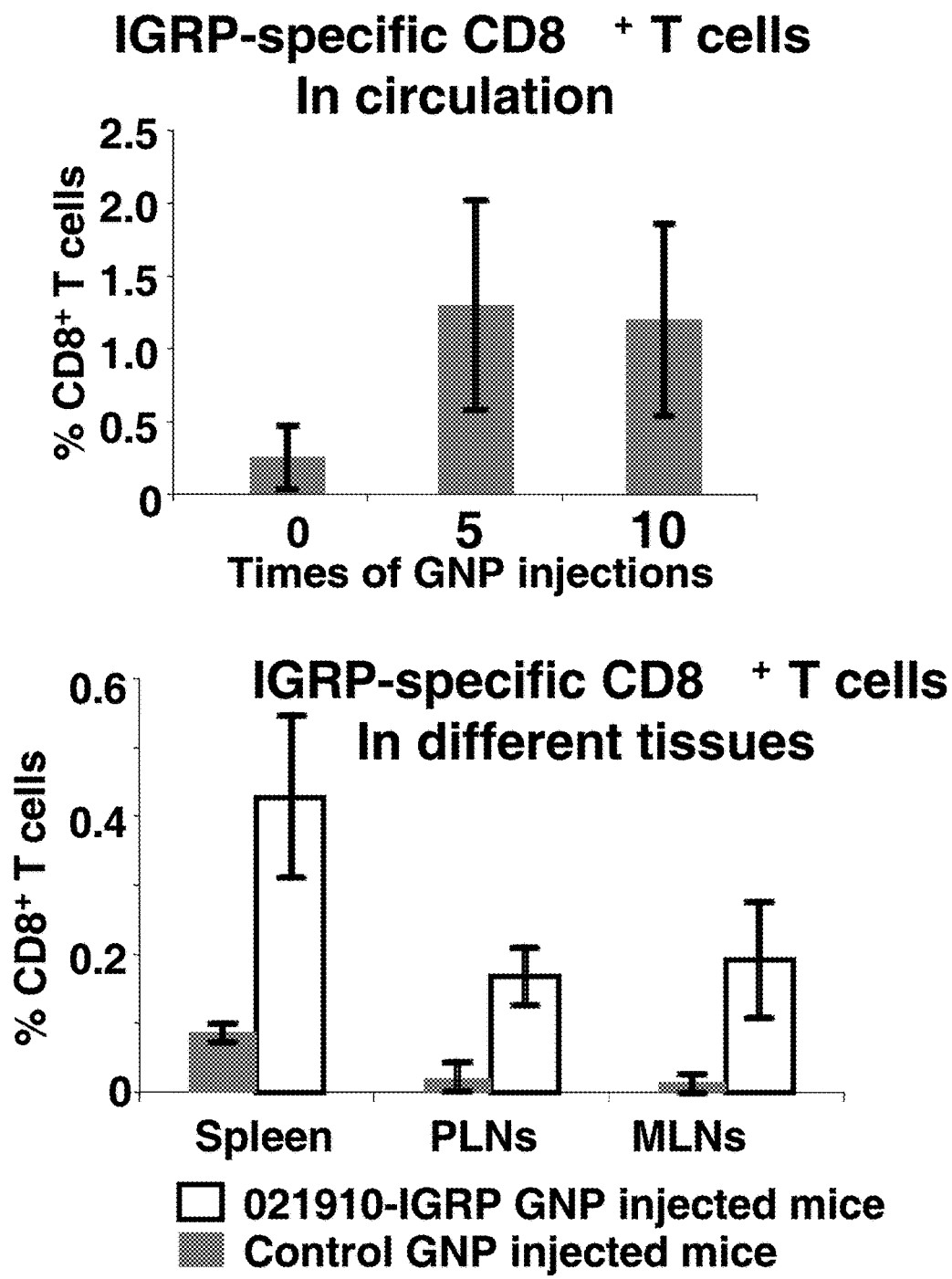
FIG. 5 depicts In vivo expansion of cognate autoregulatory CD8+ T cells by directionally-coated IGRP$_{206-214}$-$K^d$-GNPs. Average % of CD8+ T-cells in blood or lymphoid organs (pancreatic or mesenteric lymph nodes—PLN and MLN, respectively—) that bind IGRP$_{206-214}$-$K^d$ tetramers (n=3 mice). Control pMHC-GNPs were GNPs prepared the same way but coated with a disease-irrelevant pMHC complex (TUM/$K^d$).

Two 14 nm pMHC-GNP samples at similar NP densities but coated at lower valencies (40-100 pMHCs/GNP) via PEG linkers were tested. Unlike the case for pMHC-GNPs produced by the adsorption method, injections (10 µl/dose) of these pMHC-GNPs induced significant expansions of cognate T-cells in both blood and lymphoid organs (FIG. 5). These expansions were antigen-specific, since GNPs conjugated with control pMHCs did not induce expansion, even at higher doses (100 µl/dose). Thus, pMHC-GNPs of small diameter (14 nm) covalently coated with pMHC via appropriate PEG linkers and used at sufficiently high numbers are capable of expanding cognate autoregulatory CD8+ cells in vivo.

Example 7

Figure 6:
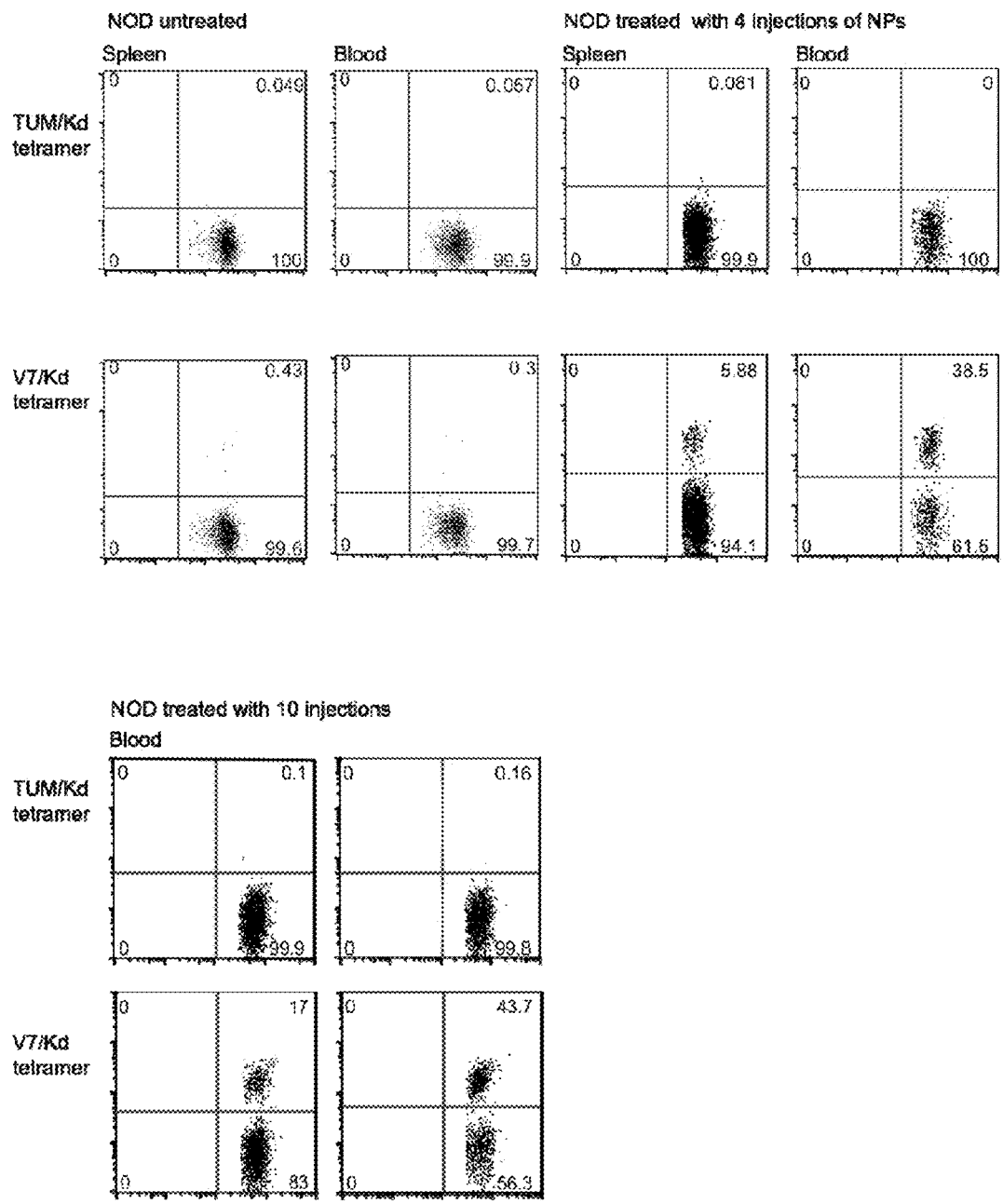
FIG. 6 depicts massive expansion of cognate CD8+ T-cells in mice treated with pMHC-coated NPs. Upper panel: profile of a mouse sacrificed after 4 doses. Bottom panel: profile of two different mice after 10 injections (blood only; alive at the time of this submission).

Massive expansion of cognate CD8+ T-cells by pMHC-GNPs coated at higher pMHC valencies. It was next determined whether pMHC-NPs have the potential to induce massive expansions of cognate T-cells in vivo. This was done by treating mice with several injections of $3\times10^{12}$ 10-14 nm NPs carrying 25 ug of total pMHC (~150 IGRP$_{206-214}$/Kd molecules per NP). As shown in FIG. 6, mice treated with 10 doses (twice a week for 10 week) displayed massive expansions of cognate IGRP$_{206-214}$ (NRP-V7)-reactive CD8+ T-cells in peripheral blood as compared to their untreated counterparts (from <0.4 to >17 or 47% CD8+ T-cells) (lower panels). Such expansion was already seen in a mouse that was sacrificed after 4 doses of pMHC-NPs (upper panels). The pMHC-NP-expanded cells specifically bound cognate but not non-cognate pMHC tetramers (NRP-V7/$K^d$ vs. TUM/$K^d$, respectively).

Example 8

To co-opt the optimal pMHC-GNP design to develop 'multiplexed' NPs with co-stimulatory properties. One example of a co-stimulatory molecule is IL-15/IL-15Ra. For example, IL-15 is required for the maintenance of memory CD8+ T-cell responses (for example see Kennedy, M. K. et al. "Reversible defects in natural killer and memory CD8 T cell lineages in interleukin 15-deficient mice." J Exp Med 191, 771-80 (2000) and Becker, T. et al., "Interleukin 15 is required for proliferative renewal of virus-specific memory CD8 T cells." J. Exp. Med. 195, 1541-1548 (2002) which are herein incorporated by reference). Trans-presentation of IL-15 by membrane IL-15Ra on APCs sustains the survival of memory CD8+ T-cells and enhances their proliferation during antigenic recall responses (see for example Sato, N. et al., "The IL-15/IL-15Ralpha on cell surfaces enables sustained IL-15 activity and contributes to the long survival of CD8 memory T cells." Proc Natl Acad Sci USA 104, 588-93 (2007) and Mortier, E. et al. "Macrophage- and dendritic-cell-derived interleukin-15 receptor alpha supports homeostasis of distinct CD8+ T cell subsets." Immunity 31, 811-22 (2009) which are herein incorporated by reference.) Accordingly, it is contemplated that pMHC-NPs displaying IL-15/IL-15Ra complexes will have superior memory T-cell expansion properties than NPs coated with pMHC alone. Therefore, it would be possible to achieve similar or better effects at significantly lower doses of total pMHC and NP. In one embodiment of the multiplexed pMHC-NP platform, NPs would carry both pMHC and a recombinant IL-15/IL-15Ra-hFc fusion at different stoichiometries (range: 1:25 to 25:1).

In one example, a mIL-15 cDNA fragment encoding residues N49-S162 was fused with a mIL-15Ra cDNA encoding residues G33-A132 via a flexible GS linker. This IL-15/IL-15Ra cDNA was then fused with cDNA encoding the Fc portion of human IgG (hFc). We subcloned this construct into a fly cell expression vector, which was transfected into *Drosophila melanogaster* SC2 cells along with a puromycine resistance gene to generate stable cell lines. Recombinant proteins were purified from supernatants by Protein A affinity chromatography. A similar design can be applied to other co-stimulatory molecules (i.e. to generate dimers of dimers or trimers fused to the Fc portion of IgG).

Example 9. Preparation of pMHc Conjugated Gold NanoParticles pMHC conjugated Gold NanoParticle Preparation (pMHC-GNPs, 12 and 30 nm). Preparation of GNPs. GNPs were prepared by heating D.D. water (200 mL) in a ball flask in a silicon oil bath till boiling. A solution of 1% HAuCL$_4$ (4 mL) was then added into boiling water. The solution was stirred for 10 min before adding of 1% Na Citrate solution. For 12 nm GNPs, 12 mL Na Citrate solution was added. For 30 nm GNPs, 12 mL Na Citrate solution was added. A wine color appears immediately after adding Na Citrate solution. To complete the reaction, GNP solution was stirred for 30 minutes more. This is a modification of the method described in Levy, R. et al. ("Rational and combinatorial design of peptide capping ligands for gold nanoparticles." J Am Chem Soc 126, 10076-84 (2004)) which is herein incorporated by reference.

Surface modification of GNPs. GNPs were pegylated by addition of 25 mM thiol-PEG-NH$_2$ (M.W. 3,400) and 50 mM thiol-PEG (M. W. 2,000, PEG/GNP ratio 10,000:1) into GNP solution. The solution was stirred for 5 hours at room temperature. Pegylated GNPs were then washed with 3×30 mL sterilized D. D. water to remove excess PEGs, and resuspended in 40 mL of 100 mM MES ($C_6H_{13}NO_4S.xH_2O$) buffer, pH 5.5.

pMHC conjugation. pMHCs (IGRP$_{206-214}$/Kd, 4 mg) was added into solution of pegylated GNPs, drop-by-drop with mild stirring at room temperature. The mixture is stirred for one hour before the addition of 20 mg 1-Ethyl-3-(3-dimethylaminopropyl) carbodiimide (EDC). The mixture is stirred for additional 4 hrs. pMHC-GNPs conjugates are then washed with 40 mL Phosphate Buffered Saline (PBS, PH 7.2-7.4) for three times, and resuspended in 8 mL PBS.

Example 10. Preparation of pMHC Conjugated Gold NanoParticles

Preparation of pMHC conjugated GNPs (pMHC-GNPs, 2-10 nm). Prepare GNPs (2-5 nm). GNPs of 2-5 nm were prepared by dissolving 250 mg (for 2 nm GNPs) or 50 mg (for 4 nm GNPs) Dodecylamine in 10 mL of DDAB solution (100 mM Didodecyldimethylammonium bromide (DDAB) in Toluene). Secondly, 100 mg Tetrabutylammonium borohydride (TBAB) was dissolved in 4 mL of DDAB solution. Solutions of Dodecylamine and TBAB were then mixed in a 50 mL three-neck flask, stirring under nitrogen. 34 mg AuCl$_3$ was resolved in 4.5 mL DDAB solution, and injected quickly into a mixture of TBAB and Dodecylamine solution. Solution becomes deep red immediately, indicating the formation of GNPs. The mixture was continuously stirred for 30 min, and 15 mLs of ethanol were added into the mixture. The mixture was then spun at 4,100×g for 12 min to precipitate GNPs.

Prepare GNPs (6-10 nm). To prepare GNPs of 6-10 nm Decanoic acid (172 mg) was first dissolved in 10 mL Toluene, and then mixed with various amounts of TBAB solution (4 and 1 mL for 6 and 10 nm GNPs, respectively) in a 50 mL three-neck flask, when stirring under nitrogen. AuCl$_3$ (34 mg dissolved in 4.5 mL DDAB stock solution) was then quickly injected into the mixture of TBAB and Decanoic acid solution. The solution became deep red immediately. The mixture was continuously stirred for 30 min, and 15 mL ethanol was added into the mixture. The mixture is then spun at 4,100×g for 12 min to precipitate GNPs.

Surface modification of GNPs. GNPs were resuspended in 20 mL of 0.1 M mercaptopropanoic acid (WA) in methanol, pH 10 and stirred for one hour at room temperature. 10 mL ethyl acetate was then added. The mixture was then spun at 4,100×g for 15 min. The precipitated GNPs were then washed with 30 mL sterilized D.D. water for three times, and resuspended in 20 mL 100 mM MES ($C_6H_{13}NO_4S.xH_2O$) buffer, pH 5.5. To this mixture, solutions of 0.5 M Polyoxyethylene bis(amine) (at 10,000:1 PEG/GNP ratio) and 0.1M 1-Ethyl-3-(3-dimethylaminopropyl) carbodiimide (EDC) (final EDC concentration 2 mM) were added. The mixture was then stirred for 4 hours. The pegylated GNPs were washed with 3×30 mL sterilized D.D. water to remove excess PEG and EDC.

pMHC conjugation. Pegylated GNPs were resuspended in 20 mL 100 mM MES ($C_6H_{13}NO_4S.xH_2O$) buffer, pH 5.5. pMHCs (5 mg/mL, total 10-30 mg) were then added to resuspended GNPs (500:1 pMHC/GNP ratio), drop-by-drop, and stirred for 1 hour at room temperature before adding 0.1M 1-Ethyl-3-(3-dimethylaminopropyl) carbodiimide (EDC) (final EDC concentration 2 mM). The mixture was stirred for 4 more hours. pMHC-GNPs conjugates were washed three with 40 mL Phosphate Buffered Saline (PBS, PH 7.2-7.4), and then resuspended in 10-20 mL PBS.

Example 11. Preparation, Characterization, and Functional Assays of Iron Oxide Nanoparticles Conjugated with $IGRP_{206-214}/K^d$ and an Agonistic Anti-CD28 Antibody, to Potentiate the Activation of Naive Cognate CD8+ T-Cells Iron Oxide nanoparticles ($Fe_3O_4$ NPs) were synthesized using a thermal-decomposition method, and the size of the NPs was measured using transmission electron microscopy (TEM) (9.4 nm).

The synthesized particles were then conjugated with functionalized dopamine-PEG linkers of 3.4 KD designed to both stabilize the nanoparticles and function as acceptors of lymphocyte stimulatory ligands. These peggylated nanoparticles were then conjugated with an agonistic anti-CD28 monoclonal antibody (clone 37.51 mAb; a lymphocyte activating receptor for the costimulatory molecule B7.1) and/or multiple copies of a peptide-major histocompatibility complex (pMHC) targeted by a significant population of CD8+ T-cells in nonobese diabetic (NOD) mice ($IGRP_{206-214}/K^d$). The nanoparticle density was determined by measuring the iron content in the samples. The valency of pMHC and antibody in the pMHC/anti-CD28 mAb-conjugated nanoparticle preparations was determined by a dot-ELISA method employing MHC and IgG-specific antibodies as detecting reagents for pMHC and anti-CD28 mAb, respectively. FIGS. 7 and 8 show representative TEM images showing that both pMHC/anti-CD28 mAb- (FIG. 7) and pMHC-conjugated nanoparticle preparations (FIG. 8) were monodispesed and had similar iron (nanoparticle) contents and pMHC valencies.

The results of agarose gel electrophoresis analyses showed that control unconjugated nanoparticles contained no protein molecules, as expected (see lack of Coomassie blue staining at lane 3 of FIG. 9B). In contrast, the protein-conjugated nanoparticle preparations stained with Coomassie blue (lanes 4 and 5 of FIG. 9B) and the stain co-migrated with the iron signal (lanes 4 and 5 of FIG. 9A). Electrophoresis of these preparations on 5% polyacrylamide gels further indicated that virtually all the protein content in both preps was on the nanoparticles, with undetectable levels of non-conjugated protein in the solution (FIG. 9C). As expected the nanoparticles, unlike control unconjugated pMHC monomers in solution, did not migrate into the gel owing to their size.

We next compared the abilities of the pMHC and pMHC/anti-CD28 mAb-conjugated nanoparticles to stimulate and activate cognate naive CD8+ T cells derived from a transgenic NOD mice expressing an $IGRP_{206-214}/K^d$-reactive TCR transgene. This was done by measuring the proliferative and interferon-gamma secreting activities of the naive CD8+ T-cells of these mice (right and left panels in FIGS. 10A-10B, respectively) ($2.5 \times 10^5$ cells/mL) in response to serially diluted nanoparticle preparations. As shown in FIGS. 10A-10B, pMHC/anti-CD28 mAb-conjugated nanoparticles (FIG. 10B) had significantly higher agonistic activity than nanoparticles coated with pMHC alone (FIG. 10A). pMHC/anti-CD28 mAb-conjugated nanoparticles induced maximum proliferation (FIG. 10B, right panel) and interferon-gamma secretion (FIG. 10B, left panel) at low nanoparticle densities and these values were substantially higher than the maximum values obtained for pMHC-conjugated nanoparticles (FIG. 10A) at the highest densities tested.

Example 12. Expression, Purification and Functional Characterization of a Recombinant Mouse B7.1-hFc Fusion Protein Ideally, pMHC-coated nanoparticles aimed at activating naive T-cells could be coated with a whole range of co-stimulatory molecules capable of engaging cognate signal-transducing receptors on the T-cell's surface (i.e. CD28 for B7.1, as is the case for anti-CD28 mAb). This would be particularly useful for receptors for which agonistic mAbs are not available. To test the feasibility of this approach, we generated a DNA construct encoding a mouse B7.1 (mB7.1)-hFc fusion protein (using a flexible GS linked spacing the B7.1 and hFc protions) for expression in *Drosophila* S2 cells (using the pMT/V5 vector) or Chinese Hamster Ovary (CHO) cells (using a pcDNA3.3 vector). The fusion protein includes a mB7.1 fragment (209 a.a., D37-K245), followed by the human IgG1 (hIgG1) CH2 region (227 a.a,). The fusion protein was purified from culture supernatants by affinity chromatography on Protein A-Sepharose. The nucleotide and amino acid sequence of the fusion protein are shown in FIGS. 11A-11B.

To test the costimulatory activity of the mB7.1-hFc fusion, we purified naive CD4+ T cells from wild-type NOD mice and cultured them in the presence of serial dilutions of mB7.1-hFc in the presence of a suboptimal concentration of an agonistic anti-CD3 mAb immobilized onto the plates. Cultures incubated only in the presence of the immobilized anti-CD3 mAb or anti-CD28 mAb alone (negative controls) did not proliferate (giving background levels of $H^3$ thymidine incorporation; data not shown). The addition of anti-CD28 mAb to cultures on plates coated with anti-CD3 mAb dramatically increased the levels of $H^3$ thymidine incorporation (positive control). The addition of mB7.1-hFc to cultures plated in the presence of suboptimal concentrations of anti-CD3 mAb induced concentration-dependent increases in the proliferative activity of the naive CD4+ T-cells, regardless of whether the fusion protein was produced in S2 or CHO cells (FIG. 12). This demonstrated that the fusion protein as designed can effectively deliver a co-stimulatory signal to TCR-stimulated T-cells. Such a design will therefore serve as a template for the engineering of fusion proteins encoding other co-stimulatory molecules to be conjugated onto pMHC-coated nanoparticles for activation and expansion of antigen-specific T-cells in vivo.

Thus, it should be understood that although the present invention has been specifically disclosed by preferred embodiments and optional features, modification, improvement and variation of the inventions embodied therein herein disclosed may be resorted to by those skilled in the art, and that such modifications, improvements and variations are considered to be within the scope of this invention. The materials, methods, and examples provided here are representative of preferred embodiments, are exemplary, and are not intended as limitations on the scope of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

Throughout this disclosure, various publications, patents and published patent specifications are referenced by an identifying citation. All publications, patent applications, patents, and other references mentioned herein are expressly incorporated by reference in their entirety, to the same extent as if each were incorporated by reference individually. In case of conflict, the present specification, including definitions, will control.

What is claimed is:

1. A complex comprising:
   (a) a nanoparticle core having a diameter from about 1 nm to about 100 nm;
   (b) from 10 to 500 cancer or tumor-relevant antigen/CD1 protein complexes coupled to the nanoparticle core; and
   (c) a plurality of co-stimulatory molecule complexes coupled to the nanoparticle core;
   wherein the ratio of co-stimulatory molecule complexes to the cancer or tumor-relevant antigen/CD1 protein complexes is from about 0.1:1 to about 50:1.

2. The complex of claim 1, wherein the nanoparticle core has a biodegradable layer on the outer surface of the nanoparticle core and from 10 to 500 cancer or tumor-relevant antigen/CD1 protein complexes and the co-stimulatory molecule complexes of the plurality are coupled to the nanoparticle core or the biodegradable layer on the nanoparticle core.

3. The complex of claim 1 or 2, wherein the ratio of co-stimulatory molecule complexes to the cancer or tumor-relevant antigen/CD1 protein complexes is from about 1:1 to about 50:1.

4. The complex of claim 1 or 2, wherein the nanoparticle core has a diameter from about 1 nm to about 50 nm.

5. The complex of claim 1 or 2, wherein the nanoparticle core has a diameter from about 1 nm to about 30 nm.

6. The complex of claim 1 or 2, wherein the co-stimulatory molecule complexes coupled to the nanoparticle core are identical.

7. The complex of claim 1 or 2, wherein the tumor-relevant antigen is a cancerous tumor relevant antigen.

8. The complex of claim 7, wherein the antigen is a melanoma-relevant antigen or a lung cancer-relevant antigen.

9. The complex of claim 1 or 2, wherein a plurality of identical cancer or tumor-relevant antigen epitopes are contained in the cancer or tumor relevant antigen/MHC complexes.

10. The complex of claim 9, wherein the plurality of antigen epitopes are derived from a single antigen or a plurality of antigens.

11. The complex of claim 1 or 2, wherein the co-stimulatory molecule complexes of the plurality comprise a co-stimulatory molecule selected from the group of the CD28 receptor (CD80(B7.1), CD86(B7.2)), 4-IBBL, CD40, IL-15/IL15Rα, and ICOS.

12. The complex of claim 1 or 2, wherein the nanoparticle core comprises one or more of a metal, a metal oxide, a metal sulfide, a metal selenide, a magnetic material, a polymer, gold, iron, or iron oxide.

13. The complex of claim 12, wherein the nanoparticle core comprises one or more of gold, iron, or iron oxide.

14. The complex of claim 1 or 2, wherein the nanoparticle core is biocompatible and bioabsorbable.

15. The complex of claim 1, wherein the co-stimulatory molecule complexes of the plurality and/or the cancer or tumor-relevant antigen/CD1 protein complexes of the plurality are covalently coupled to the nanoparticle core or the biodegradable layer.

16. The complex of claim 2, wherein the co-stimulatory molecule complexes of the plurality and/or the cancer or tumor-relevant antigen/CD1 protein complexes of the plurality are covalently coupled to the biodegradable layer.

17. The complex of claim 1, wherein the co-stimulatory molecule complexes of the plurality and/or the cancer or tumor-relevant antigen/CD1 protein complexes of the plurality are covalently coupled to the nanoparticle core via a linker.

18. The complex of claim 2, wherein the co-stimulatory molecule complexes of the plurality and/or the cancer or tumor-relevant antigen/CD1 protein complexes of the plurality are covalently coupled to the biodegradable layer via a linker.

19. The complex of claim 17, wherein the linker comprises ethylene glycol.

20. The complex of claim 18, wherein the linker comprises ethylene glycol.

21. The complex of claim 2, wherein the biodegradable layer on the nanoparticle core comprises dextran, mannitol, and/or poly(ethylene glycol).

22. The complex of claim 1, wherein the co-stimulatory molecule complexes of the plurality and/or the cancer or tumor-relevant antigen/CD1 protein complexes of the plurality are coupled to the nanoparticle core, each via one or more of a dimer, a trimer, and/or a dimer of a trimer.

23. The complex of claim 2, wherein the co-stimulatory molecule complexes of the plurality and/or the cancer or tumor-relevant antigen/CD1 protein complexes of the plurality are coupled to the nanoparticle core or the biodegradable layer on the nanoparticle core, each via one or more of a dimer, a trimer, and/or a dimer of a trimer.

24. A pharmaceutical composition comprising a plurality of complexes of claim 1 or 2.

25. The pharmaceutical composition of claim 24, further comprising a carrier.

* * * * *

```
                            SEQUENCE LISTING

<160> NUMBER OF SEQ ID NOS: 105

<210> SEQ ID NO 1
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Lys Ile Ser Val Ser Leu Pro Leu Ser Leu Ser Gln Ser Val Cys
1               5                   10                  15

<210> SEQ ID NO 2
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gln Leu Ser Lys Asp Thr Ser Val Leu Thr Phe Thr Phe Cys
1               5                   10

<210> SEQ ID NO 3
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Cys Ser Asp Ala His Pro Gly Asp Ser Ser Gly Asp Ser Ser Gly Leu
1               5                   10                  15

Asn

<210> SEQ ID NO 4
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Arg Gly Glu Val Arg Gln Phe Thr Leu Arg His Trp Leu Lys Val
1               5                   10                  15

<210> SEQ ID NO 5
```

-continued

```
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gly Asp Tyr Leu Asn Asp Glu Ala Leu Trp Asn Lys Cys
1               5                   10

<210> SEQ ID NO 6
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gly Lys Val Ile Asp Asn Asp His Leu Ser Gln Glu Ile Cys
1               5                   10                  15

<210> SEQ ID NO 7
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Leu Met Ala Asn Ser Thr Trp Gly Tyr Pro Phe His Asp Gly
1               5                   10

<210> SEQ ID NO 8
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Leu Asn Val Val Pro Trp Asn Leu Thr Leu Phe Ser Ile Leu
1               5                   10

<210> SEQ ID NO 9
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Thr His Ser Phe Thr Ala Phe Lys Arg His Val Cys
1               5                   10

<210> SEQ ID NO 10
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10
```

```
Asn Leu Ser Leu Pro Pro Ser Leu Ser Leu Ser Ile Cys
1               5                   10
```

<210> SEQ ID NO 11
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

```
Glu Arg Pro Ser Ser Val Leu Thr Ile Tyr Asp Ile Gly Ile Gln Cys
1               5                   10                  15
```

<210> SEQ ID NO 12
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

```
Cys Tyr Gln Gln Tyr Thr Asn Leu Gln Glu Arg Pro Ser Ser Val
1               5                   10                  15
```

<210> SEQ ID NO 13
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

```
Thr Val Glu Pro Glu Thr Gly Asp Pro Val Thr Leu Arg Leu Cys
1               5                   10                  15
```

<210> SEQ ID NO 14
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

```
Cys Ser Arg Lys Lys Arg Ala Asp Lys Lys Glu Asn Gly Thr Lys Leu
1               5                   10                  15

Leu
```

<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

```
Phe Leu Leu Val Leu Gly Phe Ile Ile
1               5
```

<210> SEQ ID NO 16
<211> LENGTH: 9
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 16

Val Leu Pro Ser Val Ala Met Phe Leu
1               5

<210> SEQ ID NO 17
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Leu Val Leu Gly Phe Ile Ile Ala Leu
1               5

<210> SEQ ID NO 18
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Lys Val Val Thr Ser Ser Phe Val Val
1               5

<210> SEQ ID NO 19
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Leu Val Pro Gly Thr Lys Phe Tyr Ile
1               5

<210> SEQ ID NO 20
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Leu Leu Pro Ile Arg Thr Leu Pro Leu
1               5

<210> SEQ ID NO 21
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Tyr Leu Val Lys Lys Gly Thr Ala Thr
1               5
```

<210> SEQ ID NO 22
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Ser Leu Phe Ala Glu Thr Ile Trp Val
1               5

<210> SEQ ID NO 23
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Met Leu Ile Ala Met Tyr Phe Tyr Thr
1               5

<210> SEQ ID NO 24
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Leu Met Trp Thr Leu Pro Val Met Leu
1               5

<210> SEQ ID NO 25
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Met Leu Ile Val Tyr Ile Phe Glu Cys
1               5

<210> SEQ ID NO 26
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Tyr Ile Phe Glu Cys Ala Ser Cys Ile
1               5

<210> SEQ ID NO 27
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 27

Leu Val Leu Met Leu Ile Val Tyr Ile
1               5

<210> SEQ ID NO 28
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Ala Leu Cys Arg Arg Arg Ser Met Val
1               5

<210> SEQ ID NO 29
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Leu Leu Ser Gly Leu Ser Leu Phe Ala
1               5

<210> SEQ ID NO 30
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Phe Leu Leu Val Val Gly Leu Ile Val
1               5

<210> SEQ ID NO 31
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Leu Val Val Gly Leu Ile Val Ala Leu
1               5

<210> SEQ ID NO 32
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Lys Val Val Lys Ser Asp Phe Val Val
1               5

<210> SEQ ID NO 33
<211> LENGTH: 9
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Thr Leu Pro Val Gln Thr Leu Pro Leu
1               5

<210> SEQ ID NO 34
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Asp Leu His Val Ile Ser Asn Asp Val
1               5

<210> SEQ ID NO 35
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Val Leu Val His Pro Gln Trp Val Leu
1               5

<210> SEQ ID NO 36
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Phe Leu Arg Pro Gly Asp Asp Ser Ser
1               5

<210> SEQ ID NO 37
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Ala Leu Gly Thr Thr Cys Tyr Ala Ser
1               5

<210> SEQ ID NO 38
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Lys Leu Gln Cys Val Asp Leu His Val
```

```
<210> SEQ ID NO 39
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Glu Leu Ala His Tyr Asp Val Leu Leu
1               5

<210> SEQ ID NO 40
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Asn Leu Asn Gly Ala Gly Asp Pro Leu
1               5

<210> SEQ ID NO 41
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Thr Leu Arg Val Asp Cys Thr Pro Leu
1               5

<210> SEQ ID NO 42
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Met Met Asn Asp Gln Leu Met Phe Leu
1               5

<210> SEQ ID NO 43
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Ala Leu Phe Asp Ile Glu Ser Lys Val
1               5

<210> SEQ ID NO 44
<211> LENGTH: 9
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 44

Leu Leu His Glu Thr Asp Ser Ala Val
1               5

<210> SEQ ID NO 45
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Val Leu Ala Lys Glu Leu Lys Phe Val
1               5

<210> SEQ ID NO 46
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Ile Leu Leu Trp Gln Pro Ile Pro Val
1               5

<210> SEQ ID NO 47
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Asp Leu Phe Gly Ile Trp Ser Lys Val
1               5

<210> SEQ ID NO 48
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Pro Leu Glu Arg Phe Ala Glu Leu Val
1               5

<210> SEQ ID NO 49
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Lys Gln Gly Asn Phe Asn Ala Trp Val
1               5

<210> SEQ ID NO 50

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Asn Leu Leu Arg Arg Met Trp Val Thr
1               5

<210> SEQ ID NO 51
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Asn Leu Phe Glu Thr Pro Ile Leu Ala
1               5

<210> SEQ ID NO 52
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Asn Leu Phe Glu Thr Pro Val Glu Ala
1               5

<210> SEQ ID NO 53
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Gly Leu Gln His Trp Val Pro Glu Leu
1               5

<210> SEQ ID NO 54
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Val Gln Phe Val Ala Ser Tyr Lys Val
1               5

<210> SEQ ID NO 55
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55
```

Arg Leu Leu Ala Ala Leu Cys Gly Ala
1               5

<210> SEQ ID NO 56
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Leu Leu Leu Leu Thr Val Leu Thr Val
1               5

<210> SEQ ID NO 57
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Leu Leu Leu Thr Val Leu Thr Val Val
1               5

<210> SEQ ID NO 58
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Phe Leu Ser Phe His Ile Ser Asn Leu
1               5

<210> SEQ ID NO 59
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Leu Leu Val Leu Val Cys Val Leu Val
1               5

<210> SEQ ID NO 60
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Ala Leu Leu Val Leu Val Cys Val Leu
1               5

<210> SEQ ID NO 61
<211> LENGTH: 9
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 61

Ser Leu Ser Tyr Thr Asn Pro Ala Val
1               5

<210> SEQ ID NO 62
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Asn Leu Thr Ile Ser Asp Val Ser Val
1               5

<210> SEQ ID NO 63
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Ala Leu Ala Ser Thr Ala Pro Pro Val
1               5

<210> SEQ ID NO 64
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Ala Ile Leu Cys Trp Thr Phe Trp Val
1               5

<210> SEQ ID NO 65
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Phe Ile Leu Met Phe Ile Val Tyr Ala
1               5

<210> SEQ ID NO 66
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Leu Thr Ala Glu Cys Ile Phe Phe Val
1               5
```

```
<210> SEQ ID NO 67
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Met Leu Gln Asp Asn Cys Cys Gly Val
1               5

<210> SEQ ID NO 68
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Ile Leu Cys Trp Thr Phe Trp Val Leu
1               5

<210> SEQ ID NO 69
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Lys Ile Leu Leu Ala Tyr Phe Ile Leu
1               5

<210> SEQ ID NO 70
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Phe Val Gly Ile Cys Leu Phe Cys Leu
1               5

<210> SEQ ID NO 71
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Val Leu Leu Ser Val Ala Met Phe Leu
1               5

<210> SEQ ID NO 72
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72
```

```
Leu Leu Ser Val Ala Met Phe Leu Leu
1               5

<210> SEQ ID NO 73
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Ile Leu Gly Ser Leu Pro Phe Phe Leu
1               5

<210> SEQ ID NO 74
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Ile Leu Asn Ala Tyr Leu Val Arg Val
1               5

<210> SEQ ID NO 75
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Phe Leu Leu Val Gly Phe Ala Gly Ala
1               5

<210> SEQ ID NO 76
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Asn Leu Gln Pro Gln Leu Ala Ser Val
1               5

<210> SEQ ID NO 77
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Cys Met Phe Asp Ser Lys Glu Ala Leu
1               5

<210> SEQ ID NO 78
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 78

Tyr Leu Tyr Val Leu Val Asp Ser Ala
1               5

<210> SEQ ID NO 79
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Tyr Met Asp Gly Thr Met Ser Gln Val
1               5

<210> SEQ ID NO 80
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Lys Met Ala Arg Phe Ser Tyr Ser Val
1               5

<210> SEQ ID NO 81
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Gly Leu Val Met Asp Glu His Leu Val
1               5

<210> SEQ ID NO 82
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Phe Leu Pro Gly Cys Asp Gly Leu Val
1               5

<210> SEQ ID NO 83
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Cys Met Leu Gly Ser Phe Cys Ala Cys
1               5
```

```
<210> SEQ ID NO 84
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Tyr Leu Ala Phe Arg Asp Asp Ser Ile
1               5

<210> SEQ ID NO 85
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Trp Leu Pro Lys Lys Cys Ser Leu Cys
1               5

<210> SEQ ID NO 86
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Cys Leu Asn Gly Gly Thr Cys Met Leu
1               5

<210> SEQ ID NO 87
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Met Leu Val Gly Ile Cys Leu Ser Ile
1               5

<210> SEQ ID NO 88
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Phe Glu Leu Gly Leu Val Ala Gly Leu
1               5

<210> SEQ ID NO 89
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 89

Lys Met Val Arg Phe Ser Tyr Ser Val
1               5

<210> SEQ ID NO 90
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Cys Leu Asn Glu Gly Thr Cys Met Leu
1               5

<210> SEQ ID NO 91
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Met Leu Ala Gly Ile Cys Leu Ser Ile
1               5

<210> SEQ ID NO 92
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Arg Leu Leu Phe Phe Leu Leu Phe Leu
1               5

<210> SEQ ID NO 93
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Thr Leu Ala Tyr Leu Ile Phe Cys Leu
1               5

<210> SEQ ID NO 94
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Leu Leu Phe Leu Thr Pro Met Glu Val
1               5

<210> SEQ ID NO 95
<211> LENGTH: 9
<212> TYPE: PRT
```

-continued

```
<213> ORGANISM: Artificial Sequence
<220> FEATURE:
<223> OTHER INFORMATION: Description of Artificial Sequence: Synthetic
      peptide

<400> SEQUENCE: 95

Lys Leu Met Ser Pro Lys Leu Tyr Val
1               5

<210> SEQ ID NO 96
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Leu Leu Phe Phe Leu Leu Phe Leu Val
1               5

<210> SEQ ID NO 97
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Ser Leu Phe Leu Gly Ile Leu Ser Val
1               5

<210> SEQ ID NO 98
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Ala Ile Ser Gly Met Ile Leu Ser Ile
1               5

<210> SEQ ID NO 99
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Phe Ile Arg Ala His Thr Pro Tyr Ile
1               5

<210> SEQ ID NO 100
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Ser Leu Asn Phe Ile Arg Ala His Thr
1               5
```

<210> SEQ ID NO 101
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Leu Lys Met Glu Ser Leu Asn Phe Ile
1               5

<210> SEQ ID NO 102
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Ser His Phe Leu Lys Met Glu Ser Leu
1               5

<210> SEQ ID NO 103
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Tyr Leu Phe Leu Gly Ile Leu Ser Val
1               5

<210> SEQ ID NO 104
<211> LENGTH: 1422
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(1419)

<400> SEQUENCE: 104 atg gct atc atc tac ctc atc ctc ctg ttc acc gct gtg cgg ggc gat        48
Met Ala Ile Ile Tyr Leu Ile Leu Leu Phe Thr Ala Val Arg Gly Asp
1               5                   10                  15 gtt gat gaa caa ctg tcc aag tca gtg aaa gat aag gta ttg ctg cct        96
Val Asp Glu Gln Leu Ser Lys Ser Val Lys Asp Lys Val Leu Leu Pro
            20                  25                  30 tgc cgt tac aac tct cct cat gaa gat gag tct gaa gac cga atc tac       144
Cys Arg Tyr Asn Ser Pro His Glu Asp Glu Ser Glu Asp Arg Ile Tyr
        35                  40                  45 tgg caa aaa cat gac aaa gtg gtg ctg tct gtc att gct ggg aaa cta       192
Trp Gln Lys His Asp Lys Val Val Leu Ser Val Ile Ala Gly Lys Leu
    50                  55                  60 aaa gtg tgg ccc gag tat aag aac cgg act tta tat gac aac act acc       240
Lys Val Trp Pro Glu Tyr Lys Asn Arg Thr Leu Tyr Asp Asn Thr Thr
65                  70                  75                  80 tac tct ctt atc atc ctg ggc ctg gtc ctt tca gac cgg ggc aca tac       288
Tyr Ser Leu Ile Ile Leu Gly Leu Val Leu Ser Asp Arg Gly Thr Tyr -continued

|  |  |  |  | 85 |  |  |  | 90 |  |  |  | 95 |  |  |  |
|---|---|---|---|---|---|---|---|---|---|---|---|---|---|---|---|
| agc | tgt | gtc | gtt | caa | aag | aag | gaa | aga | gga | acg | tat | gaa | gtt | aaa | cac | 336 |
| Ser | Cys | Val | Val | Gln | Lys | Lys | Glu | Arg | Gly | Thr | Tyr | Glu | Val | Lys | His |
|  |  |  | 100 |  |  |  |  | 105 |  |  |  |  | 110 |  |  |

| ttg | gct | tta | gta | aag | ttg | tcc | atc | aaa | gct | gac | ttc | tct | acc | ccc | aac | 384 |
| Leu | Ala | Leu | Val | Lys | Leu | Ser | Ile | Lys | Ala | Asp | Phe | Ser | Thr | Pro | Asn |
|  | 115 |  |  |  |  | 120 |  |  |  |  | 125 |  |  |  |  |

| ata | act | gag | tct | gga | aac | cca | tct | gca | gac | act | aaa | agg | att | acc | tgc | 432 |
| Ile | Thr | Glu | Ser | Gly | Asn | Pro | Ser | Ala | Asp | Thr | Lys | Arg | Ile | Thr | Cys |
| 130 |  |  |  |  | 135 |  |  |  |  | 140 |  |  |  |  |  |

| ttt | gct | tcc | ggg | ggt | ttc | cca | aag | cct | cgc | ttc | tct | tgg | ttg | gaa | aat | 480 |
| Phe | Ala | Ser | Gly | Gly | Phe | Pro | Lys | Pro | Arg | Phe | Ser | Trp | Leu | Glu | Asn |
| 145 |  |  |  | 150 |  |  |  |  | 155 |  |  |  |  | 160 |  |

| gga | aga | gaa | tta | cct | ggc | atc | aat | acg | aca | att | tcc | cag | gat | cct | gaa | 528 |
| Gly | Arg | Glu | Leu | Pro | Gly | Ile | Asn | Thr | Thr | Ile | Ser | Gln | Asp | Pro | Glu |
|  |  |  | 165 |  |  |  |  | 170 |  |  |  |  | 175 |  |  |

| tct | gaa | ttg | tac | acc | att | agt | agc | caa | cta | gat | ttc | aat | acg | act | cgc | 576 |
| Ser | Glu | Leu | Tyr | Thr | Ile | Ser | Ser | Gln | Leu | Asp | Phe | Asn | Thr | Thr | Arg |
|  |  | 180 |  |  |  |  | 185 |  |  |  |  | 190 |  |  |  |

| aac | cac | acc | att | aag | tgt | ctc | att | aaa | tat | gga | gat | gct | cac | gtg | tca | 624 |
| Asn | His | Thr | Ile | Lys | Cys | Leu | Ile | Lys | Tyr | Gly | Asp | Ala | His | Val | Ser |
|  | 195 |  |  |  |  | 200 |  |  |  |  | 205 |  |  |  |  |

| gag | gac | ttc | acc | tgg | gaa | aaa | ccc | cca | gaa | gac | cct | cct | gat | agc | aag | 672 |
| Glu | Asp | Phe | Thr | Trp | Glu | Lys | Pro | Pro | Glu | Asp | Pro | Pro | Asp | Ser | Lys |
| 210 |  |  |  |  | 215 |  |  |  |  | 220 |  |  |  |  |  |

| gac | aaa | act | cac | aca | tgc | cca | ccg | tgc | cca | gca | cct | gaa | gcc | gcg | ggg | 720 |
| Asp | Lys | Thr | His | Thr | Cys | Pro | Pro | Cys | Pro | Ala | Pro | Glu | Ala | Ala | Gly |
| 225 |  |  |  | 230 |  |  |  |  | 235 |  |  |  |  | 240 |  |

| gga | ccg | tca | gtc | ttc | ctc | ttc | ccc | cca | aaa | ccc | aag | gac | acc | ctc | atg | 768 |
| Gly | Pro | Ser | Val | Phe | Leu | Phe | Pro | Pro | Lys | Pro | Lys | Asp | Thr | Leu | Met |
|  |  |  | 245 |  |  |  |  | 250 |  |  |  |  | 255 |  |  |

| atc | tcc | cgg | acc | cct | gag | gtc | aca | tgc | gtg | gtg | gtg | gac | gtg | agc | cac | 816 |
| Ile | Ser | Arg | Thr | Pro | Glu | Val | Thr | Cys | Val | Val | Val | Asp | Val | Ser | His |
|  |  | 260 |  |  |  |  | 265 |  |  |  |  | 270 |  |  |  |

| gaa | gac | cct | gag | gtc | aag | ttc | aac | tgg | tac | gtg | gac | ggc | gtg | gag | gtg | 864 |
| Glu | Asp | Pro | Glu | Val | Lys | Phe | Asn | Trp | Tyr | Val | Asp | Gly | Val | Glu | Val |
| 275 |  |  |  |  | 280 |  |  |  |  | 285 |  |  |  |  |  |

| cat | aat | gcc | aag | aca | aag | ccg | cgg | gag | gag | cag | tac | aac | agc | acg | tac | 912 |
| His | Asn | Ala | Lys | Thr | Lys | Pro | Arg | Glu | Glu | Gln | Tyr | Asn | Ser | Thr | Tyr |
|  | 290 |  |  |  |  | 295 |  |  |  |  | 300 |  |  |  |  |

| cgt | gtg | gtc | agc | gtc | ctc | acc | gtc | ctg | cac | cag | gac | tgg | ctg | aat | ggc | 960 |
| Arg | Val | Val | Ser | Val | Leu | Thr | Val | Leu | His | Gln | Asp | Trp | Leu | Asn | Gly |
| 305 |  |  |  |  | 310 |  |  |  |  | 315 |  |  |  |  | 320 |

| aag | gag | tac | aag | tgc | aag | gtc | tcc | aac | aaa | gcc | ctc | cca | gcc | ccc | atc | 1008 |
| Lys | Glu | Tyr | Lys | Cys | Lys | Val | Ser | Asn | Lys | Ala | Leu | Pro | Ala | Pro | Ile |
|  |  |  | 325 |  |  |  |  | 330 |  |  |  |  | 335 |  |  |

| gag | aaa | acc | atc | tcc | aaa | gcc | aaa | ggg | cag | ccc | cga | gaa | cca | cag | gtg | 1056 |
| Glu | Lys | Thr | Ile | Ser | Lys | Ala | Lys | Gly | Gln | Pro | Arg | Glu | Pro | Gln | Val |
|  | 340 |  |  |  |  | 345 |  |  |  |  | 350 |  |  |  |  |

| tac | acc | ctg | ccc | cca | tcc | cgg | gat | gag | ctg | acc | aag | aac | cag | gtc | agc | 1104 |
| Tyr | Thr | Leu | Pro | Pro | Ser | Arg | Asp | Glu | Leu | Thr | Lys | Asn | Gln | Val | Ser |
|  |  | 355 |  |  |  |  | 360 |  |  |  |  | 365 |  |  |  |

| ctg | acc | tgc | ctg | gtc | aaa | ggc | ttc | tat | ccc | agc | gac | atc | gcc | gtg | gag | 1152 |
| Leu | Thr | Cys | Leu | Val | Lys | Gly | Phe | Tyr | Pro | Ser | Asp | Ile | Ala | Val | Glu |
| 370 |  |  |  |  | 375 |  |  |  |  | 380 |  |  |  |  |  |

| tgg | gag | agc | aat | ggg | cag | ccg | gag | aac | aac | tac | aag | acc | acg | cct | ccc | 1200 |
| Trp | Glu | Ser | Asn | Gly | Gln | Pro | Glu | Asn | Asn | Tyr | Lys | Thr | Thr | Pro | Pro |
| 385 |  |  |  | 390 |  |  |  |  | 395 |  |  |  |  | 400 |  |

| gtg | ttg | gac | tcc | gac | ggc | tcc | ttc | ttc | ctc | tac | agc | aag | ctc | acc | gtg | 1248 |

-continued

```
Val Leu Asp Ser Asp Gly Ser Phe Phe Leu Tyr Ser Lys Leu Thr Val
                405                 410                 415 gac aag agc agg tgg cag cag ggg aac gtc ttc tca tgc tcc gtg atg    1296
Asp Lys Ser Arg Trp Gln Gln Gly Asn Val Phe Ser Cys Ser Val Met
        420                 425                 430 cat gag gct ctg cac aac cac tac acg cag aag agc ctc tcc ctg tct    1344
His Glu Ala Leu His Asn His Tyr Thr Gln Lys Ser Leu Ser Leu Ser
            435                 440                 445 ccg ggt aaa ggt agt ggt agt ggt agt gga tct ctg ggt ggt atc ttc    1392
Pro Gly Lys Gly Ser Gly Ser Gly Ser Gly Ser Leu Gly Gly Ile Phe
    450                 455                 460 gag gct atg aag atg gag ctg cgc gat tga                            1422
Glu Ala Met Lys Met Glu Leu Arg Asp
465                 470
```

<210> SEQ ID NO 105
<211> LENGTH: 473
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 105

```
Met Ala Ile Ile Tyr Leu Ile Leu Leu Phe Thr Ala Val Arg Gly Asp
1               5                   10                  15

Val Asp Glu Gln Leu Ser Lys Ser Val Lys Asp Lys Val Leu Leu Pro
            20                  25                  30

Cys Arg Tyr Asn Ser Pro His Glu Asp Glu Ser Glu Asp Arg Ile Tyr
        35                  40                  45

Trp Gln Lys His Asp Lys Val Val Leu Ser Val Ile Ala Gly Lys Leu
    50                  55                  60

Lys Val Trp Pro Glu Tyr Lys Asn Arg Thr Leu Tyr Asp Asn Thr Thr
65                  70                  75                  80

Tyr Ser Leu Ile Ile Leu Gly Leu Val Leu Ser Asp Arg Gly Thr Tyr
                85                  90                  95

Ser Cys Val Val Gln Lys Lys Glu Arg Gly Thr Tyr Glu Val Lys His
            100                 105                 110

Leu Ala Leu Val Lys Leu Ser Ile Lys Ala Asp Phe Ser Thr Pro Asn
        115                 120                 125

Ile Thr Glu Ser Gly Asn Pro Ser Ala Asp Thr Lys Arg Ile Thr Cys
    130                 135                 140

Phe Ala Ser Gly Gly Phe Pro Lys Pro Arg Phe Ser Trp Leu Glu Asn
145                 150                 155                 160

Gly Arg Glu Leu Pro Gly Ile Asn Thr Thr Ile Ser Gln Asp Pro Glu
                165                 170                 175

Ser Glu Leu Tyr Thr Ile Ser Ser Gln Leu Asp Phe Asn Thr Thr Arg
            180                 185                 190

Asn His Thr Ile Lys Cys Leu Ile Lys Tyr Gly Asp Ala His Val Ser
        195                 200                 205

Glu Asp Phe Thr Trp Glu Lys Pro Pro Glu Asp Pro Pro Asp Ser Lys
    210                 215                 220

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
```

-continued

```
                260                 265                 270
Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
        290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys Gly Ser Gly Ser Gly Ser Gly Ser Leu Gly Gly Ile Phe
    450                 455                 460

Glu Ala Met Lys Met Glu Leu Arg Asp
465                 470
```